US009726670B2

(12) United States Patent
Ataman-Onal et al.

(10) Patent No.: US 9,726,670 B2
(45) Date of Patent: *Aug. 8, 2017

(54) METHOD FOR THE ASSAY OF LIVER FATTY ACID BINDING PROTEIN, ACE AND CA 19-9 FOR THE IN VITRO DIAGNOSIS OF COLORECTAL CANCER

(75) Inventors: Yasemin Ataman-Onal, Reyrieux (FR); Corinne Beaulieu, Rilleiux la Pape (FR); Jean-Philippe Charrier, Tassin la Demi-Lune (FR); Genevieve Choquet-Kastylevsky, Francheville (FR); Sylvie Pons, Saint Genis les Ollieres (FR); Dominique Rolland, Saint Genis les Olllieres (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/452,034

(22) PCT Filed: Jul. 10, 2008

(86) PCT No.: PCT/FR2008/051293
§ 371 (c)(1),
(2), (4) Date: Dec. 14, 2009

(87) PCT Pub. No.: WO2009/019368
PCT Pub. Date: Feb. 12, 2009

(65) Prior Publication Data
US 2010/0151456 A1 Jun. 17, 2010

(30) Foreign Application Priority Data
Jul. 19, 2007 (FR) ...................... 07 05200

(51) Int. Cl.
*G01N 33/573* (2006.01)
*G01N 33/574* (2006.01)

(52) U.S. Cl.
CPC ................. *G01N 33/57419* (2013.01); *G01N 2333/70567* (2013.01)

(58) Field of Classification Search
CPC ................................................... G01N 33/574
See application file for complete search history.

(56) References Cited

U.S. PATENT DOCUMENTS

| | | | |
|---|---|---|---|
| 4,529,931 A | 7/1985 | Kuhns | |
| 5,002,870 A | 3/1991 | Leavitt et al. | |
| 5,223,789 A | 6/1993 | Katsuyama et al. | |
| 5,344,760 A | 9/1994 | Harvey et al. | |
| 5,360,715 A | 11/1994 | Leavitt et al. | |
| 6,001,632 A | 12/1999 | Braxton et al. | |
| 6,291,205 B1 | 9/2001 | Tuite et al. | |
| 6,451,528 B1 | 9/2002 | Carr et al. | |
| 6,518,411 B1 | 2/2003 | Murray et al. | |
| 8,029,979 B2 | 10/2011 | Schneider-Mergener et al. | |
| 2002/0160382 A1 | 10/2002 | Lasek et al. | |
| 2003/0082533 A1 | 5/2003 | Yue et al. | |
| 2003/0087818 A1 | 5/2003 | Jiang et al. | |
| 2003/0109690 A1 | 6/2003 | Ruben et al. | |
| 2003/0172388 A1 | 9/2003 | Fujise et al. | |
| 2004/0157278 A1 | 8/2004 | Astle et al. | |
| 2004/0191782 A1 | 9/2004 | Wang | |
| 2004/0197930 A1 | 10/2004 | Rosenfeld et al. | |
| 2005/0181398 A1 | 8/2005 | Fung et al. | |
| 2005/0214826 A1* | 9/2005 | Mor et al. | 435/6 |
| 2006/0003359 A1 | 1/2006 | Feinberg et al. | |
| 2006/0179496 A1 | 8/2006 | Burgess et al. | |
| 2006/0205014 A1 | 9/2006 | Dotan et al. | |
| 2007/0020707 A1 | 1/2007 | Holten-Andersen et al. | |
| 2009/0239794 A1 | 9/2009 | Soudeyns et al. | |
| 2011/0104701 A1 | 5/2011 | Ataman-Onal et al. | |

FOREIGN PATENT DOCUMENTS

| | | |
|---|---|---|
| AT | 500 719 A1 | 3/2006 |
| CN | 1396182 A | 2/2003 |
| DE | 29 20 484 A1 | 12/1980 |
| DE | 196 42 472 A1 | 4/1998 |
| EP | 0 496 174 A1 | 7/1992 |
| EP | 1 724 586 A2 | 11/2006 |
| EP | 1 775 590 A1 | 4/2007 |
| FR | 2 581 456 A1 | 11/1986 |
| JP | 2-287266 A | 11/1990 |
| JP | 4-64068 A | 2/1992 |
| JP | 2001-069971 A | 3/2001 |
| WO | 95/16462 A1 | 6/1995 |
| WO | WO 00/33083 A1 | 6/2000 |
| WO | WO 00/50588 A2 | 8/2000 |
| WO | 01/31019 A2 | 5/2001 |
| WO | 01/71357 A2 | 9/2001 |

(Continued)

OTHER PUBLICATIONS

Kayser et al, APMIS 110:435-46, 2002.*
Yamazaki et al, J. Surg. Only 72:83-87, 1999, IDS filed on Jun. 28, 2010, #50.*
Kuusela et al, Br. K. Cancer 49:135-139, 1984.*
Pelsers et al , Clinica Chimica Acta 352:15-35, 2005.*
Lurisci et al, Cancer Res 6:1389-1393, 2000.*
Lawrie et al, British J Cancer, 90: 1955-1960, 2004.*
Jeck et al, Dis Colon Rectumr 39:1-26-30, 1996, abstract only.*
Mayo Clinic online publication , two page, 2002.*
Niederkofler et al., "Novel Mass Spectrometric Immunoassays for the Rapid Structural Characterization of Plasma Apolipoproteins," Journal of Lipid Research, vol. 44, pp. 630-639, 2003.
Hortin, "The MALDI-TOF Mass Spectrometric View of the Plasma Proteome and Pepetidome," Clinical Chemistry, vol. 52, No. 7, pp. 1223-1237, 2006.

(Continued)

Primary Examiner — Lei Yao
(74) Attorney, Agent, or Firm — Oliff PLC

(57) ABSTRACT

A method for the in vitro diagnosis of colorectal cancer by determining the presence of Liver Fatty Acid-Binding Protein, ACE and CA19-9 tumor markers in a biological sample taken from a patient suspected of having colorectal cancer. Said method can be used for early diagnosis, screening, therapeutic follow-up and prognosis, and also for relapse diagnosis in relation to colorectal cancer.

32 Claims, 12 Drawing Sheets

(56) References Cited

FOREIGN PATENT DOCUMENTS

Figure 1:
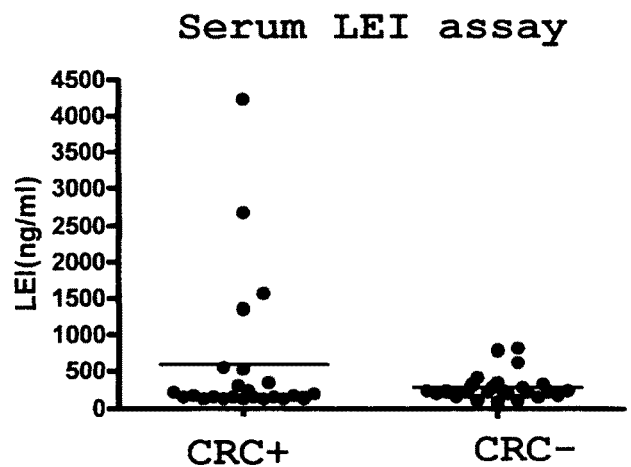

| WO | WO 02/20731 A2 | 3/2002 |
|---|---|---|
| WO | WO 03/065003 A2 | 8/2003 |
| WO | WO 03/087831 A2 | 10/2003 |
| WO | WO 2004/073730 A1 | 9/2004 |
| WO | WO 2005/015218 A1 | 2/2005 |
| WO | WO 2005/015219 A1 | 2/2005 |
| WO | WO 2005/015226 A1 | 2/2005 |
| WO | 2005/035003 A2 | 4/2005 |
| WO | 2005/060996 A2 | 7/2005 |
| WO | WO 2005/083440 A2 | 9/2005 |
| WO | WO 2006/015079 A2 | 2/2006 |
| WO | WO 2006/074360 A2 | 7/2006 |
| WO | WO 2007/002535 A2 | 1/2007 |
| WO | WO 2007/005578 A1 | 1/2007 |
| WO | WO 2007/020522 A2 | 2/2007 |
| WO | WO 2007/068985 A2 | 6/2007 |
| WO | WO 2007/140352 A2 | 12/2007 |
| WO | WO 2008/021290 A2 | 2/2008 |
| WO | WO 2008/028968 A2 | 3/2008 |
| WO | WO 2008/036981 A1 | 3/2008 |

OTHER PUBLICATIONS

Hachem, "Serum Apolipoproteins A-I, A-II and B in Hepatic Metastases Comparison with other Liver Diseases: Hepatomas and Cirrhosis," J. Clin. Chem. Clin. Biochem., vol. 24, pp. 161-166, 1986.
Remold-O'Donnell et al., "Sequence and Molecular Characterization of Human Monocyte/Neutrophil Elastase Inhibitor," Proc. Natl. Acad. Sci., vol. 89, pp. 5635-5639, Jun. 1992.
Cooley et al., "The Serpin MNEI Inhibits Elastase-Like and Chymotrypsin-Like Serine Proteases through Efficient Reactions at Two Active Sites," Biochemistry, vol. 40, pp. 15762-15770, 2001.
Algrain et al, "Ezrin Contains Cytoskeleton and Membrane Binding Domains Accounting for its Proposed Role as a Membrane-Cytoskeletal Linker," The Journal of Cell Biology, vol. 120, No. 1, pp. 129-139, Jan. 1993.
Jiang et al., "Cytokine Regulation of Ezrin Expression in the Human Colon Cancer Cell Line HT29," Anticancer Research, vol. 16, pp. 861-866, 1996.
Hiscox et al, "Ezri in Regulates Cell-Cell and Cell-Matrix Adhesion, a Possible Role with E-Cadherin/β-Catenin," Journal of Cell Science, vol. 112, pp. 3081-3090, 1999.
Xiao et al., "An Approach to Studying Lung Cancer-Related Proteins in Human Blood," Molecular & Cellular Proteomics, vol. 4, pp. 1480-1486, 2005.
Anders et al., "Aminoacyclases," Advances in Pharmacology, vol. 27, pp. 431-448, 1994.
Lorentz et al., "A New Method for the Assay of Aminoacylase: Elaboration of a Fixed-Incubation Method for Routine Measurements," Clinica Chimica Acta, vol. 63, pp. 263-269, 1975.
Lorentz et al, "Clinical Application of a New Method for the Determination of Aminoacylase in Human Serum," Clinica Chimica Acta, vol. 63, pp. 271-274, 1975.
Cook et al, "Human Aminoacylase-1," The Journal of Biological Chemistry, vol. 268, No. 23, pp. 17010-17017, 1993.
Miller at al., "Lack of Expression of Aminoacylae-1 in Small Cell Lung Cancer," The Journal of Clinical Investigation, Inc., vol. 83, pp. 2120-2124, Jun. 1989.
Balabanov et al., "Tumour-Related Enzyme Alterations in the Clear Cell Type of Human Renal Cell Carcinoma Identified by Two-dimensional Gel Electrophoresis," Eur. J. Biochem., vol. 268, pp. 5977-5980, 2001.
Chan et al, "Human Liver Fatty Acid Binding Protein cDNA and Amino Acid Sequence," The Journal of Biological Chemistry, vol. 260, No. 5, pp. 2629-2632, 1985.
Das et al., "Expression Pattern of Fatty Acid-Binding Proteins in Human Normal and Cancer Prostate Cells and Tissues," Clinical Cancer Research, vol. 7, 1706-1715, Jun. 2001.

Stulik et al., "Proteome Study of Colorectal Carcinogenesis," Electrophoresis, vol. 22, pp. 3019-3025, 2001.
Yamazaki et al., "Liver Fatty Acid-Binding Protein is a New Prognostic Factor for Hepatic Resection of Colorectal Cancer Metastases," Journal of Surgical Oncology, vol. 72, pp. 83-87, 1999.
Sweetser et al., "The Human and Rodent Intestinal Fatty Acid Binding Protein Genes," The Journal of Biological Chemistry, vol. 262, No. 33, pp. 16060-16071, 1987.
Pelsers et al, "Intestinal-Type and Liver-Type Fatty Acid-Binding Protein in the Intestine. Tissue Distribution and Clinical Utility", Clinical Biochemistry, vol. 36, pp. 529-535, 2003.
Xiao et al, "Dietary Exposure to Soy or Whey Proteins Alters Colonic Global Gene Expression Profiles During Rat Colon Tumorigenesis," Molecular Cancer, vol. 4, No. 1, pp. 1-17, Jan. 11, 2005.
Engwegen et al., "Identification of Serum Proteins Discriminating Colorectal Cancer Patients and Healthy Controls Using Surface-Enhanced Laser Desorption Ionisation-Time of Flight Mass Spectrometry," World J. Gastrenterol, vol. 12, No. 10, pp. 1536-1544, Mar. 14, 2006.
Zhang et al., "Three Biomarkers Identified from Serum Proteomic Analysis for the Detection of Early Stage Ovarian Cancer," Cancer Research, vol. 64, pp. 5882-5890, Aug. 15, 2004.
Lin et al., "Human Plastin Genes," The Journal of Biological Chemistry, vol. 268, No. 4, pp. 2781-2792, 1993.
Lavabre-Bertrand et al., "Plasma Proteasome Level is a Potential Marker in Patients with Solid Tumors and Hemopoietic Malignancies," Cancer, vol. 92, No. 10, pp. 2493-2500, Nov. 15, 2001.
Iurisci et al., "Concentrations of Galectin-3 in the Sera of Normal Controls and Cancer Patients," Clinical Cancer Research, vol. 6, pp. 1389-1393, Apr. 2000.
Schwartz, "Enzymes as Prognostic Markers and Therapeutic Indicators in Patients with Cancer," Clinics Chimica Acta, vol. 206, pp. 77-82, 1992.
McCool et al., "Roles of Calreticulin and Calnexin During Mucin Synthesis in LS180 and HT29/A1 Human Colonic Adenocarcinoma Cells," Biochem. J., vol. 341, pp. 593-600, 1999.
Motoo et al., "Serum Levels of Pancreatitis-Associated Protein in Digestive Diseases with Special Reference to Gastrointestinal Cancer," Digestive Diseases and Sciences, vol. 44, No. 6, pp. 1142-1147, Jun. 1999.
Abe et al., "Preparation of Recombinant MK-1/EP-CAM and Establishment of an ELISA System for Determining Soluble MK-1/EP-CAM Levels in Sera of Cancer Patients," Journal of Immunological Methods, vol. 270, pp. 227-233, 2002.
Katayama et al., "Soluble E-Cadherin Fragments Increased in Circulation of Cancer Patients," Br. J. Cancer, vol. 69, pp. 580-585, 1994.
Wilmanns et al., "Soluble Serum E-Cadherin as a Marker of Tumour Progression in Colorectal Cancer Patients," Clinical & Experimental Metastasis, vol. 21, pp. 75-78, 2004.
Gold et al., "Specific Carcinoembryonic Antigens of the Human Digestive System," J. Exp. Med., pp. 467-481, 1965.
Kim et al., "Gastrointestinal Tract Cancer Screening Using Fecal Carcinoembryonic Antigen," Annals of Clinical & Laboratory Science, vol. 33, No. 1, pp. 32-38, 2003.
Holmgren et al., "Detection by Monoclonal Antibody of Carbohydrate Antigen CA 50 in Serum of Patients with Carcinoma," British Medical Journal, vol. 288, pp. 1479-1482, May 19, 1984.
Klug et al., Monoclonal Anitbody Immunoradiometric Assay for an Antigenic Determinant (CA 72) on a Novel Pancarcinoma Antigen (TAG-72), Int. J. Cancer, vol. 38, pp. 661-669, 1986.
Holland et al., "Testosterona Serica: Posible Marcador En El Cancer Colorrectal," Medicina (Buenos Aires), vol. 53, pp. 117-123, 1993.
Model et al., Detection of Methylated DNA in Plasma from Colorectal Cancer Patients and Controls by Real-Time PCR Analysis of Septin 9, World Congress on Gastrointestinal Cancer, Jul. 2006.
Ebert et al., "Aristaless-like Homeobox-4 Gene Methylation is a Potential Marker for Colorectal Adenocarcinomas," Gastroenterology, vol. 131, pp. 1418-1430, 2006.

(56) References Cited

OTHER PUBLICATIONS

Bianco et al., "Identification of Cripto-I as a Novel Serologic Marker for Breast and Colon Cancer," Clin. Cancer Res., vol. 12, No. 17, pp. 5158-5164, Sep. 1, 2006.
Mori et al., "Two-Dimensional Electrophoresis Database of Fluorescence-Labeled Proteins of Colon Cancer Cells," Journal of Chromatography 13, vol. 823, pp. 82-97, 2005.
Duffy et al., "Tumour Markers in Colorectal Cancer: European Group on Tumour Markers (EGTM) Guidelines for Clinical Use," European Journal of Cancer, vol. 43, pp. 1348-1360, 2007.
Rouzier et al., "Immunocytochemical Detection of Bone Marrow Micrometastases in Colorectal Carcinoma Patients, Using a Monoclonal Antibody to Villin," Cytometry (Communication in Clinical Cytometry), vol. 46, pp. 281-289, 2001.
Nishizuka et al., "Diagnostic Markers that Distinguish Colon and Ovarian Adenocarcinomas: Identification by Genomic, Proteomic, and Tissue Array Profiling," Cancer Research, vol. 63, pp. 5243-5250, Sep. 1, 2003.
Wang et al., Proteomic Dissection of the Molecular Mechanisms Underlying Hepatic Metastasis in Colorectal Cancer, XP009093529, Database Accession No. PREV200600505326, AGA Abstracts, p. A-676, W1533, Apr. 2006.
Mori et al., A Genome-Wide Search Identifies Epigenetic Silencing of Somatostatin, Tachykinin-1, and 5 other Genes in Colon Cancer, Gastroenterology, vol. 131, pp. 797-808, 2006.
Database WPI Week 200777, Thomson Scientific, London, GB; AN 2007-817830, XP002464797 & CN 1 967 246 (Proteome Analysis Research Center) May 23, 2007, Abstract.
Fujiwara et al., Global Gene Expression Analysis of Rat Colon Cancers Induced by a Food-Borne Carcinogen, 2-amino-1-methyl-6-phenylimidazo[4,5-b]pyridine, Carcinogenesis, vol. 25, No. 8, pp. 1495-1505, 2004.
Dorudi et al., "E-Cadherin Expression in Colorectal Cancer," American Journal of Pathology, vol. 142, No. 4, pp. 981-986, Apr. 1993.
Lawrie ct al., "Liver Fatty Acid Binding Protein Expression in Colorectal Neoplasia," British Journal of Cancer, vol. 90, pp. 1955-1960, 2004.
Mar. 18, 2009 International Search Report Issued in International Application No. PCT/FR2008/051291.
Feb. 23, 2009 International Search Report Issued in International Application No. PCT/FR2008/051289.
Feb. 18, 2009 International Search Report Issued in International Application No. PCT/FR2008/051295.
Jan. 16, 2009 International Search Report Issued in International Application No. PCT/FR2008/051298.
Mar. 27, 2009 International Search Report Issued in International Application No. PCT/FR2008/051290.
Mar. 6, 2009 International Search Report Issued in International Application No. PCT/FR2008/051293.
Mar. 5, 2009 International Search Report Issued in International Application No. PCT/FR2008/051292.
U.S. Appl. No. 12/452,035, filed Dec. 14, 2009, in the name of Corinne Beaulieu et al.
U.S. Appl. No. 12/452,038, filed Dec. 14, 2009, in the name of Monique Arpin et al.
U.S. Appl. No. 12/452,037, filed Dec. 14, 2009, in the name of Yasemin Ataman-Onal et al.
U.S. Appl. No. 12/452,042, filed Dec. 14, 2009, in the name of Monique Arpin et al.
U.S. Appl. No. 12/452,048, filed Dec. 14, 2009, in the name of Jean-Philippe Charrier et al.
U.S. Appl. No. 12/452,047, filed Dec. 14, 2009, in the name of Yasemin Ataman-Onal et al.
Jan. 3, 2012 Office Action issued in U.S. Appl. No. 12/452,035.
Feb. 12, 2009 International Search Report Issued in International Application No. PCT/FR2008/051294.
Nov. 25, 2009 International Search Report Issued in International Application No. PCT/FR2009/051361 (w/ translation).
Jan. 9, 2012 Office Action issued in U.S. Appl. No. 12/452,047.
Feb. 3, 2012 Office Action issued in U.S. Appl. No. 12/452,048.
Feb. 1, 2012 Office Action issued in U.S. Appl. No. 12/452,037.
Otsuka et al. "Differential Expression of L-Plastin Gene in Human Colorectal Cancer Progression and Metastasis," Biochemical and Biophysical Research Communications, vol. 289, No. 4, pp. 876-881, 2001.
Shin et al.; "Global Profiling of the Cell Surface Proteome of Cancer Cells Uncovers an Abundance of Proteins with Chaperone Function;" The Journal of Biological Chemistry; Feb. 28, 2003; pp. 7607-7616; vol. 278, No. 9; The American Society for Biochemistry and Molecular Biology, Inc.; U.S.A.
Tomonaga et al.; "Identification of Altered Protein Expression and Post-Translational Modifications in Primary Colorectal Cancer by Using Agarose Two-Dimensional Gel Electrophoresis;" Clinical Cancer Research; vol. 10, Mar. 15, 2004; pp. 2007-2014.
Stierum et al.; "Proteome analysis reveals novel proteins associated with proliferation and differentiation of colorectal cancer cell line Caco-2;" Biochemica et Biophysica Acta; 2003; pp. 73-91; vol. 1650, No. 1-2.
Kaetzel et al.; "Protein Disulphide-isomerase from Human Placenta and Rat Liver—Purification and Immunological Characterization with Monoclonal Antibodies;" Biochem. J.; 1987; pp. 39-47; vol. 241, No. 1; Great Britain.
Kozaki et al.; "Tissue Distribution of ERp61 and Association of Its Increased Expression with IgG Production in Hybridoma Cells;" Experimental Cell Research; 1994; pp. 348-358; vol. 213, No. 2; Academic Press, Inc.
Leys et al.; "Expression and Prognostic Significance of Prothymosin-60 and ERp57 in Human Gastric Cancer;" Surgery; 2007; pp. 41-50; vol. 141, No. 1; Mosby Co.; St. Louis, MO, U.S.A.
Sass et al., "Mutations in ACY1, the Gene Encoding Aminoacylase 1, Cause a Novel Inborn Error of Metabolism", The American Journal of Human Genetics, Mar. 2006, vol. 78, pp. 401-409.
Tockman et al., "Considerations in Bringing a Cancer Biomarker to Clinical Application", Cancer Research, May 1, 1992, vol. 52, pp. 2711s-2718s.
Freeman et al., "APO-AII is an Elevated Biomarker of Chronic Non-Human Primate Ethanol Self-Administration", Alcohol & Alcoholism, Mar. 2006, vol. 41, No. 3, pp. 300-305.
Elsevier Publishing, "Human PDIA1 tryptic peptide—SEQ ID 33;" Retrieved from EBI accession No. GSP:ASS06881; Database Accession No. ASS06881, 2008.
Oct. 31, 2011Restriction and Election of Species Requirement issued in U.S. Appl. No. 12/452,035.
May 13, 2011 Restriction and Election of Species Requirement issued in U.S. Appl. No. 12/452,038.
Sep. 1, 2011 Office Action issued in U.S. Appl. No. 12/452,038.
Nov. 16, 2011 Election of Species Requirement issued in U.S. Appl. No. 12/452,037.
Sep. 15, 2011 Restriction and Election of Species Requirement issued in U.S. Appl. No. 12/452,042.
Oct. 28, 2011 Office Action issued in U.S. Appl. No. 12/452,042.
Oct. 28, 2011 Restriction Requirement issued in U.S. Appl. No. 12/452,047.
SCORE sequence search result #1, Geneseq Database, "20110423_191537_us-12-452-038-2.rag" Apr. 23, 2011.
Bruce et al., "Cancer-Wide Tissue Microarray Survey of Ezrin and Merlin Expression," Proc Amer Assoc Cancer Res, vol. 46, Abstract #424, 2005.
Gould et al., "cDNA Cloning and Sequencing of the Protein-Tyrosine Kinase Substrate, Ezrin, Reveals Homology to Band 4.1," The EMBO Journal, vol. 8, No. 13, pp. 4133-4142, 1989.
Etzioni et al., "The Case for Early Detection," Nature Review, vol. 3, Internet pp. 1-10, Apr. 2003.
Mercer, "Use of Multiple Markers to Enhance Clinical Utility," Immunol Ser., vol. 53, pp. 39-54, 1990.
Delanote et al., "Plastins: Versatile Modulators of Actin Organization in (patho)physiological Cellular Processes," Acta Pharmacologica Sinica, vol. 26, No. 7, pp. 769-779, Jul. 2005.
Hasselblatt et al., "Identification of Novel Diagnostic Markers for Choroid Plexus Tumors," Am. J. Surg Pathol, vol. 30, No. 1, pp. 66-74, Jan. 2006.

(56) References Cited

OTHER PUBLICATIONS

Lin et al., "Identification of I-Plastin, a Human Fimbrin Isoform Expressed in Intestine and Kidney," Molecular and Cellular Biology, vol. 14, No. 4, pp. 2457-2467, Apr. 1994.
Carroll et al., "Liver Fatty Acid-Binding Protein: A Marker for Studying Cellular Differentiation in Gut Epithelial Neoplasms," Gastroenterology, vol. 99, pp. 1727-1735, 1999.
Apr. 17, 2012 Office Action issued in U.S. Appl. No. 12/452,038.
Jun. 12, 2012 Office Action issued in U.S. Appl. No. 12/452,042.
Jun. 18, 2012 Office Action issued in U.S. Appl. No. 12/452,047.
Da Vies et al., "Loss of Cellular Distribution of Ezrin in Human Colon Cancer", ASCO 2006, Gastrointestinal Cancers Symposium, 2006 Abstract 322.
Mahipal et al., "Epidermal Growth Factor Receptor Overexpression in Resected Pancreatic Cancer", J Clinical Oncology, 2011, 29: suppl 4; Abstract 317.
Brattstrom et al., "HER-2 overexpression in patients with esophageal carcinoma correlates with poorer survival", ASCO 2005 Gastrointestinal Cancers Symposium, 2005, Abstract 63.
Kavanagh et al., "Is overexpression of HER-2 a predictor of prognosis in colorectal cancer?" BMC Cancer, Jan. 1, 2009, 9:1-6.
Dec. 28, 2012 Office Action issued in U.S. Appl. No. 12/452,037.
Office Action issued Jun. 21, 2012 in U.S. Appl. No. 12/452,035.
Jun. 18, 2013 Office Action issued in U.S. Appl. No. 12/452,037.
Restriction Requirement issued Jul. 24, 2012 in U.S. Appl. No. 12/999,242.
Office Action issued Aug. 3, 2012 in U.S. Appl. No. 12/452,037.
Office Action issued Jul. 31, 2012 in U.S. Appl. No. 12/452,048.
Oct. 15, 2013 Office Action issued in U.S. Appl. No. 12/452,037.
Apr. 23, 2014 Office Action issued in U.S. Appl. No. 13/712,340.
Sep. 10, 2014 Office Action issued in U.S. Appl. No. 13/732,521.
Sep. 19, 2014 Office Action issued in U.S. Appl. No. 13/712,340.
Majander-Nordenswan et al., "Genomic Structure of the Human Ezrin Gene," Human Genetics, vol. 103, 1998, pp. 662-665.
Sep. 8, 2015 Office Action issued in U.S. Appl. No. 14/701,002.
Giusti et al., "Proteome Analysis of Whole Saliva: A New Tool for Rheumatic Diseases—The Example of Sjögren's Syndrome," Proteomics, vol. 7, pp. 1634-1643, 2007.
Mar. 3, 2015 Office Action issued in U.S. Appl. No. 12/452,035.
Feb. 23, 2015 Office Action issued in U.S. Appl. No. 12/452,047.
Apr. 9, 2015 Office Action issued in U.S. Appl. No. 13/732,521.
Jul. 15, 2015 Office Action issued in U.S. Appl. No. 13/712,340.
Guo et al. "Combined Use of Positive and Negative Immunomagnetic Isolation Followed by Real-Time RT-PCR for Detection of the Circulating Tumor Cells in Patients with Colorectal Cancers." J Mol. Med., 2004, 82:768-774.
Aug. 5, 2015 Office Action issued in U.S. Appl. No. 12/452,035.
Aug. 5, 2015 Office Action issued in U.S. Appl. No. 12/452,047.
Mar. 3, 2016 Office Action Issued in U.S. Appl. No. 12/452,035.
Mar. 24, 2016 Office Action Issued in U.S. Appl. No. 14/701,002.
Mar. 3, 2016 Office Action issued in U.S. Appl. No. 12/452,047.
Dec. 31, 2015 Office Action issued in U.S. Appl. No. 13/732,521.
Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry, vol. 11, No. 5, 1992, pp. 433-444.
Harig et al., "Induction of Cytotoxic T-cell Responses Against Immunoglobulin V region-Derived Peptides Modified at Human Leukocyte Antigen-A2 Binding Residues," Blood, vol. 98, pp. 2999-3005, 2001.
Jan. 11, 2016 Office Action issued in U.S. Appl. No. 13/712,340.
Jul. 25, 2016 Office Action issued in U.S. Appl. No. 13/712,340.
Feb. 9, 2017 Office Action issued in U.S. Appl. No. 12/452,035.
Sep. 21, 2016 Office Action Issued in U.S. Appl. No. 14/701,002.
Sep. 20, 2016 Office Action issued in U.S. Appl. No. 12/452,047.
Hogle, Doreen M et al. "Quantitation of Plasma Apolipoprotein A-I Using Two Monoclonal Antibodies in an Enzyme-Linked Immunosorbent Assay." Journal of Lipid Research, vol. 29, pp. 1221-1229, 1988.
Mar. 15, 2017 Office Action issued in U.S. Appl. No. 13/712,340.
The 1000 Genomes Project Consortium. "A Map of Human Genome Variation from Population-Scale Sequencing." Nature, 2010, vol. 467, pp. 1061-1073.
Jul. 23, 2014 Office Action issued in U.S. Appl. No. 12/452,035.
Friedman et al., "Proteome Analysis of Human Colon Cancer by Two-Dimensional Difference Gel Electrophoresis and Mass Spectrometry," *Proteomics*, 2004, vol. 4, pp. 793-811.
Jul. 24, 2014 Office Action issued in U.S. Appl. No. 12/452,047.
Kozak et al., "Characterization of Serum Biomarkers for Detection of Early Stage Ovarian Cancer", *Proteomics*, 2005, vol. 5, pp. 4589-4596.
Bury et al., "Quantification of Human Serum Apolipoprotein AI by Enzyme Immunoassay", *Clinical Chemistry*, 1985, vol. 31, No. 2, pp. 247-251.
Laine, Anne, "Rocket Immunoelectrophoresis Technique or Electroimmunodiffusion", Methods in Molecular Biology, 1992, vol. 10, pp. 201-205.

\* cited by examiner

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Synthetic construct: Primer

<400> SEQUENCE: 1
atggagcagc tgagctcagc aaac                                              24

<210> SEQ ID NO 2
<211> LENGTH: 24
<212> TYPE: DNA
<213> ORGANISM: Artificial Sequence
<220> FEATURE:
<223> OTHER INFORMATION: Synthetic construct: Primer

<400> SEQUENCE: 2
ctaaggggaa gaaaatctcc ccaa                                              24

<210> SEQ ID NO 3
<211> LENGTH: 33
<212> TYPE: DNA
<213> ORGANISM: Artificial Sequence
<220> FEATURE:
<223> OTHER INFORMATION: Synthetic construct: Primer

<400> SEQUENCE: 3
cggagcgtct cccatgagtt tctccggcaa gta                                    33

<210> SEQ ID NO 4
<211> LENGTH: 49
<212> TYPE: DNA
<213> ORGANISM: Artificial Sequence
<220> FEATURE:
<223> OTHER INFORMATION: Synthetic construct: Primer

<400> SEQUENCE: 4
gaaatgcaga cttgtctaga tgcgcttgct gatgcgcttg aagacaatg                   49

<210> SEQ ID NO 5
<211> LENGTH: 22
<212> TYPE: DNA
<213> ORGANISM: Artificial Sequence
<220> FEATURE:
<223> OTHER INFORMATION: Synthetic construct: Primer

<400> SEQUENCE: 5
atggcagaca atttttcgct cc                                                22

<210> SEQ ID NO 6
<211> LENGTH: 26
<212> TYPE: DNA
<213> ORGANISM: Artificial Sequence
<220> FEATURE:
<223> OTHER INFORMATION: Synthetic construct: Primer

<400> SEQUENCE: 6
ttatatcatg gtatatgaag cactgg                                            26

<210> SEQ ID NO 7
<211> LENGTH: 64
<212> TYPE: DNA
<213> ORGANISM: Artificial Sequence
```

<220> FEATURE:
<223> OTHER INFORMATION: Synthetic construct: Primer

<400> SEQUENCE: 7
gcgaattctt taagaaggag atatacatat gacgagcaaa ggtccggaag aggagcaccc    60
atcg    64

<210> SEQ ID NO 8
<211> LENGTH: 28
<212> TYPE: DNA
<213> ORGANISM: Artificial Sequence
<220> FEATURE:
<223> OTHER INFORMATION: Synthetic construct: Primer

<400> SEQUENCE: 8
gcaagcttca gctgtcactg ggcagggc    28

<210> SEQ ID NO 9
<211> LENGTH: 424
<212> TYPE: DNA
<213> ORGANISM: Artificial Sequence
<220> FEATURE:
<223> OTHER INFORMATION: Synthetic construct: I-FABP

<400> SEQUENCE: 9
ggtaccgaat tccgcgtttg acagcacttg gaaggtagac cggagtgaaa actatgacaa    60
gttcatggaa aaaatgggtg ttaatatagt gaaaaggaag cttgcagctc atgacaattt    120
gaagctgaca attacacaag aaggaaataa attcacagtc aaagaatcaa gcgcttttcg    180
aaacattgaa gttgtttttg aacttggtgt cacctttaat tacaacctag cagacggaac    240
tgaactcagg gggacctgga gccttgaggg aaataaactt attggaaaat tcaaacggac    300
agacaatgga aacgaactga atactgtccg agaaattata ggtgatgaac tagtccagac    360
ttatgtgtat gaaggagtag aagccaaaag gatctttaaa aaggattcta gagtcgacga    420
gctc    424

<210> SEQ ID NO 10
<211> LENGTH: 31
<212> TYPE: DNA
<213> ORGANISM: Artificial Sequence
<220> FEATURE:
<223> OTHER INFORMATION: Synthetic construct: Primer

<400> SEQUENCE: 10
atgggaattc aggagcagct gagctcagca a    31

<210> SEQ ID NO 11
<211> LENGTH: 30
<212> TYPE: DNA
<213> ORGANISM: Artificial Sequence
<220> FEATURE:
<223> OTHER INFORMATION: Synthetic construct: Primer

<400> SEQUENCE: 11
cgataagctt aaggggaaga aaatctcccc    30

<210> SEQ ID NO 12
<211> LENGTH: 62
<212> TYPE: DNA
<213> ORGANISM: Artificial Sequence
<220> FEATURE:
<223> OTHER INFORMATION: Synthetic construct: Primer

```
<400> SEQUENCE: 12
gctggccatg ggcagcagcc atcatcatca tcatcacatg agtttctccg gcaagtacca    60
ac                                                                    62

<210> SEQ ID NO 13
<211> LENGTH: 39
<212> TYPE: DNA
<213> ORGANISM: Artificial Sequence
<220> FEATURE:
<223> OTHER INFORMATION: Synthetic construct: Primer

<400> SEQUENCE: 13
gcacggatcc tagatgcgct tgctgatgcg cttgaagac                            39

<210> SEQ ID NO 14
<211> LENGTH: 31
<212> TYPE: DNA
<213> ORGANISM: Artificial Sequence
<220> FEATURE:
<223> OTHER INFORMATION: Synthetic construct: Primer

<400> SEQUENCE: 14
atgggaattc aggcagacaa tttttcgctc c                                    31

<210> SEQ ID NO 15
<211> LENGTH: 34
<212> TYPE: DNA
<213> ORGANISM: Artificial Sequence
<220> FEATURE:
<223> OTHER INFORMATION: Synthetic construct: Primer

<400> SEQUENCE: 15
cgataagctt atatcatggt atatgaagca ctgg                                 34
```

METHOD FOR THE ASSAY OF LIVER FATTY ACID BINDING PROTEIN, ACE AND CA 19-9 FOR THE IN VITRO DIAGNOSIS OF COLORECTAL CANCER

The present invention relates to the cancerology field. More particularly, the subject of the present invention is a method for the in vitro diagnosis of colorectal cancer in a human patient, by determining the presence of Liver Fatty Acid-Binding Protein (L-FABP), in combination with the ACE and CA19-9 markers, in a biological sample taken from this patient, it being possible for said method to be used both for early diagnosis, screening, therapeutic follow-up and prognosis, and for relapse diagnosis in relation to colorectal cancer.

Colorectal cancer (CRC) is a major public health problem. The worldwide incidence thereof was estimated at 875 000 new cases in 1996[1]. Taking into account both sexes, it is the cancer that occurs most frequently in western countries, where it is generally classed among the first 3 most common causes of death due to cancer. The 5-year survival rate, all stages taken into account, is in the region of 60%.

Only early diagnosis offers the hope of a curative treatment. However, at the current time, there is no serological screening test nor specific diagnostic test which is early.

Screening for colorectal cancer is currently carried out in Europe with two distinct approaches: firstly, using a paraclinical test which consists in looking for the presence of blood in the stools (Faecal Occult Blood Test, FOBT, marketed, for example, under the name Hemoccult®). This technique has demonstrated its clinical usefulness. When it is used every 2 years in individuals between the ages of 50 and 74, it can reduce by 15 to 20% mortality due to colorectal cancer[2]. For this, it is necessary for more than half the population concerned to participate regularly in the screening and for a colonoscopy to be carried out in the event of a positive test, optionally followed by an appropriate treatment.

Nevertheless, this screening technique suffers from a certain number of handicaps:

The major drawback of this test is its mediocre sensitivity, most especially for adenomas (precancerous dysplastic lesion) which, if they are large in size, will result in the development of cancer in 1 case out of 10.

The test is also not very specific. The appearance of blood in the stools may be related to a nontumor condition: ulcerative colitis, hemorrhoids, fistulae, etc. In this case, an investigation by colonoscopy must be carried out, with the drawbacks described hereinafter.

Finally, Hemoccult® tests are difficult to interpret; they must therefore be read in specialized centers, by qualified competent personnel.

Immunological tests specific for human hemoglobin (Feca EIA®, Heme Select®, etc.) have also been described. They probably constitute progress compared with Hemoccult®, but they essentially exhibit the same problems. Thus, InSure™, marketed by Enterix Inc., makes it possible to detect 87% of patients suffering from CRC and 47% of those having precancerous polyps. It is a test for detecting human hemoglobin in the stools, and more particularly the globin portion of this molecule.

A second screening strategy is the systemic performing of a colonoscopy after the age of 50, which makes it possible in theory to reduce mortality due to colorectal cancer. However, the acceptability of this examination in individuals who are in good health is too low for a screening policy using endoscopy to reduce mortality (the level of compliancy for colonoscopy in European countries having set up this screening strategy is around 2%). There is a not insignificant risk (0.1%) of perforation and bleeding of the colon and of death (1/10 000), and it is also very expensive for public health. Furthermore, colonoscopy requires a very restrictive prior colonic preparation, which in large part explains the poor compliance.

Tumor markers that can be assayed by immunoassays have for a long time been described in the context of colorectal cancer. They are in particular the carcinoembryonic antigen (ACE) and CA19-9.

ACE is used for follow-up. It cannot be used for the screening or for the early diagnosis of colorectal cancer because its sensitivity and its specificity are insufficient. This is because this marker is expressed by other types of cancer, and in benign pathologies. Despite everything, it is possible to increase sensitivity without losing specificity by combining, with ACE, another tumor marker such as CA19-9 or CA72-4.

The causes of physiological variations in CA19-9 are rare, but other benign conditions (hepatobiliary conditions, pancreatic conditions), or malignant conditions may induce an increase in CA19-9. This marker, taken alone, is therefore also of no interest for diagnosis. Nevertheless, since its serum concentration is correlated with the size of the tumor and the presence of metastases, it may also enable a therapeutic follow-up or the early demonstration of relapses.

Commercially available tests have, moreover, been proposed, such as:

Colopath®/ColorectAlert$^{MD}$, marketed by Ambrilia, is a rapid and relatively noninvasive screening test for CRC. Colopath® detects a plasmalogen (class of complex lipids which are part of phospholipids) in the rectal mucus of individuals with a colorectal pathological condition, whereas ColorectAlert$^{MD}$ detects T-antigen, a complex sugar in the rectal mucus. The Colopath®/ColorectAlert$^{MD}$ test involves the application of rectal mucus to a test strip, and the positive or negative result is based on a Schiff reaction. Ambrilia has studied 1787 individuals and demonstrated that Colopath®/ColorectAlert$^{MD}$ detects 54% of cases of early-stage colorectal cancer and 49% of all stages combined.

COLARIS, marketed by Myriad Genetics, is a test for detecting, in the blood, mutations in the MLH1 and MSH2 genes for screening for hereditary nonpolyposis colon cancer (HNPCC syndrome). The result of the test is available in 3 weeks. Myriad uses the most sensitive and most specific sequencing techniques currently available. The test is expensive.

DR-70®, marketed by AMDL, is a test to screen for various types of cancer (lung, colon, breast, liver, stomach, etc.). It is not therefore specific for CRC. The principle of said test is based on the double sandwich ELISA technique (assaying of the DR-70 antigen). Revealing is carried out by enzymatic reaction (antibodies coupled to biotin and to streptavidin). A colored reaction indicates the presence of cancer.

The applicants have now demonstrated, surprisingly, that the use of the tumor marker (L-FABP), in combination with the ACE and CA19-9 markers, which are released by colonic tumors out of the cancerous tissues, such that they can be detected both in biological samples remote from the tumors and in the tumors themselves, makes it possible to substantially improve the diagnosis of colorectal cancer.

Thus, a first subject of the present invention is a method for the in vitro diagnosis of colorectal cancer by determining the presence of the Liver Fatty Acid-Binding Protein, ACE and CA19-9 markers in biological samples taken from patients suspected of having colorectal cancer, and preferably remote from the tumors.

The present invention also relates to the use of this method both for early diagnosis, screening, therapeutic follow-up and prognosis, and for relapse diagnosis in relation to colorectal cancer.

The method of the invention therefore makes it possible to diagnose colorectal cancer specifically and early by means of a simple test consisting in searching for the presence of the L-FABP, ACE and CA19-9 markers in a biological sample taken from a patient.

The determination, in a biological sample which may or may not be remote from the tumor, of the presence of the L-FABP, ACE and CA19-9 markers, the concentrations of which in this biological sample are increased relative to the reference values determined for healthy patients, then makes it possible to conclude with respect to the pathological condition sought. One of the advantages of the method of the invention therefore lies in the possibility of using a sample remote from the potential tumor as a diagnostic sample, thereby enabling a simple and noninvasive diagnosis, whereas a tissue diagnosis requires a biopsy taken invasively. In fact, the study of tissue markers, for example on a tissue section (immunohistochemistry), may be of prognostic interest, but is of no interest for screening for or diagnosing colorectal cancer.

The Liver Fatty Acid-Binding Protein marker (Swiss Prot No. P07148, also known as L-FABP, FABP1, FABPL, Z-protein or sterol transporter protein) belongs to the FABP family which comprises nine isoforms. Each isoform is named according to the tissue in which it was first detected. These isoforms have a shared function and similar three-dimensional structures, but their sequence homology is not high. L-FABP was sequenced in 1985[3]. It is a small protein of 15 kDa that is abundant in the cytosol and that has the ability to bind to free fatty acids and also to bilirubin. Some recent studies appear to indicate that impairments in expression of the L-FABP protein could induce a tumorigenesis process. For prostate cancer, the level of expression of L-FABP mRNAs in tumor tissue biopsies was 10 times higher than in the normal tissue[4]. For colon cancer, several teams have identified a decrease in the expression of L-FABP protein in the tumor tissue compared with normal colonic mucosa, using 2-dimensional electrophoresis techniques[5]. This result has also been confirmed by immunohistochemistry techniques. In addition, the L-FABP protein is a prognostic liver resection marker in patients with colorectal cancer having metastasized to the liver[6].

The assaying of ACE (carcinoembryonic antigen) for the diagnosis of colorectal cancer has been proposed since 1965 by P. Gold and S. Freedman[7], but an assay for this marker in the blood has poor sensitivity for the diagnosis of colorectal cancers at a relatively nonadvanced stage. The assaying of serum ACE is thus especially recommended for evaluating the risk of liver metastases[8] and for therapeutic follow-up. In addition, it is a marker that is not very specific for colorectal cancer; it may in fact be increased in many other cancers (lung, breast, etc.). On the other hand, the assaying of fecal ACE appears to be more sensitive and more specific than the assaying of serum ACE or than the assaying of fecal blood[9]. However, this assaying is not yet proposed routinely.

The reactive antigenic determinants 1116-NS-19-9, more commonly called CA19-9 (carbohydrate antigen 19.9), are carried by high-molecular-weight proteins[10]. The assaying of CA 19-9 in the blood is more specific than that of ACE. The CA 19-9 level in the blood increases in the event of colorectal cancer, of pancreatic cancer and of liver cancer (cholangiocarcinoma), but also in the event of noncancerous pathological conditions (cholangitis, etc.). Its use in combination with ACE is recommended both at the time of diagnosis of a cancer and for follow-up of the pathological condition.

The expression "determining the presence of a tumor marker" is intended to mean determining the presence of the protein or of its messenger RNA, or detecting a modification on its gene in the coding or noncoding sequences, such as methylations.

The expression "release by colonic tumors" is intended to mean the active or passive secretion or the release, whatever the mechanism, of the tumor marker by the tumor cells themselves or by the neighboring nontumor cells following lesions or modifications of cell phenotype resulting from the tumor development.

The expression "biological sample in which the method of the invention is carried out" is intended to mean any biological sample capable of containing the tumor marker of interest. By way of example of a biological sample not remote from the tumor, mention may be made of solid samples such as the tissue originating from the tumor, from biopsies of this tumor, from lymph nodes or from metastases of the patient, and cells purified from these solid samples. By way of example of a biological sample remote from the tumor, mention may be made of biological fluids such as whole blood or derivatives thereof, for example serum or plasma, urine, saliva and effusions, bone marrow and stools, and cells purified from these liquid samples. Blood or derivatives thereof and also stools, effusions and cells purified from these liquid samples are preferred.

The method of the invention may be improved by detecting, in addition to L-FABP, ACE and CA19-9, where appropriate also released by colonic tumors out of the cancerous tissues. Thus, the combination of at least four markers makes it possible to improve the specificity and the sensitivity of the test for the diagnosis of colorectal cancer.

Thus, another subject of the invention also consists in determining the presence of at least one other tumor marker chosen from the following two groups of markers, considered alone or in combination:

group A: Leukocyte Elastase Inhibitor, Ezrin, Aminoacylase 1, Intestinal Fatty Acid-Binding Protein, Apolipoprotein AI, Apolipoprotein AII, Galectin-3 and I-Plastin, some of these markers being new markers identified by the applicant, group B: markers having an additional diagnostic interest, namely: Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Keratin type II Cytoskeletal 8, Keratin type I Cytoskeletal 18, Keratin type I Cytoskeletal 19, Epithelial Cadherin, Villin, CA 242, CA 50, CA 72-2, Testosterone, TIMP-1, Cripto-1, Intelectin-1, Protein Disulfide Isomerase, Cytokeratin 20, Translationally-Controlled Tumor Protein, (Pro) defensin-A5, the detection of DNA fragments in the blood having specific alterations to their methylation profile, for instance methylated DNA of the AXL4 gene (aristaless-like homeobox-4 gene methylation) or the methylated DNA of the septin-9 gene, the detection of specific alterations in fecal DNA fragments, such as specific mutations of fecal DNA or specific alterations of the methylation profile of fecal DNA, the detection of human fecal hemoglobin.

The method of the invention may therefore be improved by detecting at least four markers, the minimum three markers being L-FABP, ACE and CA19-9, and the other being another tumor marker chosen from group A, namely Leukocyte Elastase Inhibitor, Ezrin, Aminoacylase 1, Intestinal Fatty Acid-Binding Protein, Apolipoprotein AI, Apolipoprotein AII, Galectin-3 and I-Plastin.

The "newly described tumor marker" is intended to mean the protein or the messenger RNA or specific modifications of the corresponding gene, such as mutations or methylations.

The Leukocyte Elastase Inhibitor tumor marker (Swiss Prot No. P30740, also known as LEI, Serpin B1, Monocyte/neutrophil elastase inhibitor, M/NEI or EI) was sequenced in 1992[11]. LEI specifically inhibits proteases having elastase-type or chymotrypsin-type properties by formation of a complex that cannot be dissociated under the action of SDS[12]. LEI thus inhibits three of the major proteases produced by neutrophils: Leukocyte Elastase, Proteinase-3 and Cathepsin G. These proteases enable the immune system to defend the organism by proteolysis of extracellular or phagocytosed substrates. However, when these proteases are in excess, they are responsible for inflammatory reactions. LEI could therefore have a role in regulating and limiting the inflammatory action induced by cell proteases. The applicant has shown, for its part, surprisingly, that this protein is a good marker in biological samples taken from a patient having colorectal cancer, said samples possibly being remote from the tumor.

The Ezrin marker (Swiss Prot No. P15311, also known as p81, Cytovillin or Villin-2) is a protein which provides binding between the cell membrane and the Actin filaments of the cytoskeleton of the cell, in particular in the microvilli of intestinal epithelial cells[13]. W. G. Jiang and S. Hiscox[14] have shown that the Interleukins IL-2, IL-8, IL-10, etc. can inhibit the expression of ezrin in the HT29 human colorectal cancer cell line. The same authors[15] have shown that the inhibition of Ezrin expression in the HT115 and HRT18 colorectal cancer cell lines reduces the adhesion between cells and increases the mobility and the invasive behavior of the cells. They have concluded that Ezrin regulates cell/cell and cell/matrix adhesions by interacting with the cell adhesion molecules E-Cadherin and beta-Catenin. They have suggested that Ezrin could play an important role in controlling the invasive potential of cancer cells. Moreover, T. Xiao et al.[16] have used an ELISA assay to quantify the plasma Ezrin of patients with lung cancer. However, they have not observed any differences compared with control individuals. The applicant has shown, for its part, surprisingly, that this protein is a good marker in biological samples taken from a patient having colorectal cancer, said samples being remote or not from the tumor.

The Aminoacylase 1 marker (Swiss Prot No. Q03154, also known as EC 3.5.1.14, N-Acyl-L-Amino Acid Amidohydrolase or ACY-1) is part of the Aminoacylase family. They are enzymes which catalyze the hydrolysis of acylated amino acids so as to give fatty acids and amino acids[17]. An immunochemical assay for Aminoacylase enzymatic activity was developed as early as 1975 by K. Lorentz et al.[18] and was used to assay various tissues and sera[19]. The study showed an increase in Aminoacylase activity in the case of hepatic pathological conditions but not in the case of colon cancer. Moreover, the Aminoacylase 1 gene has been identified on chromosome 3p21.1[20]. The 3p21.1 region is reduced to homozygosity in a small cell lung cancer, and in this case, the Aminoacylase expression is repressed or undetectable[21]. Similarly, S. Balabanov et al.[22] have shown that the Aminoacylase expression is repressed in the case of kidney cancer. The applicant has shown, for its part, surprisingly, that this protein is a good marker in biological samples taken from a patient having colorectal cancer, said samples being remote or not from the tumor.

The Intestinal Fatty Acid-Binding Protein marker (Swiss Prot No. P12104, also known as I-FABP, FABP-2 or FABPI) was sequenced in 1987[23]. It is a small protein of 15 kDa that is abundant in the cytosol and that has the ability to bind to free fatty acids and also to bilirubin. The I-FABP protein is expressed in the enterocytes of the small intestine and may constitute approximately 2% of the protein content of this cell type. At the tissue level, the duodenum and the jejunum contain significantly higher amounts of I-FABP than the colon (jejunum: 4.8 µg/g, colon: 0.25 µg/g)[24]. I-FABP could not be detected in the plasma samples of healthy individuals. On the other hand, in certain pathological contexts such as intestinal ischemia, Crohn's disease or primary biliary cirrhosis, it is possible to demonstrate an increase in the plasma I-FABP concentration in certain individuals[24]. For prostate cancer, it has been shown that the level of expression of I-FABP mRNA in biopsies of tumor tissue is 7 times higher than in normal tissue[20]. In the model of induction of a colorectal tumor with azoxymethane in the rat, the level of expression of I-FABP mRNA is reduced by 2.92 to 3.97 times when the animals have a diet that reduces the incidence of cancer (soya proteins or whey hydrolysate)[25]. The applicant has shown, for its part, surprisingly, that this protein is a good marker in biological samples taken from a patient having colorectal cancer, said samples being remote from the tumor.

The Apolipoproteins are a family of proteins constituted of polar amino acids, which allow the transport of lipids in the blood by formation of a hydrophilic macromolecular complex called a lipoprotein. For each of the human plasma Apolipoproteins, there are isoforms derived from genetic polymorphism and/or from post-translational modifications, the presence of which in the blood can be associated with certain pathological conditions[26]. The plasma concentration of Apolipoproteins is not insignificant, of the order of those mg/ml[27].

The Apolipoprotein AI marker (NCBI No. 490098, also known as Apo A-I, Apo AI and Apo A1) is a protein of 243 amino acids and of 28 kDa. It is essentially synthesized by the liver and the intestine. This protein has been shown to be underabundant in the sera of patients suffering from colorectal cancer compared with healthy individuals, by SELDI-TOF[28]. However, it is specified in this article that patients with CRC are distinguished from healthy individuals by combining Apo AI with other protein markers. Moreover, this article specifies that the assaying of Apo AI by turbidimetric immunoassay, carried out by another team, does not confirm the underabundance of this protein in the sera of patients having CRC[29]. Hachem et al.[30] have, for their part, assayed Apo AI in sera of patients having had liver cancer following colorectal cancer metastases. The applicant has shown, for its part, surprisingly, that assaying by immunoassay makes it possible to demonstrate a decrease in the concentration of this protein in patients having colorectal cancer, contrary to what was put forward by Engwegen et al.[28], who were able to demonstrate this decrease only by implementing the SELDI-TOF technique. The assaying of Apo AI by immunoassay in biological samples is a good method for the diagnosis of colorectal cancer, said samples being remote from the tumor, insofar as the assaying by immunoassay that is carried out is not turbidimetry as used by the team of Zhang et al.[29].

The Apolipoprotein AII marker (Swiss Prot No. P02652, also known as ApoA II, Apo-AII and Apo A2) is a 17380-Da protein composed of two polypeptide chains of 77 amino acids each, linked by a disulfide bridge. Like Apolipoprotein AI, Apolipoprotein AII is essentially synthesized by the liver and the intestine. Hachem et al.[30] have also assayed, in addition to Apo AI, Apo AII in sera of patients having had liver cancer following colorectal cancer metastases. However, the results are not significant and do not enable a conclusion to be drawn as to the pathological condition sought. The applicant has shown, for its part, surprisingly, that the decrease in the concentration of this protein in patients having colorectal cancer makes it a good marker in biological samples taken from a patient having colorectal cancer, said samples being remote from the tumor.

The I-Plastin marker (Swiss Prot No. Q14651, also known as intestine-specific Plastin or Plastin 1) belongs to the family of human Plastins of which three representatives are known: I-Plastin, L-Plastin and T-Plastin. Some authors call Plastins "Fimbrins", yet other authors reserve the name Fimbrin for I-Plastin. The Plastins are proteins that bind to Actin so as to form the cytoskeleton (cell skeleton). They are 70 kDa proteins that are relatively well-conserved throughout eukaryotic evolution. They exhibit strong tissue specificity, only one isoform at a time is present in normal tissues[31]. The use of Plastins with respect to cancer has already been described in U.S. Pat. No. 5,360,715, which proposes a method for determining whether a cell is hematopoietic or neoplastic i.e. cancerous. This method claims the assaying of L-Plastin and of T-Plastin at the cellular level, and more particularly the assaying of the mRNA thereof. However, despite these properties, no prior study has been carried out to evaluate the importance of Plastins in relation to the diagnosis of colorectal cancer using a serum or stool sample. Furthermore, I-Plastin has never even been envisioned as a potential cancer marker[32]. The applicant has shown, for its part, surprisingly, that this protein is a good marker in biological samples taken from a patient having colorectal cancer, said samples being remote or not from the tumor.

The Galectin-3 marker (Swiss Prot No. P17931, also known as Gal-3, Galactose-Specific Lectin 3, MAC-2 antigen, IgE-Binding Protein, 35 kDa Lectin, Carbohydrate Binding Protein 35, CBP 35, Laminin-Binding Protein, Lectin L-29, L-31, Galactoside-Binding Protein or GALBP) is a lectin capable of binding to beta-galactoside structures of N-acetyllactosamine type. It is a protein with multiple functions involved in various biological functions, including the adhesion of tumor cells, proliferation, differentiation, angiogenesis, apoptosis, metastatic cancer progression[33]. Various studies have shown that Gal-3 can form complexes with numerous molecules: ACE, IgE, Laminin, Mucin, Mac-2BP, LAMP1, LAMP2, Fibronectin, etc. A serum assay of Gal-3 has been described by I. Iurisci et al.[34]. Gal-3 was captured on microplates coated with Mac-2-binding protein (a Gal-3-binding protein) and then revealed with an anti-Gal-3 rat antibody. This study showed elevated serum of Gal-3 in the case of gastrointestinal cancers, breast cancer, lung cancer, ovarian cancer, melanomas and non-Hodgkin lymphomas.

The concentration of the tumor marker chosen from group A will, depending on the marker under consideration, be increased or decreased in the biological sample in which the method of the invention is carried out, compared with the reference values determined for the healthy patients.

The method of the invention may also be improved by combining the detection of the L-FABP, ACE and CA19-9 markers and of one other tumor marker chosen from group B, namely: the markers Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Keratin type II Cytoskeletal 8, Keratin type I Cytoskeletal 18, Keratin type I Cytoskeletal 19, Epithelial Cadherin, Villin, CA 242, CA 50, CA 72-2, Testosterone, TIMP-1, Cripto-1, Intelectin-1, Protein Disulfide Isomerase, Cytokeratin 20, Translationally Controlled Tumor Protein, (Pro)defensin-A5, the detection of DNA fragments in the blood having specific alterations to their methylation profile, for instance methylated DNA of the AXL4 gene (aristaless-like homeobox-4 gene methylation) or methylated DNA of the septin-9 gene, the detection of specific alterations in fecal DNA fragments, such as specific mutations of fecal DNA or specific alterations of the methylation profile of fecal DNA, and the detection of human fecal hemoglobin. Of course, the method of the invention may also implement the detection, in the same assay, of LEI, of at least one tumor marker chosen from group B and of at least one other tumor marker chosen from group A.

The Beta2-Microglobulin marker (Swiss Prot No. P61769, also known as β2-Microglobulin, β2M) is a low-molecular-weight (11 to 12 kDa) protein found at the surface of most nucleated human cells. The serum β2-Microglobulin level increases in certain patients suffering from cancer, without this increase being specific, or correlated with the nature of the tumor, its stage or the severity of the disease. A significant increase is also observed in other diseases, such as lupus erythematosus, rheumatoid arthritis, Sjögren's syndrome, malignant diseases of the lymphoid system (multiple myeloma, B-cell lymphoma), certain viral diseases (hepatitis or AIDS), and in hemophiliac patients. Since β2-Microglobulin is filtered by the renal glomeruli and reabsorbed by the proximal convoluted tubules, its concentration in the blood may be modified in the case of renal pathological conditions. The assaying of β2-Microglobulin is thus most commonly reserved for the diagnosis of renal pathological conditions, or for the follow-up of infection with the acquired immunodeficiency virus. However, this marker is known as a tumor marker, in particular for colon cancer.

The Proteasome 20S marker (also known as Prosome) is the central structure of the proteasome, which is itself a molecular complex responsible for the intracellular degradation of ubiquitinated proteins[35]. The Proteasome is a molecular complex of 700 kDa, constituted of 28 subunits associated in 4 rings of 7 subunits. In humans, 7 alpha units (α1, α2, α3, α4, α5, α6 and α7) and 10 beta units (β1, β2, β33, β4, β5, β6, β7, β1i, β2i and β5i) are known. By virtue of its catalytic properties, the Proteasome plays a central role in the mechanisms of cell proliferation, growth, regulation and apoptosis, and therefore in the cancerization pathways. Proteasome inhibition with Bortezomib (Velcade) is a recognized treatment for multiple myeloma. Phase II or III therapeutic trials are ongoing for hematological cancers or tumors. T. Lavabre-Bertrand et al.[36] have shown that the serum level of Proteasome can increase on the occasion of certain pathological conditions, in particular in the case of cancers (myeloma, lymphoma and solid tumors).

The L-Lactate Dehydrogenase Chain B marker (Swiss Prot No. P07195, also known as LDH-B, LDH Heart Unit or LDH-H) is a protein that can form complexes in the form of homotetramers. This protein can also form complexes with the L-Lactate Dehydrogenase Chain A protein (Swiss Prot No. P00338, also known as LDH-A, LDH muscle unit or LDH-M) in the form of heterotetramers. The serum dose and/or the serum enzymatic activity of the tetrameric complexes, called LDH, increase(s) in the bloodstream proportionally to the tumor mass for many solid tumors. Its use is recommended in combination with human chorionic gonadotrophin (beta-hCG) and placental alkaline phosphatase for the follow-up of seminal vesicle cancers. LDH is considered to be a marker of importance for the prognosis of lymphomas, of leukemia and of colon cancer[37].

The Calreticulin marker (Swiss Prot No. P27797, also known as CRP55, Calregulin, HACBP, ERp60 or grp60) is a multifunctional protein. It is a lectin capable of interacting transiently with virtually all the monoglycosylated proteins of the endoplasmic reticulum. D. J. McCool et al.[38] have thus shown that Calreticulin is involved in maturation of the colonic mucin MUC2. A method for the diagnosis of CRC which uses assaying of Calreticulin in a tissue, the stools or a body fluid is described in patent application WO 03/065003.

The Regenerating Islet-Derived Protein 3 Alpha marker (Swiss Prot No. Q06141, also known as Reg III-alpha, Pancreatitis-Associated Protein 1 or Pancreatis Associated Protein I (PAP 1)) is a protein that is weakly expressed in the healthy pancreas. It is overexpressed during the acute phases of pancreatitis and in certain patients suffering from chronic pancreatitis. In this case, it appears in the pancreatic fluid and in the bloodstream[39]. Y. Motoo et al.[40] have shown, by ELISA assay, that the level of PAP 1 in the blood increases in certain patients having colon cancer, stomach cancer, liver cancer or pancreatic cancer, and also in the case of renal insufficiency. To to this, they used the ELISA assay (PAN-CEPAP) marketed by the company Dynabio (La Gaude, France).

The Tumor-Associated Calcium Signal Transducer 1 marker (Swiss Prot No. P16422, also known as Major gastrointestinal tumor associated protein GA733-2, Epithelial cell surface antigen, EpCAM, Epithelial glycoprotein, EGP, Adenocarcinoma-associated antigen, KSA, KS 1/4 antigen, Cell surface glycoprotein Trop-1 or CD326 antigen), was characterized in 1979 by virtue of its ability to be recognized by an antibody directed against colorectal cancer cells[41]. This protein is known by various names, as indicated above, but the most common use is to call it EpCAM. It is a transmembrane protein expressed at the basolateral surface of cells, in certain epithelia and many cancers[42]. As early as 1982, Herlyn et al.[43] showed that the injection of an anti-EpCAM monoclonal antibody could inhibit tumor growth in patients having colorectal cancer. These results resulted in the development of an antitumor treatment based on an anti-EpCAM antibody called Edrecolomab. This treatment is marketed under the name Panorex™. Moreover, H. Abe et al.[44] have shown, by ELISA assay, that a soluble form of EpCAM, called MK-1, is increased in the bloodstream in 10% of cancer patients studied.

The Cytokeratins are part of the proteins that make up the intermediate filaments of the cytoskeleton of epithelial cells. Currently, more than 20 human Cytokeratins have been identified. The Cytokeratins 8 (Swiss Prot No. P05787, also known as Cytokeratin-8, CK-8, Keratin-8 or K8), 18 (Swiss Prot No. P05783, also known as Cytokeratin-18, CK-18, Keratin-18 or K18) and 19 (Swiss Prot No. P08727, also known as Cytokeratin-19, CK-19, Keratin-19 or K19) are the most abundant in epithelial cells and are useful tools for the diagnosis of cancer pathologies[45]. This clinical importance is linked to the release of Cytokeratins by epithelial cells in the apoptotic or proliferation phase. In the case of apoptosis, this release occurs in the form of soluble fragments which seem to appear under the proteolytic action of caspases. Undegraded Cytokeratin forms have never been described in the bloodstream. The three Cytokeratin assays most commonly used clinically are the tissue polypeptide antigen (TPA) assay, the tissue polypeptide specific antigen (TPS) assay and the CYFRA 21-1 assay. TPA is a broad-spectrum test which measures Cytokeratins 8, 18 and 19. The TPS and CYFRA 21-1 assays are more specific and measure, respectively, fragments of Cytokeratin 18 and of Cytokeratin 19. These 3 assays detect soluble Cytokeratin fragments that may be present on their own or in the form of protein complexes. TPA, TPS or CYFRA-21-1 have been used for the therapeutic follow-up of colorectal cancers, breast cancers, lung cancers, bladder cancers, ovarian cancers, pancreatic cancers, prostate cancers and certain ENT cancers. The assaying of soluble Cytokeratin fragments in the blood in fact has a clinical value in screening for relapses or evaluating the response to the therapy used (radiotherapy, chemotherapy, hormone treatment). Regular assaying makes it possible in particular to evaluate the progression of the tumor mass. The amount of soluble blood Cytokeratins also has a prognostic aspect with respect to the tumor stage and to the formation of metastases. Currently, the blood assay for Cytokeratin that is most commonly used is CYFRA 21-1. It is highly recommended for the follow-up of patients having non-small cell lung cancer. Various commercially available assays exist for TPA (AB Sangtec Medical Co., Byk-Roland, etc.), TPS (IDL Biotech AB, BEKI Diagnosiss, etc.) and CYFRA-21-1 (Roche Diagnosiss, CIS Bio-International, Fujirebio Diagnosiss, etc.). Moreover, H. Kim et al.[46] have shown that assaying fecal Cytokeratin 19 (DiNonA Inc.) may be useful in screening for gastrointestinal diseases, in combination with a fecal occult blood assay. Finally, the use of Cytokeratin 20 (Swiss Prot No. P35900, also known as Keratin, type I Cytoskeletal 20, CK-20, Keratin-20, K20, or IT protein) as a marker in colorectal cancer is described in patent application US 2002/0160382.

The Epithelial Cadherin marker (Swiss Prot No. P12830, also known as E-Cadherin, Uvomorulin, Cadherin-1, CAM 120/80 or CD324 antigen) is a transmembrane protein that mediates calcium-dependent cell adhesion. It is specifically expressed in epithelial cells, where it is involved in maintaining their phenotype. The cytoplasmic domain of E-Cadherin binds to β-Catenin, which is itself bound to the actin filament networks of the cytoskeleton. This E-Cadherin/β-Catenin binding plays an essential role in stabilizing cell/cell adhesions of the epithelial tissue. The loss of E-Cadherin can therefore reduce cell adhesion and increase the invasive capacity of cancer cells. A reduction in expression of E-Cadherin or of β-Catenin is generally associated with greater aggressiveness and dedifferentiation of the tumor, in particular with respect to gastrointestinal cancers. F. Roca et al.[47] have thus shown that patients having colorectal cancer and underexpressing E-Cadherin have a more unfavorable prognosis than patients having a normal expression level. As early as 1983, Damsky et al.[48] showed that a soluble form of E-Cadherin could be released by the MCF-7 breast cancer cell line. This soluble form corresponds to the cleavage of the extracellular portion of E-Cadherin. Later, M. Katayama et al.[49] showed that the soluble form of E-Cadherin could be released into the bloodstream in the case of cancer, and C. Willmanns et al.[50] showed that the increase in the amount of E-Cadherin in the blood is correlated with the tumor stage in colorectal cancers. A commercially available kit is, moreover, proposed by the company Takara BioChemicals (Tokyo, Japan).

J. Holmgren et al.[51] have shown that the amount of CA 50 antigen in the serum is increased in the case of colorectal cancer. The CA 50 antigen is defined by its ability to be recognized by a specific monoclonal antibody.

As regards the CA 72 marker, T. L. Klug et al.[52] have shown that the amount of CA 72 antigen in the serum is increased in the case of colorectal cancer. The CA 72 antigen is defined by its ability to be recognized by a specific monoclonal antibody.

Similarly, P. Kuusela et al.[53] have shown that the amount of CA 242 antigen in the serum is increased in the case of colorectal cancer. The CA 242 antigen is defined by its ability to be recognized by a specific monoclonal antibody.

The assaying of Testosterone for the diagnosis of colorectal cancer has been proposed in men by M. Holland et al.[54]. These authors have shown a fall in the blood Testosterone level in the case of colorectal cancer.

As regards the TIMP-1, or tissue inhibitor of matrix metalloproteinase type-1, marker, patent application US 2007/0020707 describes in particular the assaying of TIMP-1 for the diagnosis of colorectal cancer by assaying in a body fluid.

F. Model et al.[55] showed, in July 2006, during the World Congress on Gastrointestinal Cancer, that it was possible to detect methylated forms of the septin-9 gene in the plasma of patients having colorectal cancer.

M. P. Ebert et al.[56] have shown that the ALX4 gene, or aristaless-like homeobox-4 gene, is more often methylated in the sera of patients having colorectal cancer than in control sera (P<0.0001). Using a threshold value of 41.4 pg/mL, they have obtained a sensitivity of 83.3% and a specificity of 70%.

Villin is described as a blood marker for the diagnosis of colorectal cancer in patent application FR2581456.

C. Bianco et al.[57] have shown that the amount of Cripto-1 in the serum is increased in the event of colorectal cancer.

The assaying of Intelectin-1 (Swiss Prot No. Q8WWA0, also known as Intestinal lactoferrin receptor, Galactofuranose-binding lectin, Endothelial lectin HL-1 or Omentin) for the diagnosis of colorectal cancer has been described in patent application US 2003/0082533.

The use of Protein Disulfide Isomerase (Swiss Prot No. P07237, also known as EC 5.3.4.1, PDI, Prolyl 4-hydroxylase subunit beta, Cellular thyroid hormone-binding protein or p55), of Translationally-Controlled Tumor Protein (Swiss Prot No. P13693, also known as TCTP, p23, Histamine-releasing factor, HRF or Fortilin) and of (Pro)defensin-A5 (Swiss Prot No. Q01523), as markers in colorectal cancer, is described respectively in patent applications EP1724586, US 2003/0172388 and US 2006/0179496. The term "(Pro)defensin" is intended to mean the precursor, namely the Prodefensin before cleavage, the propeptide, namely the N-terminal moiety after cleavage of the Prodefensin, and the mature protein, namely Defensin, corresponding to the C-terminal moiety after cleavage.

Finally, the assaying of human fecal hemoglobin is known practice and can be implemented as previously described.

The concentration of the tumor marker chosen from group B will, depending on the marker under consideration, be increased or decreased in the biological sample in which the method of the invention is carried out, compared with the reference values determined for healthy patients.

Preferably, the tumor marker(s) of group B is (are) chosen from: the markers: Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Epithelial-Cadherin, Testosterone, TIMP-1, Intelectin-1, Protein Disulfide Isomerase, Cytokeratin 20, Translationally-Controlled Tumor Protein, (Pro)defensin-A5, and detection of human fecal hemoglobin.

Of course, the method of the invention may also include the detection of any other marker for colorectal cancer that is known to those skilled in the art.

In one embodiment of the invention, the combinations comprising at least the following markers are preferred:
L-FABP, ACE, CA19-9 and Galectin-3,
L-FABP, ACE, CA19-9 and Apolipoprotein AI,
L-FABP, ACE, CA19-9 and Leukocyte Elastase Inhibitor,
L-FABP, ACE, CA19-9, Leukocyte Elastase Inhibitor and Aminoacylase 1,
L-FABP, ACE, CA19-9, Leukocyte Elastase Inhibitor, Aminoacylase 1, Beta2-Microglobulin, Proteasome 20S, PAP and E-Cadherin, or
L-FABP, ACE, CA19-9, Leukocyte Elastase Inhibitor, Aminoacylase 1, Beta2-Microglobulin, Proteasome 20S, Galectin-3 and Apolipoprotein AI.

As indicated above, the tumor marker(s) of interest is (are) detected in the form of a protein, or in the form of a messenger RNA, or by alteration of the corresponding DNA (mutation or modification of methylations).

The determination of the presence, in the biological sample, of the "protein" tumor marker of interest can be carried out by any method for determining the presence of a protein in a sample, known to those skilled in the art, such as, for example, a biochemical test, including an immunoassay, or by mass spectrometry.

The biochemical test may be any test widely known to those skilled in the art involving molecular interactions, i.e. reactions between said tumor marker and one or more binding partner(s) specific or not specific for said tumor marker.

Preferably, the biochemical test is an immunoassay known to those skilled in the art, involving immunological reactions between the tumor marker, which is the antigen, and one or more specific binding partner(s), namely the antibodies directed against this antigen.

The binding partners specific or not specific for the tumor marker(s) sought in the method of the invention are any partner capable of binding to this or these marker(s). They are said to be specific when they are capable of binding to these markers with a high specificity, or even a specificity of 100%. They are said to be nonspecific when their specificity of binding to these markers is low and they are then capable of binding to other ligands, such as proteins. By way of example, mention may be made of antibodies, antibody fractions, receptors and any other molecule capable of binding to this marker.

The binding-partner antibodies are, for example, either polyclonal antibodies or monoclonal antibodies.

The polyclonal antibodies may be obtained by immunization of an animal with the tumor marker concerned, followed by recovery of the desired antibodies in purified form, by taking the serum from said animal, and separation of said antibodies from the other serum constituents, in particular by affinity chromatography on a column to which an antigen specifically recognized by the antibodies, in particular said marker, is attached.

The monoclonal antibodies can be obtained by the hybridoma technique, the general principle of which is recalled hereinafter.

Firstly, an animal, generally a mouse, is immunized with the tumor marker of interest, the B lymphocytes of said animal then being capable of producing antibodies against said antigen. These antibody-producing lymphocytes are subsequently fused with "immortal" myeloma cells (murine in the example) so as to produce hybridomas. Using the heterogeneous mixture of cells thus obtained, a selection of cells capable of producing a particular antibody and of multiplying indefinitely is then carried out. Each hybridoma is multiplied in the form of a clone, each resulting in the production of a monoclonal antibody of which the properties of recognition with respect to said tumor marker may be tested, for example, by ELISA, by one-dimensional or two-dimensional Western blot, by immunofluorescence, or by means of a biosensor. The monoclonal antibodies thus selected are subsequently purified, in particular according to the affinity chromatography technique described above.

The monoclonal antibodies may also be recombinant antibodies obtained by genetic engineering, by means of techniques well known to those skilled in the art.

Examples of anti-Leukocyte Elastase Inhibitor antibodies are known and are available in particular in the Abcam catalog, rabbit anti-LEI polyclonal antibody, Cat. No. Ab47731. An anti-LEI monoclonal antibody, clone ELA-1, has been described in the article by Yasumatsu et al.[58].

Examples of anti-Ezrin antibodies are known and are available in particular in the Abcam catalog, anti-Ezrin monoclonal antibody, clone 3C12, Cat. No. Ab4069 and rabbit anti-Ezrin polyclonal antibody, Cat. No. Ab47418.

Examples of anti-Aminoacylase 1 antibodies are known and are available in particular in the Abnova catalog, anti-Aminoacylase 1 monoclonal antibody, clone 4F1-B7, Cat. No. H00000095-M01, and in the Abcam catalog, chicken anti-Aminoacylase 1 polyclonal antibody, Cat. No. Ab26173.

Examples of anti-Liver Fatty Acid-Binding Protein antibodies are known and are available in particular in the Abcam catalog, anti-L-FABP monoclonal antibody, clone 6B6, Cat. No. Ab10059, and rabbit anti-L-FABP polyclonal antibody, Cat. No. Ab7807.

Examples of anti-Intestinal Fatty Acid-Binding Protein antibodies are known and are available in particular in the R&D Systems catalog, anti-I-FABP monoclonal antibody, clone 323701, Cat. No. MAB3078, and in the Abcam catalog, rabbit anti-1-FABP polyclonal antibody, Cat. No. Ab7805.

Examples of anti-Apolipoprotein AI antibodies are known and are available in particular in the Biodesign Meridian Life Sciences catalog, anti-Apo AI monoclonal antibody, clone 4A90, Cat. No. H45402M and goat anti-Apo AI polyclonal antibody, Cat. No. K45252P.

Examples of anti-Apolipoprotein AII antibodies are known and are available in particular in the US Biological catalog, anti-Apo AII monoclonal antibody, clone 1402, Cat. No. A2299-31C and in the Biodesign Meridian Life Sciences catalog, goat anti-Apo AII polyclonal antibody, Cat. No. K74001P.

Examples of anti-I-Plastin polyclonal antibodies are known and are available in particular in the Santa Cruz Biotechnology catalog. The rabbit polyclonal antibody H-300 (Cat. No. sc-28531) reacts with I-Plastin, L-Plastin and T-Plastin. The applicant has developed monoclonal antibodies directed against I-Plastin.

Examples of anti-Beta2-Microglobulin, anti-ACE, anti-CA19-9 and anti-Testosterone antibodies are known and are in particular used in the applicant's assay kits, respectively Vidas® β2-Microglobulin, Vidas® ACE, Vidas® CA19-9™ and Vidas® Testosterone.

Examples of anti-Proteasome 20S antibodies are known and are available in particular in the Affinity Research Products catalog.

Examples of anti-Galectin-3, anti-L-Lactate Dehydrogenase Chain B, anti-Calreticulin, anti-Tumor-Associated Calcium Signal Transducer 1, anti-Keratin type II Cytoskeletal 8, anti-Keratin type I Cytoskeletal 18, anti-Keratin type I Cytoskeletal 19, anti-Epithelial-Cadherin, anti-Villin and anti-TIMP-1 antibodies are known and are available in particular in the Abcam catalog.

Examples of anti-Regenerating Islet-Derived Protein 3 Alpha antibodies are known and are in particular used in the Dynabio assay kits (La Gaude, France).

Examples of anti-CA 242, anti-CA 50 and anti-CA 72-4 antibodies are known and are available in particular in the Fujirebio catalog.

Examples of anti-Intelectin-1 antibody are known and are available in particular in the Alexis Biochemicals catalog, anti-Intelectin-1 monoclonal antibody, clone Saly-1, Cat. No. ALX-804-850-C100 and rabbit anti-Intelectin-1 polyclonal antibody, Cat. No. ALX-210-941.

Examples of anti-Protein Disulfide Isomerase antibodies are known and are available in particular in the Abcam catalog, anti-PDI monoclonal antibody, clone RL77, Cat. No. Ab5484 and rabbit anti-PDI polyclonal antibody, Cat. No. Ab3672.

Examples of anti-Cytokeratin 20 antibodies are known and are available in particular in the Abcam catalog, anti-Cytokeratin 20 monoclonal antibody, clone Ks20.8, Cat. No. Ab962 and rabbit anti-Cytokeratin 20 polyclonal antibody, Cat. No. Ab36756.

Examples of anti-TCTP antibodies are known and are available in particular in the Abnova catalog, anti-TCTP monoclonal antibody, clone 3C7, Cat. No. 157H00007178-M01 and anti-TCTP polyclonal antibody, Cat. No. 157H00007178-A01.

Examples of anti-Defensin-A5 antibodies are known and are available in particular in the Santa Cruz Biotechnology catalog, anti-Defensin-A5 monoclonal antibody, clone 8C8, Cat. No. sc-53997 and in the Alpha Diagnosis International Inc. catalog, rabbit anti-Defensin-A5 polyclonal antibody, Cat. No. HDEFA51-A.

The binding partners which are specific or not specific for the tumor marker(s) sought in the method of the invention may be used as a capture reagent, as a detection reagent or as capture and detection reagents.

The visualization of the immunological reactions, i.e. of the tumor marker/binding partner binding, may be carried out by any means of detection, such as direct or indirect means.

In the case of direct detection, i.e. without the involvement of a label, the immunological reactions are observed, for example, by surface plasmon resonance or by cyclic voltammetry on an electrode bearing a conductive polymer.

The indirect detection is carried out by means of labeling, either of the "revealing reagent" binding partner, or of the tumor marker of interest itself. In the latter case, this is then described as a competition method.

The term "labeling" is intended to mean the attachment of a label reagent capable of directly or indirectly generating a detectable signal. A nonlimiting list of these label reagents comprises:

enzymes which produce a signal that can be detected, for example, by colorimetry, fluorescence or luminescence, such as horseradish peroxydase, alkaline phosphatase, β-galactosidase or glucose-6-phosphate dehydrogenase, chromophores such as fluorescent or luminescent compounds or dyes, radioactive molecules such as $^{32}$P, $^{35}$S or $^{125}$I, and fluorescent molecules such as Alexa or phycocyanins.

Indirect detection systems may also be used, such as, for example, ligands capable of reacting with an antiligand. Ligand/antiligand pairs are well known to those skilled in the art, this being the case, for example, of the following pairs: biotin/streptavidin, hapten/antibody, antigen/antibody, peptide/antibody, sugar/lectin, polynucleotide/sequence complementary to the polynucleotide. In this case, it is the ligand which carries the binding partner. The antiligand may be directly detectable by means of the label reagents described in the previous paragraph, or may itself be detectable by means of a ligand/antiligand.

These indirect detection systems may result, under certain conditions, in an amplification of the signal. This signal amplification technique is well known to those skilled in the art, and reference may be made to the prior patent applications FR98/10084 or WO-A-95/08000 by the applicant or to the article by Chevalier et al.[59].

Depending on the type of labeling used, those skilled in the art will add reagents that make it possible to visualize the labeling.

By way of example of immunoassays as defined above, mention may be made of "sandwich" methods such as ELISA, IRMA and RIA, "competition" methods and direct immunodetection methods such as immunohistochemistry, immunocytochemistry, Western blotting and Dot blotting.

Mass spectrometry can also be used for detecting, in the biological fluid, the tumor marker(s) sought in the method of the invention. The principle of spectrometry is widely known to those skilled in the art and is described, for example, in Patterson, S.[60].

To do this, the biological sample, which may or may not have been pretreated, is passed through a mass spectrometer and the spectrum obtained is compared with that of the tumor marker(s) sought in the method of the invention. An example of pretreatment of the sample consists in passing it over an immunocapture support comprising one of the binding partners for the tumor marker(s) sought in the method of the invention, for example an antibody directed against the tumor marker(s) sought in the method of the invention. Another example of pretreatment of the sample may be prefractionation of the biological sample in order to separate the proteins of the sample from one another. In techniques well known to those skilled in the art, the predominant proteins of the sample may, for example, first of all be depleted.

By virtue of recent technological advances, it has also become possible to quantify proteins in complex biological media using tandem mass spectrometry (MS/MS) carried out using a triple quadrupole analyzer operating in the MRM (multiple reaction monitoring) mode. This operating mode has a double selectivity (two analyzers, parent ion selection and product ion selection) and the detection sensitivity is improved compared with other scanning modes. The technical feasibility of this approach was recently demonstrated by Anderson and Hunter[61] who succeeded in detecting proteins of which the concentration is of the order of a hundred or so ng/ml in plasma, after immunodepletion of the most abundant proteins.

The determination of the presence, in the biological sample, of the "mRNA" tumor marker of interest may be carried out by any method for determining the presence of mRNA in a sample, namely either direct detection of the mRNA, or indirect detection of the mRNA, or any other method for determining the presence of an RNA in a sample, known to those skilled in the art.

The term "direct detection of the mRNA" is intended to mean the demonstration of the mRNA itself in the biological sample.

The direct detection of the mRNA in the biological sample may be carried out by any means known to those skilled in the art, such as, for example, by hybridization with a binding partner specific for the mRNA, where appropriate after amplification by the PCR or NASBA technique.

The term "hybridization" is intended to mean the process during which, under suitable conditions, two nucleotide fragments bind to one another with stable and specific hydrogen bonds so as to form a double-stranded complex. These hydrogen bonds form between the complementary bases adenine (A) and thymine (T) (or uracil (U)) (referred to as an A-T bond) or between the complementary bases guanine (G) and cytosine (C) (referred to as a G-C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds which make it possible to form the double-stranded complex, but also bases that are not bonded to a complementary base. The hybridization between two nucleotide fragments depends on the operating conditions that are used, and in particular the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is desired to hybridize, the hybridization temperature is between approximately 20 and 70° C., in particular between 35 and 65° C., in a saline solution at a concentration of approximately 0.5 to 1 M. The binding partners which are specific or not specific for the mRNA are any partner capable of binding to this mRNA. By way of example, mention may be made of nucleic probes, amplification primers, and any other molecule capable of binding to this mRNA.

The term "hybridization probe" is intended to mean a nucleotide fragment comprising from 5 to 100 nucleic units, in particular from 10 to 35 nucleic units, having a hybridization specificity under given conditions so as to form a hybridization complex with the material specific for the target gene of interest. The hybridization probe may comprise a label enabling its detection.

For the purpose of the present invention, the term "amplification primer" is intended to mean a nucleotide fragment comprising from 5 to 100 nucleic units, preferably from 15 to 30 nucleic units, enabling the initiation of an enzymatic polymerization, such as, in particular, an enzymatic amplification reaction. The term "enzymatic amplification reaction" is intended to mean a process that generates multiple copies of a nucleotide fragment via the action of at least one enzyme. Such amplification reactions are well known to those skilled in the art and mention may in particular be made of the following techniques:

PCR (polymerase chain reaction), as described in U.S. Pat. Nos. 4,683,195, 4,683,202 and 4,800,159, NASBA (nucleic acid sequence-based amplification) with patent application WO 91/02818, and TMA (transcription mediated amplification) with U.S. Pat. No. 5,399,491.

The term "detection" is intended to mean either a physical method, or a chemical method with an intercalating dye such as SYBR® Green I or ethidium bromide, or a method of detection using a label. Many detection methods exist for detecting nucleic acids[62]. The appropriate labels are as defined above.

For the purpose of the present invention, the hybridization probe may be a "detection" probe. In this case, the "detection" probe is labeled by means of a label as defined above. By virtue of the presence of this label, it is possible to detect the presence of a hybridization reaction between a given detection probe and the transcript to be detected.

The detection probe may in particular be a "molecular beacon" detection probe[63]. These "molecular beacons" become fluorescent during hybridization. They have a stem-loop structure and contain a fluorophore and a quencher group. The binding of the specific loop sequence with its complementary target nucleic acid sequence causes unfolding of the stem and the emission of a fluorescent signal during excitation at the appropriate wavelength.

The hybridization probe may also be a "capture" probe. In this case, the "capture" probe is immobilized or can be immobilized on a solid support by any appropriate means, i.e. directly or indirectly, for example by covalence or adsorption. The appropriate solid supports are known to those skilled in the art, and, by way of examples, mention may be made of synthetic materials or natural materials, lattices, magnetic particles, metal derivatives, gels, etc. The solid support may be in the form of a microtitration plate, a membrane as described in application WO-A-94/12670 or a particle. It is also possible to immobilize several different capture probes on the support, each capture probe being specific for a target transcript. In particular, it is possible to use, as support, a biochip on which a large number of probes may be immobilized.

The immobilization of the probes on the support is also known to those skilled in the art, and mention may be made of a deposit of probes by direct transfer, microdeposition, in situ synthesis and photolithography.

The demonstration, in the biological sample, of the DNA modifications or anomalies in the gene encoding the tumor marker of interest may be carried out by any method for determining DNA alterations in a sample, namely either the direct detection of mutations, or the demonstration of alterations in the methylation profile of the loci of interest, or any other method for determining DNA alterations in a sample, known to those skilled in the art.

The mutations may include point substitutions of one nucleotide with another, deletions of one or more nucleotides and insertions of one or more nucleotides. The mutations may be located in the coding portion of the gene of the tumor marker of interest, or in the 5' and 3' noncoding portions, such as the transcription promoter region or the transcription termination region.

The strategies for demonstrating a mutation are based on molecular biology techniques and comprise steps of DNA extraction, amplification by PCR or another amplification technique, hybridization and/or sequencing. In the case of colorectal cancer, the following method has been successfully used to detect mutations in fecal DNA: concentration of the DNA by precipitation, enrichment in the target using capture oligonucleotides on magnetic beads, PCR amplification of the genes of interest, solid-phase sequencing for identifying point mutations[64]. The deletions were identified with respect to the difference in size between the expected reference fragment and the mutated fragment. Imperiale et al.[64] have described a panel of 21 mutations located in the K-ras, APC and p53 genes, which makes it possible to detect 16/31 of invasive cancers.

Other DNA markers used are the BAT-26 deletion, which is a marker for instability of microsatellites and highly amplifiable DNA called long DNA (L-DNA), which is not a specific marker but which appears to reflect the disorganized apoptosis of exfoliated tumor cells in the colonic lumen[65]. These markers are not satisfactory, either in terms of their sensitivity or in terms of their specificity.

As previously indicated, the DNA alterations may also correspond to a modification of the methylation profile of the gene corresponding to the tumor marker of interest. The modification of the methylation profile may correspond to a hypomethylation (decrease in the number of methylations) or to a hypermethylation (increase in the number of methylations). The altered units may be located in the coding portion of the gene of the tumor marker of interest, or in the 5' and 3' noncoding portions, such as the transcription promoter region or the transcription termination region.

The analysis of the DNA methylation may be carried out using techniques based on qualitative and/or quantitative PCR, such as MSP (methylation-specific PCR), bisulfite sequencing, digestion with a methylation-sensitive restriction enzyme coupled with PCR, COBRA (combined bisulfite restriction analysis) and Ms-SNuPE (methylation-sensitive single nucleotide primer extension). All these techniques have been reviewed comparatively and in detail in a methodology article[66].

In the literature, several hypermethylated genes have been reported in the case of colorectal cancer. By way of example, mention may be made of the ALX4 (aristaless-like homeobox-4) gene[56], the promoter region of the TPEF/HHP1 (transmembrane protein containing epidermal growth factor and follistatin domain) gene[67] or else the septin-9 gene[68].

When, in the method of the invention, at least two markers are detected, they may be demonstrated separately, for example using different immunoassay measurements, or else simultaneously, in a multiplex assay.

When, in the method of the invention, two markers of different nature are detected, for example a protein marker and an mRNA marker, two different detection methods, chosen from those described above, may be used. They may also be detected simultaneously, in the same detection medium and under the same reaction conditions, as described in patent application WO 03/104490. The steps of the detection method described in this patent application, which consists in simultaneously detecting hybridization and immunological reactions in a sample that may contain target analytes constituted of at least one nucleic acid and of at least one other ligand of different nature, consist in:

(i) depositing a known volume amount of the sample diluted in a reaction buffer, on a capture surface precoated with capture partners for said target analytes, said capture partners comprising at least one nucleic probe and at least one antiligand, (ii) reacting at a temperature of between 15° C. and 60° C., and (iii) visualizing the hybridization and immunological reactions thus obtained.

The biological sample may require a particular treatment because it may contain the tumor marker(s) sought in the method of the invention, as such, or else it may contain circulating tumor cells which contain the markers sought in the method of the invention and/or circulating tumor cells which are capable of secreting the marker(s) sought in the method of the invention.

Thus, according to one embodiment of the invention, the biological sample is pretreated in order to isolate the circulating tumor cells contained in said fluid.

The expression "isolate circulating tumor cells" is intended to mean obtain a cell fraction enriched in circulating tumor cells.

The treatment of the biological sample in order to isolate the circulating tumor cells can be carried out by cell sorting in a flow cytometer, by enrichment on Ficoll, by enrichment with magnetic beads covered with specific antibodies, or by any other method of specific enrichment known to those skilled in the art.

In the case of blood as biological sample, the circulating tumor cells may be isolated by means of a technique of cell separation on Ficoll combined with depletion of the blood cells using anti-CD45 antibodies coupled to magnetic beads (Dynal Biotech ASA, Norway).

The detection of the tumor marker(s) sought in the method of the invention can then be carried out directly using circulating tumor cells isolated from the biological sample, for example by immunocytochemical labeling of these cells with an antibody against tumor marker(s) sought in the method of the invention, after having deposited the circulating tumor cells on a slide by cytospin. The detection of the tumor marker(s) sought in the method of the invention may also be carried out directly in the circulating tumor cells using the flow cytometry method as described in Métézeau et al.[69].

Under these conditions, said circulating cells can be treated under conditions which make it possible to block the tumor marker(s) sought in the method of the invention, inside said cells. Such a treatment is described by Mathieu et al.[70].

The detection of the tumor marker(s) sought in the method of the invention is then carried out after having made the cell membrane permeable so as to allow entry of the binding partners specific for the marker(s) sought in the method of the invention.

The direct detection of the tumor marker(s) used in the method of the invention, based on the circulating cells, may also be carried out by means of an ELISPOT method, for example by means of the method described in patent application WO 03/076942 filed by the applicant. This method is a method for detecting and/or quantifying circulating tumor cells of a biological sample, which are capable of releasing or secreting, in vitro, one or more tumor marker(s), comprising the steps consisting in:

(i) depositing an amount of said cells at the bottom of a culture surface to which at least one binding partner specific for said tumor marker(s) is attached, (ii) culturing said cells under conditions such that they release or secrete said tumor markers, which are immuno-captured at the bottom of the culture surface, (iii) removing the cells by washing, (iv) adding at least one labeled conjugate specific for said tumor markers, and (v) visualizing the labeling thus obtained.

The direct detection of the tumor marker(s) used in the method of the invention in the tumor cells may also be carried out in the culture medium of said cells after having cultured them under conditions such that they secrete tumor marker(s) used in the method of the invention.

The culture conditions for release or the expression of the tumor markers are conventional conditions such as 37° C. under a humid atmosphere and at 5% $CO_2$.

When the biological sample is a solid sample, the presence of the tumor marker(s) may also be shown in vivo, in situ in the tumors.

In order to show the presence of a tumor marker in a tumor in vivo, any imaging method known to those skilled in the art may be used. For this, a binding partner for said tumor marker may be coupled to an imaging tracer.

The term "coupling of the binding partners to an imaging tracer" is intended to mean the attachment of a tracer capable of being detected by any imaging method known to those skilled in the art, and of directly or indirectly generating a detectable signal. Thus, the tracer may be a radioactive tracer such as technetium-99. In this case, the organ which has the primary cancer or the metastases will bind the tumor marker and its tracer. The radiation emitted by the organ can be filmed with a special camera, for example a gamma-camera. The instrument collects the scintillations generated by the radioactive substance and thus makes it possible to visualize the organ.

In another method of the invention, the tracer may comprise a positron-emitting radioactive substance (fluorine 18). The images will then be acquired by a positron emission tomography system.

In another preferred method of the invention, the partner of the tumor marker(s) may be coupled to nanoparticles. By way of example, they may be supramagnetic nanoparticles; for example, anionic magnetic nanoparticles for use in direct cell labeling and in vivo detection by nuclear magnetic resonance imaging. They may also be gold nanoparticles.

By virtue of the methods of the invention which enable the detection of the tumor marker in vivo, the areas of the body where there has been binding of the binding partner for the tumor marker, cancers producing tumor marker, and in particular colorectal cancer, and also localizations of their remote metastases and involved lymph nodes, may be visualized.

The method of the invention may be used not only for early diagnosis but also for screening, therapeutic follow-up, prognosis and relapse diagnosis in relation to colorectal cancer, since only the cancer cells secrete LEI and this production depends on the grade of the cancer, which constitutes another subject of the invention.

Figure 2:
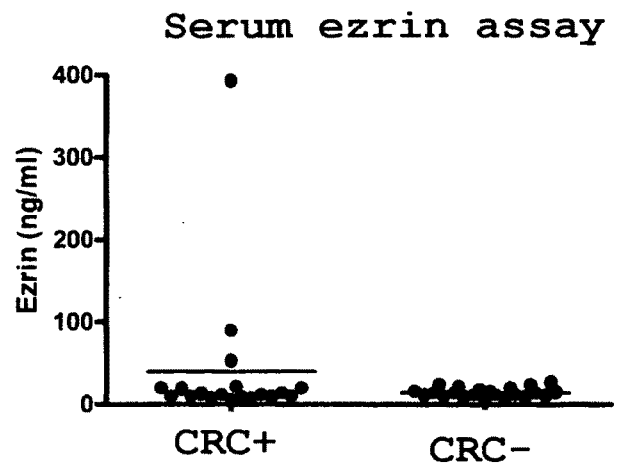
Figure 3:
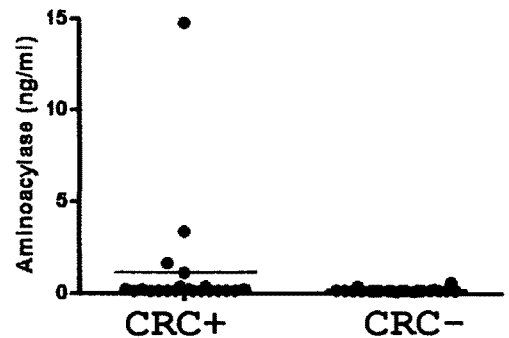
Figure 4:
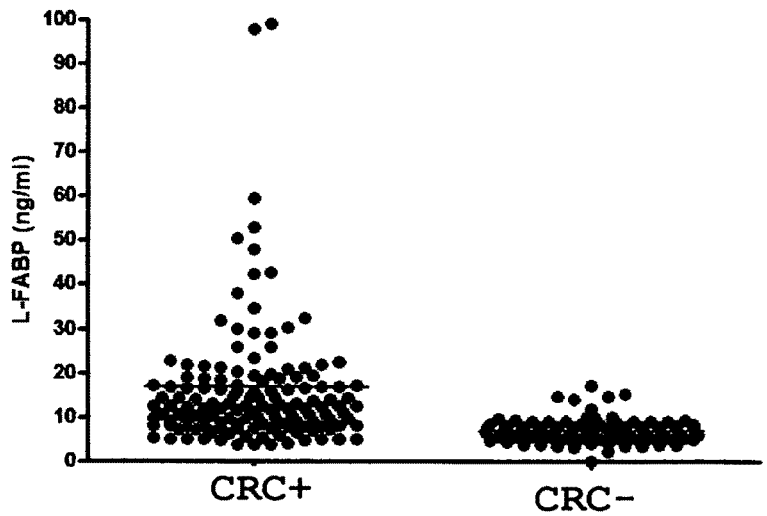
Figure 5:
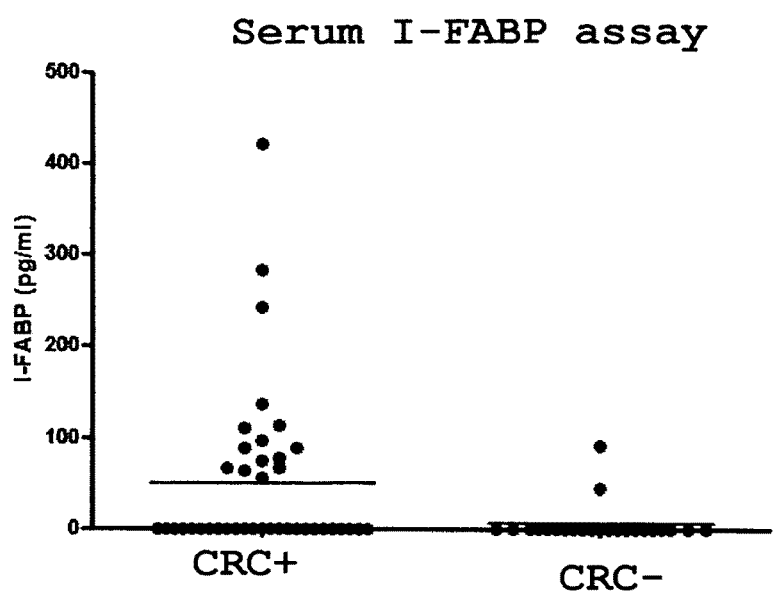
Figure 6:
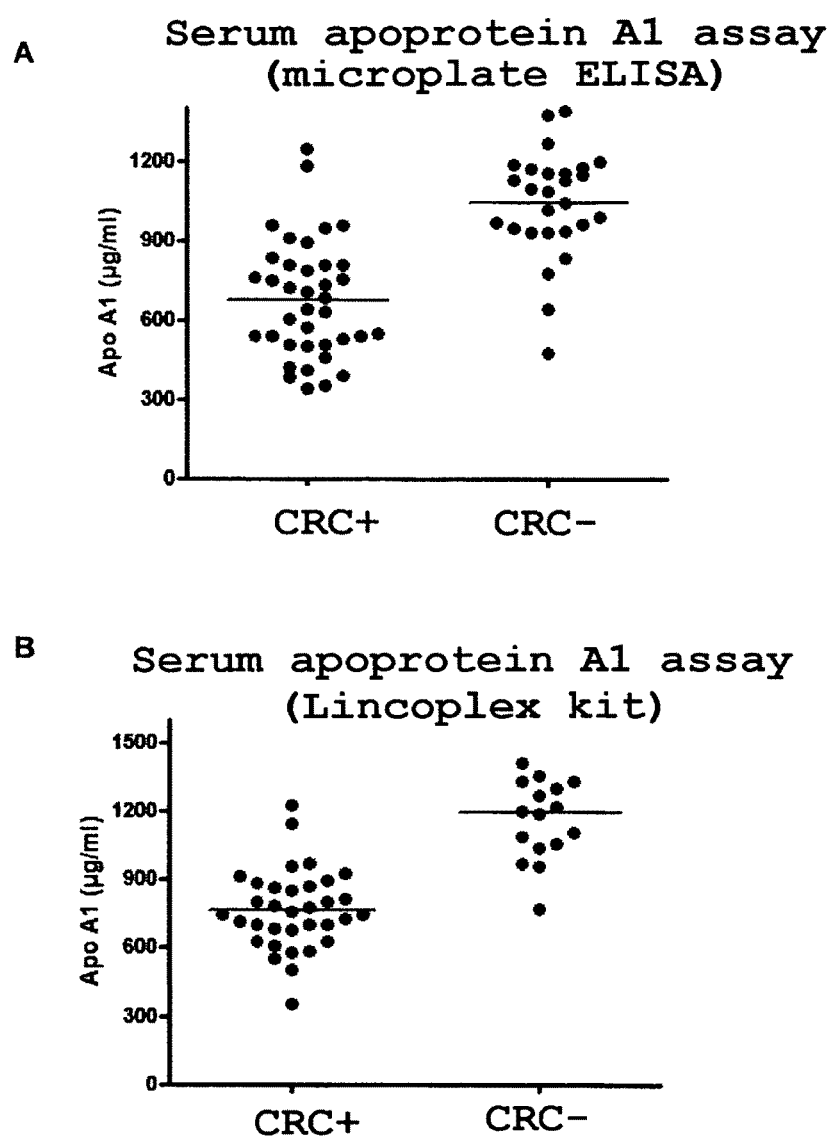
Figure 7:
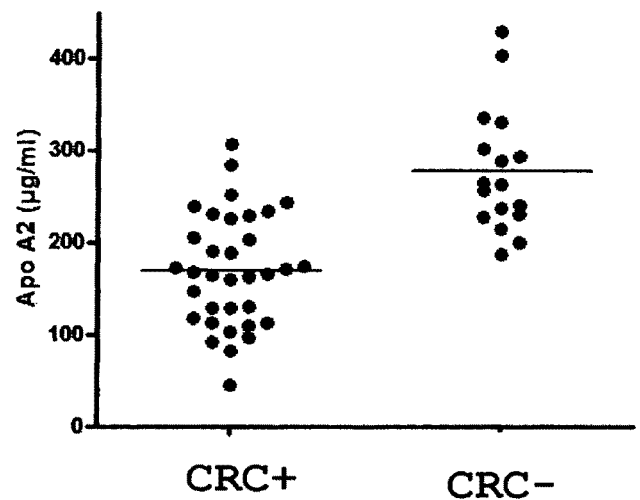
Figure 8:
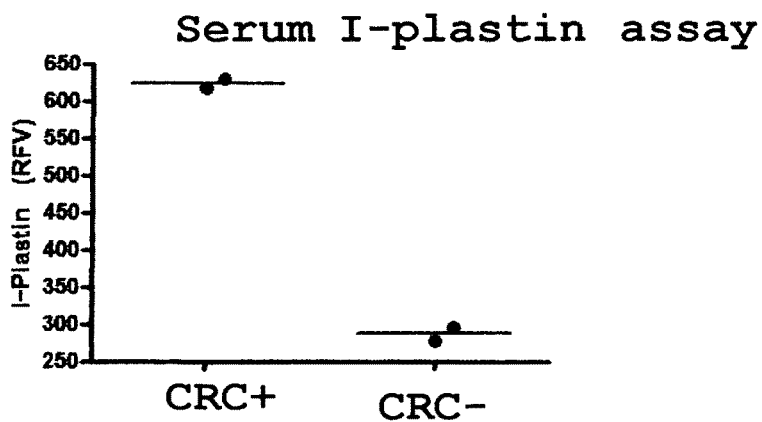
Figure 9:
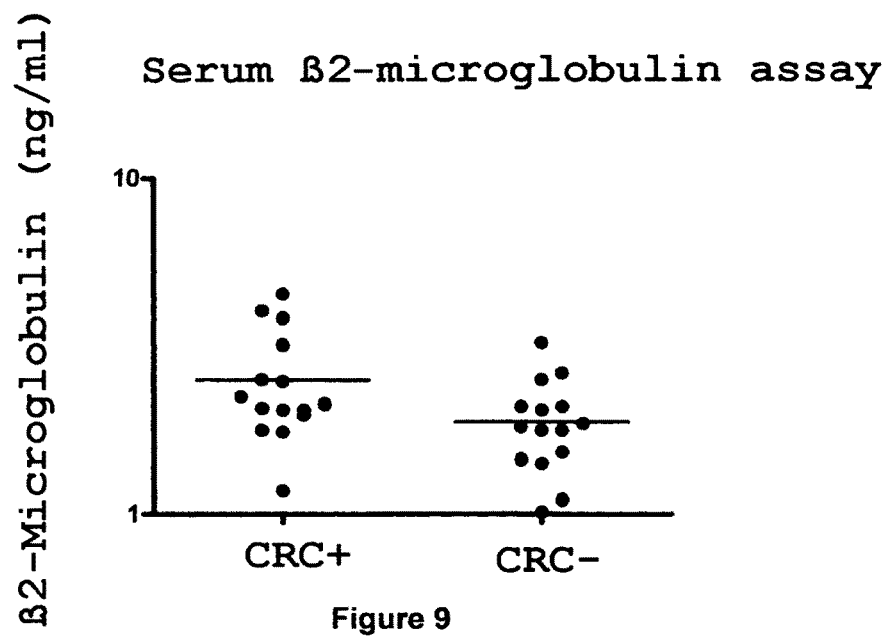
Figure 10:
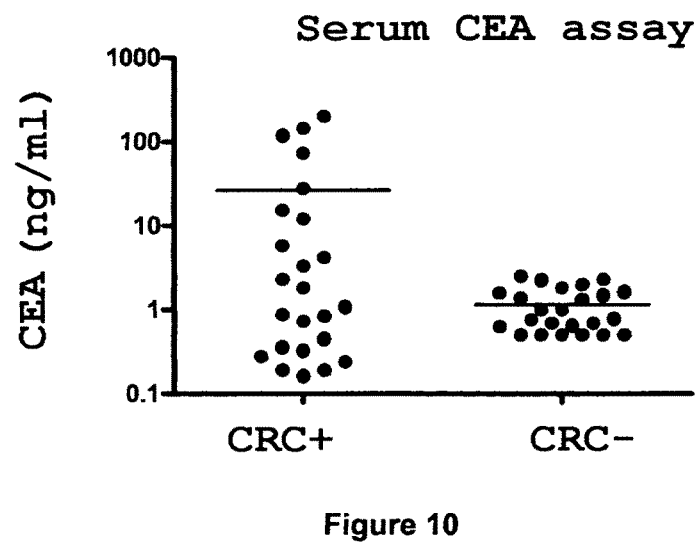
Figure 11:
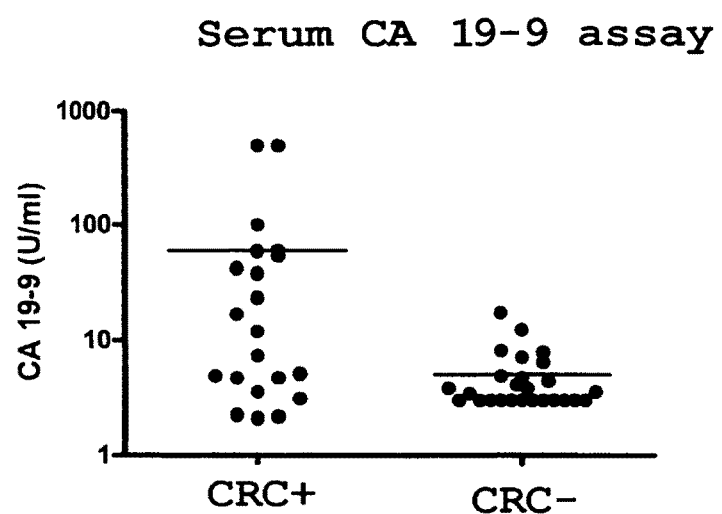
Figure 12:
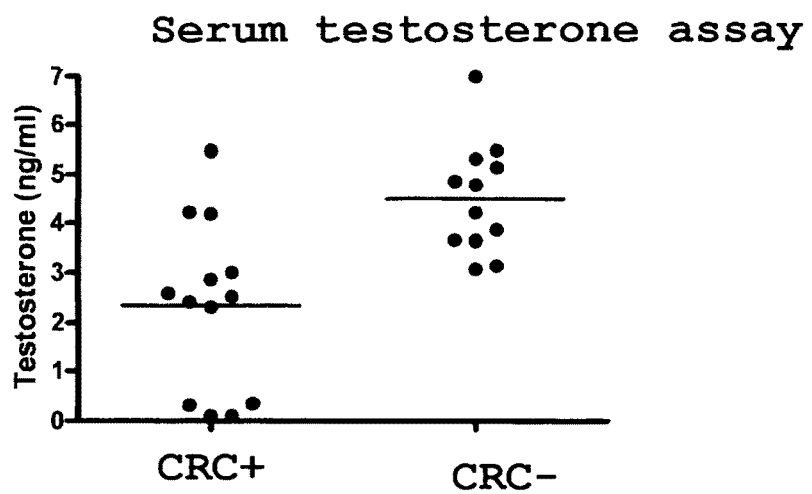
Figure 13:
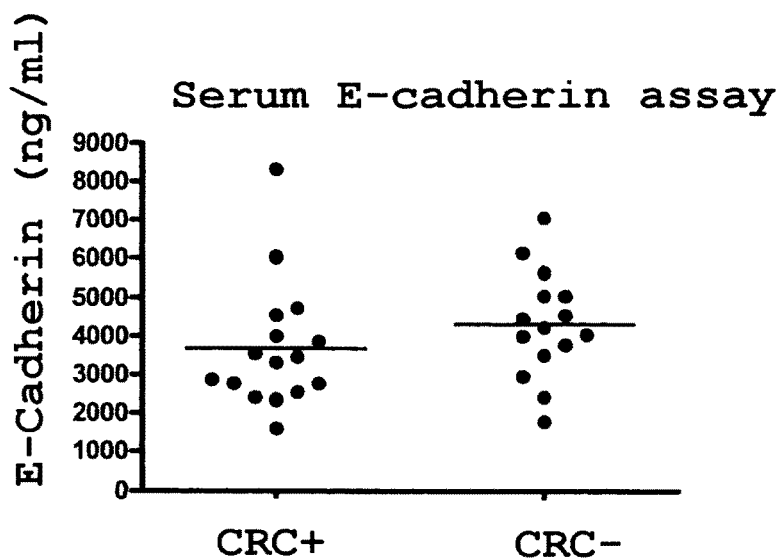
Figure 14:
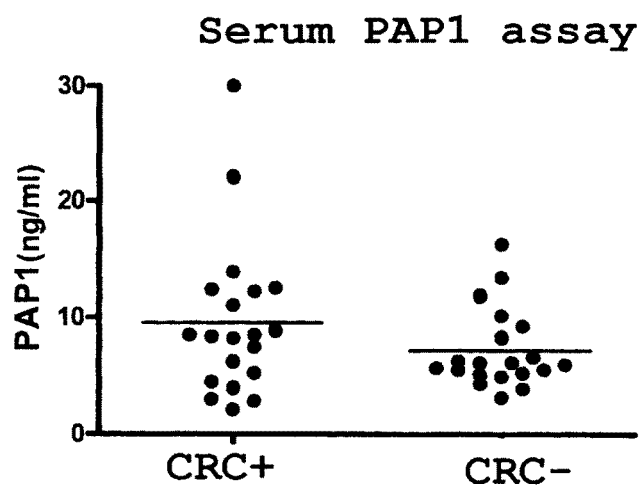
Figure 15:
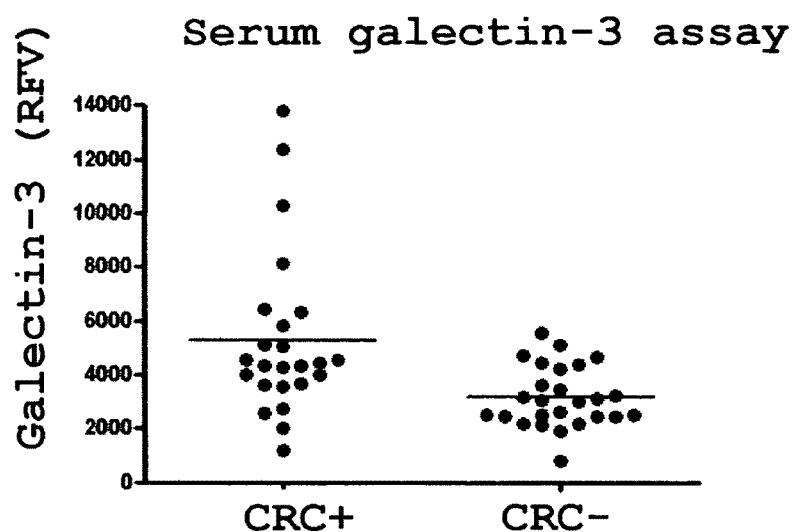
Figure 16:
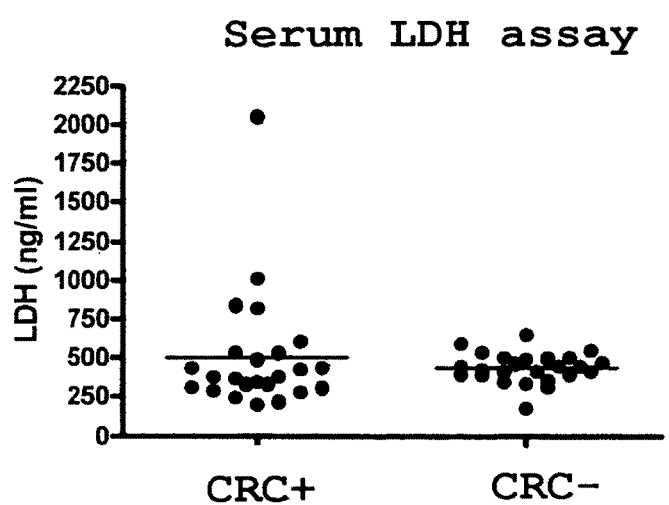
Figure 17:
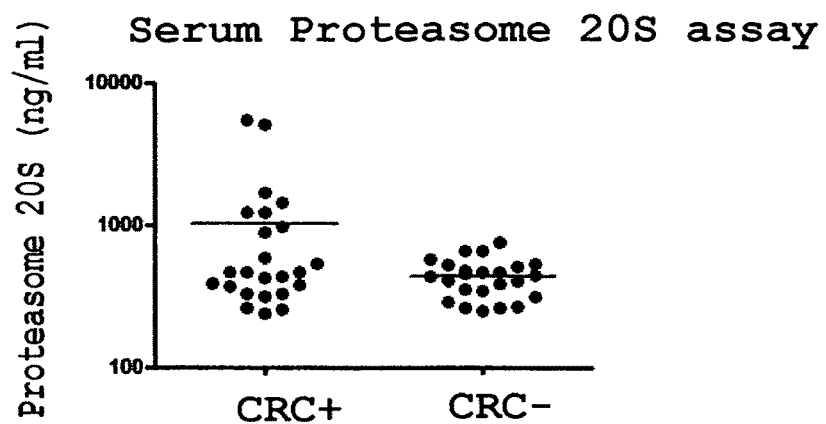
Figure 18:
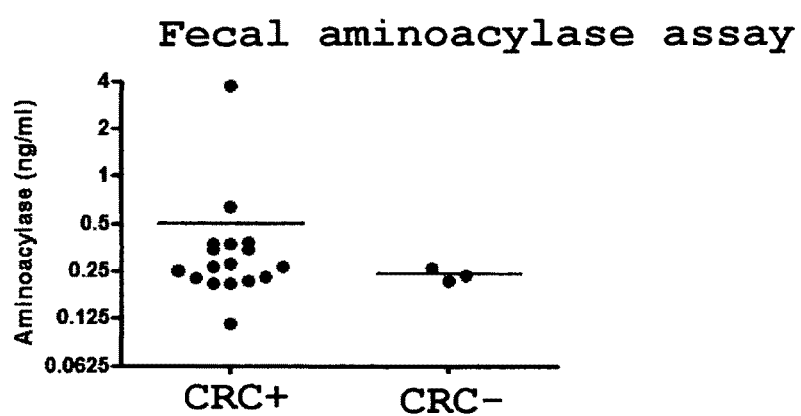
Figure 19:
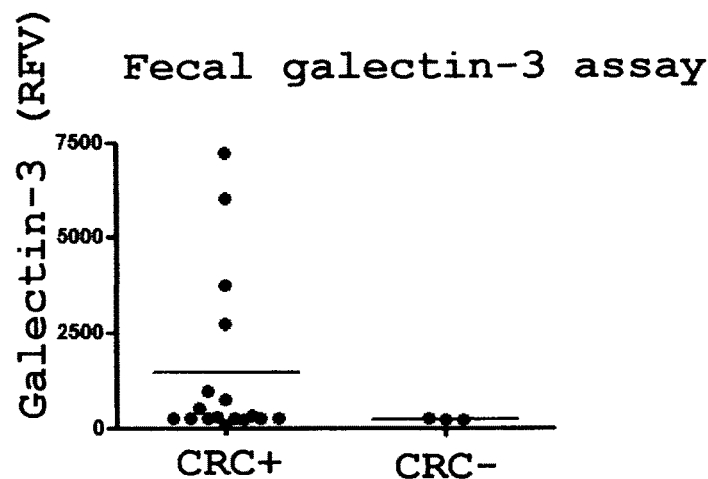
Figure 20:
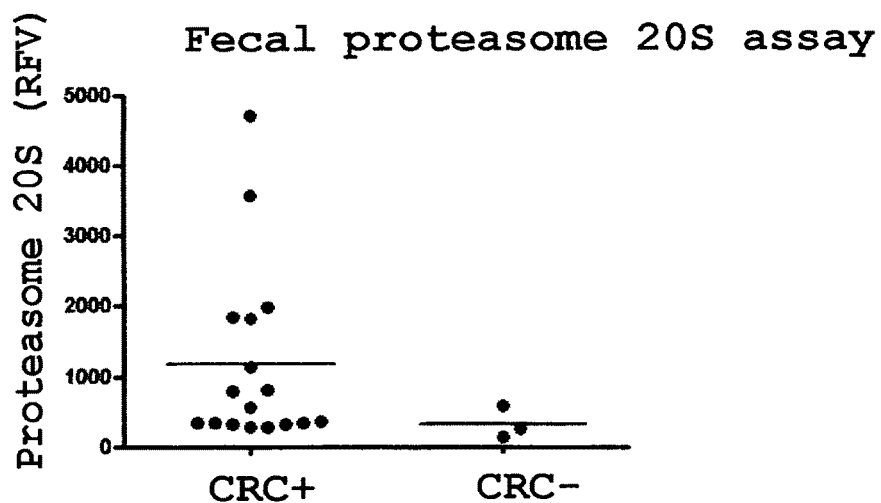
Figure 21:
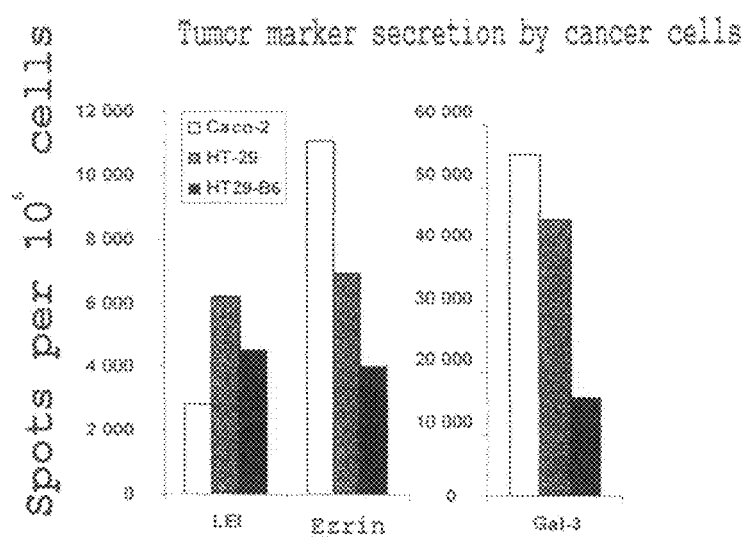

The invention will be understood more clearly by means of the following examples which are given by way of nonlimiting illustration, and also by means of the attached FIGS. 1 to 21, in which:

FIG. 1 is a graph relating to the assaying by ELISA of LEI, in ng/ml, in the serum of patients having colorectal cancer (CRC+) and of healthy patients (CRC−), FIG. 2 is a graph relating to the assaying by ELISA of Ezrin, in ng/ml, in the serum of patients having colorectal cancer (CRC+) and of healthy patients (CRC−), FIG. 3 is a graph relating to the assaying by ELISA of Aminoacylase 1, in ng/ml, in the serum of patients having colorectal cancer (CRC+) and of healthy patients (CRC−), FIG. 4 is a graph relating to the assaying by ELISA of L-FABP, in ng/ml, in the serum of patients having colorectal cancer (CRC+) and of healthy patients (CRC−), FIG. 5 is a graph relating to the assaying by ELISA of I-FABP, in pg/ml, in the serum of patients having colorectal cancer (CRC+) and of healthy patients (CRC−), FIGS. 6A and 6B are graphs relating to the assaying by ELISA of Apolipoprotein AI, in µg/ml, in the serum of patients having colorectal cancer (CRC+) and of healthy patients (CRC−), either by microplate ELISA (FIG. 6A), or with the Lincoplex kit (FIG. 6B), FIG. 7 is a graph relating to the assaying, using the Linco multiplex kit, of Apolipoprotein AII, in μg/ml, in the serum of patients having colorectal cancer (CRC+) and of healthy patients (CRC−), FIG. 8 is a graph relating to the assaying by ELISA of I-Plastin, in RFV (relative fluorescence value), in the serum of patients having colorectal cancer (CRC+) and of healthy patients (CRC−), FIG. 9 is a graph relating to the assaying by ELISA of Beta2-Microglobulin, in ng/ml, in the serum of patients having colorectal cancer (CRC+) and of healthy patients (CRC−), FIG. 10 is a graph relating to the assaying by ELISA of ACE, in ng/ml, in the serum of patients having colorectal cancer (CRC+) and of healthy patients (CRC−), FIG. 11 is a graph relating to the assaying by ELISA of CA 19-9, in U/ml, in the serum of patients having colorectal cancer (CRC+) and of healthy patients (CRC−), FIG. 12 is a graph relating to the assaying by ELISA of Testosterone, in ng/ml, in the serum of patients having colorectal cancer (CRC+) and of healthy patients (CRC−), FIG. 13 is a graph relating to the assaying by ELISA of E-Cadherin, in ng/ml, in the serum of patients having colorectal cancer (CRC+) and of healthy patients (CRC−), FIG. 14 is a graph relating to the assaying by ELISA of PAP1, in ng/ml, in the serum of patients having colorectal cancer (CRC+) and of healthy patients (CRC−), FIG. 15 is a graph relating to the assaying by ELISA of Galectin-3, in RFV, in the serum of patients having colorectal cancer (CRC+) and of healthy patients (CRC−), FIG. 16 is a graph relating to the assaying by ELISA of LDH, in ng/ml, in the serum of patients having colorectal cancer (CRC+) and of healthy patients (CRC−), FIG. 17 is a graph relating to the assaying by ELISA of Proteasome 20S, in ng/ml, in the serum of patients having colorectal cancer (CRC+) and of healthy patients (CRC−), FIG. 18 is a graph relating to the assaying by ELISA of Aminoacylase 1, in ng/ml, in the stools of patients having colorectal cancer (CRC+) and of healthy patients (CRC−), FIG. 19 is a graph relating to the assaying by ELISA of Galectin-3, in RFV, in the stools of patients having colorectal cancer (CRC+) and of healthy patients (CRC−), FIG. 20 is a graph relating to the assaying by ELISA of Proteasome 20S, in RFV, in the stools of patients having colorectal cancer (CRC+) and of healthy patients (CRC−), and FIG. 21 is a graphic representation of an ELISPOT assay for LEI, for Ezrin and for Galectin-3, in number of spots per $10^6$ cancer cells of the Caco-2, HT-29 and HT29-B6 lines.

EXAMPLE 1: CLONING OF THE GENES ENCODING THE TUMOR MARKERS AND EXPRESSION OF THE RECOMBINANT PROTEINS 1. cDNA Amplification and Cloning The Caco-2 colorectal cancer line is cultured in DMEM medium containing 2 mM of L-glutamine, without FCS (fetal calf serum) (all Gibco).

For the cloning of the LEI, L-FABP and Gal-3 genes, the messenger RNAs were extracted from a pellet of $10^8$ Caco-2 cells using the Invitrogen FastTrack 2.0 kit (Cat. No. 45-0019) according to the protocol supplied by the manufacturer. The reverse transcription and PCR steps are carried out in a single step using 450 ng of Caco-2 mRNA with the Superscript III One Step RT-PCR System kit (Invitrogen Cat. No. 12574-018) using the Platinum Taq DNA polymerase enzyme according to the protocol supplied by the manufacturer. The PCR primers used for the gene amplification are given in Table 1.

TABLE 1

| Genes and primers | Oligonucleotides |
| --- | --- |
| LEI | |
| OL215 (SEQ ID No. 1) | 5'-ATGGAGCAGCTGAGCTCAGCAAAC-3' |
| OL216 (SEQ ID No. 2) | 5'-CTAAGGGGAAGAAAATCTCCCCAA-3' |
| L-FABP | |
| Forward (SEQ ID No. 3) | 5'-CGGAGCGTCTCCCATGAGTTTCTCCGGCAAGTA-3' |
| Reverse (SEQ ID No. 4) | 5'-GAAATGCAGACTTGTCTAGATGCGCTTGCTGATGCGCTTGAAGACAATG-3' |
| Gal-3 | |
| OL217 (SEQ ID No. 5) | 5'-ATGGCAGACAATTTTTCGCTCC-3' |
| OL218 (SEQ ID No. 6) | 5'-TTATATCATGGTATATGAAGCACTGG-3' |

The DNA fragments obtained were cloned into the vector pCR2.1 TOPO (LEI and Gal-3) with the TA cloning kit (Invitrogen Cat. No. K4520-01) or the vector pCMV6-XL4 from Origene (L-FABP) after digestion with Bsm BI and Xba I. The plasmids were sequenced in order to verify that the cDNA indeed complies with the expected sequence.

For the cloning of the gene encoding Aminoacylase 1, the total RNA was extracted from a pellet of $10^8$ Caco-2 cells using the RNA Easy Mini kit from Qiagen, according to the protocol supplied by the manufacturer. The reverse transcription is carried out using 10 ng of Caco-2 RNA, with the Superscript II enzyme (Invitrogen) according to the protocol supplied by the manufacturer. The reverse transcription primer is an oligo(dT).

The cDNA derived from this reaction was used as template in a PCR reaction using the AccuPrime Pfx kit (Invitrogen Cat. No. 12344-024) according to the protocol supplied by the manufacturer. The PCR primers are: ACY-1 Fwd2 (SEQ ID No. 7: 5'-GCGAATTCTTTAAGAAGGAGATATACATATGACGAGCAAAGGTCCGGAA GAGGAGCACCCATCG-3') and ACY-1 Rev (SEQ ID No. 8: 5'-GCAAGCTTCAGCTGTCACTGGGCAGGGC-3').

Under these conditions, it was possible to amplify a 1.3 kb fragment which was cloned into a cloning vector of the Zero Blunt TOPO PCR cloning kit type (Invitrogen Cat. No. K2820-20). This plasmid was sequenced in order to verify that the cDNA indeed complies with the expected sequence.

The following DNA fragment (SEQ ID No. 9) containing the I-FABP open reading frame was obtained by chemical synthesis, carried out by the company Geneart.

SEQ ID No. 9:
GGTACCGAATTCCGCGTTTGACAGCACTTGGAAGGTAGACCGGAGTGAAA

ACTATGACAAGTTCATGGAAAAAATGGGTGTTAATATAGTGAAAAGGAAG

CTTGCAGCTCATGACAATTTGAAGCTGACAATTACACAAGAAGGAAATAA

ATTCACAGTCAAAGAATCAAGCGCTTTTCGAAACATTGAAGTTGTTTTTG

-continued
AACTTGGTGTCACCTTTAATTACAACCTAGCAGACGGAACTGAACTCAGG

GGGACCTGGAGCCTTGAGGGAAATAAACTTATTGGAAAATTCAAACGGAC

AGACAATGGAAACGAACTGAATACTGTCCGAGAAATTATAGGTGATGAAC

TAGTCCAGACTTATGTGTATGAAGGAGTAGAAGCCAAAAGGATCTTTAAA

AAGGATTCTAGAGTCGACGAGCTC.

2. Expression Vector Construction

The genes encoding LEI and Galectin-3 were subcloned into the prokaryotic expression vector pMR78[71] and the L-FABP gene was cloned into the vector pET3d (New England Biolabs). The restriction sites necessary for the cloning were introduced by PCR using, as template, the plasmids pCR2.1 TOPO-LEI, pCR2.1 TOPO-Gal-3 and pCMV6-LFABP. The PCR enzyme is the Promega Pfu DNA polymerase, the PCR reaction was carried out according to the manufacturer's instructions, with the primers given in Table 2.

TABLE 2

| Genes and primers | Oligonucleotides |
|---|---|
| LEI | |
| OL228 (SEQ ID No. 10) | 5'-ATGGGAATTCAGGAGCAGCTGAGCTCAGCAA-3' |
| OL229 (SEQ ID No. 11) | 5'-CGATAAGCTTAAGGGGAAGAAAATCTCCCC-3' |
| L-FABP | |
| Forward (SEQ ID No. 12) | 5'-GCTGGCCATGGGCAGCAGCCATCATCATCATCATCACATGAGTTTCTCCGGCAAGTACCAAC-3' |
| Reverse (SEQ ID No. 13) | 5'-GCACGGATCCTAGATGCGCTTGCTGATGCGCTTGAAGAC-3' |
| Gal-3 | |
| OL230 (SEQ ID No. 14) | 5'-ATGGGAATTCAGGCAGACAATTTTTCGCTCC-3' |
| OL231 (SEQ ID No. 15) | 5'-CGATAAGCTTATATCATGGTATATGAAGCACTGG-3' |

The PCR products containing the open reading frames encoding LEI or Galectin-3 were digested with the Eco RI and Hind III restriction enzymes. The fragments were introduced into the vector pMR78 restricted with the same enzymes (plasmids pMR-LEI and pMR-Gal-3). The vector pMR78 contains a 6-histidine sequence in frame with the protein to be expressed, which enables purification by metal-chelate affinity chromatography. The L-FABP PCR product was cloned into the vector pET3d, at the Nco I and Bam HI restriction sites.

For Aminoacylase 1, the TOPO cloning vector was directly digested with the Eco RI and Hind III restriction enzymes in order to generate a 1.3 kb fragment containing the acy1 open reading frame, which was introduced into the vector pStaby1 (Eurogentec). The recombinant plasmid is called pStaby1-ACY.

For I-FABP, the cloning vector provided by Geneart was digested with the Eco RI and Sal I restriction enzymes in order to generate an approximately 400 bp fragment containing the coding sequence, which was introduced into the vector pMRCH79 (derived from the vector pMR78, bioMérieux). The recombinant plasmid is called pMRCH-IFABP.

The plasmids pGEX-Ezrine and pGEX-I-Plastin, which make it possible to express, respectively, Ezrin and I-Plastin fused with GST (glutathione S-transferase), were supplied by the Institut Curie.

3. Recombinant Protein Expression and Purification

The expression plasmids for producing the recombinant tumor markers are introduced into *E. coli* BL21 bacteria and derivatives (Stratagene). The cultures are carried out at ambient temperature with shaking. The precise culture conditions for each protein are reproduced in Table 3. IPTG is isopropyl-beta-D-1-thiogalactosidase.

The bacterial pellets are taken up in 2×PBS (phosphate buffered saline) buffer and passed through a cell disintegrator at 1.5 kbar (Constant System). The lysates are centrifuged at 3000 g for 30 min at 4° C. The supernatant contains the soluble proteins. The pellet contains the inclusion bodies. The buffer for solubilizing the inclusion bodies depends on the protein.

For LEI, the purification is carried out using the soluble fraction, on a column containing 5 mL of Ni-NTA-Sepharose resin (Qiagen) and the protein is eluted with 2×PBS containing 450 mM imidazole, pH 7.5.

For Galectin-3, the inclusion bodies are solubilized in 2×PBS containing 1M urea, and passed over 5 mL of Ni-NTA-Sepharose resin (Qiagen) and the Gal-3 protein is eluted with 2×PBS containing 450 mM imidazole and 1M urea, pH 7.5.

For L-FABP, the purification is carried out using the soluble fraction, with the Ni-IDA kit from Macherey-Nagel.

TABLE 3

| Strain | Culture volume | IPTG induction | Purification |
|---|---|---|---|
| LEI | BL21 | 250 mL | 0.1 mM | Ni-NTA |
| Gal-3 | BL21-Codon plus (DE3)-RIPL | 400 mL | 0.5 mM | Ni-NTA |
| L-FABP | BL21 | 500 mL | 0.1 mM | Ni-IDA |
| GST-Ezrin | BL21 | 250 mL | 0.1 mM | GST |
| ACY-1 | BL21-Codon plus (DE3)-RIPL | 500 mL | 0.1 mM | other |

For GST-Ezrin, the purification is carried out using the inclusion bodies solubilized in 100 mM Tris buffer containing 8M urea and 10 mM DTT, by GST affinity chromatography. A column containing 5 mL of Glutathione Sepharose 4 fast flow gel (Amersham) is used. The equilibration and washing buffer is 2×PBS containing 0.05% Tween 20. The elution buffer is 50 mM Tris-HCl containing 20 mM reduced glutathione, pH 8.

For Aminoacylase 1, the soluble fraction of the culture is passed over an Amersham HiTrap Q FF column and the ACY-1 protein was eluted with 0.3M NaCl at pH 7.5. Since several other proteins were co-eluted under these conditions, the purification was continued on a hydrophobic-interaction column (HIC Phenyl HP, Amersham). The ACY-1 protein was eluted with 0.5M NaCl at pH 7.

The recombinant GST-I-Plastin protein was provided by the Institut Curie in purified form.

The recombinant Calreticulin protein was produced by the company Proteus Services for Industry (Dijon, France). The sequence encoding Calreticulin was obtained by chemical synthesis.

EXAMPLE 2: PRODUCTION OF MONOCLONAL ANTIBODIES DIRECTED AGAINST THE TUMOR MARKERS

1. Animal Model

The immunization experiments were carried out in female BALB/c (H-$2^d$) mice that were 6 to 8 weeks at the time of the first immunization.

2. Immunogens and Immunizations

In order to increase the immune responses obtained in the mice and to be able to generate monoclonal antibodies, the tumor markers were produced in the form of recombinant proteins produced according to the procedures described in Example 1. The LDH protein was obtained from the company SciPac (Cat. No. 103-133). These proteins were mixed volume for volume with Freund's adjuvant (Sigma), prepared in the form of a water-in-oil emulsion and which is known to have a good immunogenic capacity. 3 mice were immunized for each tumor marker. The mice received 3 successive doses of 10 µg of the immunogens at 0, 2 and 4 weeks. All the injections were given subcutaneously. The first injection is given as a mixture with complete Freund's adjuvant, the following two are given as a mixture with incomplete Freund's adjuvant. Between D50 and D70 after the first injection, the humoral responses were restimulated with an intravenous injection of 100 µg of the recombinant protein.

3. Monitoring of the Appearance of the Humoral Response

In order to monitor the appearance of the antibodies, blood samples are taken regularly from the mice. The presence of the anti-tumor marker antibodies is tested using an ELISA. The protein of interest is used for capture (1 µg/well); after saturation, the antigen is reacted with various dilutions of the test sera (incubation at 37° C. for 1 h). The specific antibodies present in the serum are revealed with an AffiniPure goat anti-mouse IgG antibody conjugated to alkaline phosphatase (H+L, Jackson Immunoresearch, Cat no. 115-055-146), which binds to the antibodies being sought (0.1 µg/well).

4. Production of Monoclonal Antibodies

Three days after the final injection, for each tumor marker, one of the immunized mice was sacrificed. The blood and the spleen were taken. The splenocytes obtained from the spleen were cultured with Sp2/0-Ag14 myeloma cells in order for them to fuse and become immortalized, according to the protocol described by Köhler and Milstein[72,73]. After an incubation period of 12-14 days, the supernatants of the hybridomas obtained were screened in order to determine the presence of anti-tumor marker antibodies, using the ELISA assay described in point 3 of this example. When GST fusion proteins were used as immunogen, the clones directed against GST are eliminated by carrying out an ELISA screening with uncoupled GST for capture. The positive hybridoma colonies were subcloned twice according to the limiting dilution technique, which is well known to those skilled in the art.

5. Characterization of the Monoclonal Antibodies by Immunoblotting

The list of monoclonal antibodies obtained against the various tumor markers is given in Table 4. These monoclonal antibodies were analyzed by the Western blotting technique.

TABLE 4

| Tumor markers | Monoclonal antibody name |
| --- | --- |
| Leukocyte Elastase Inhibitor (LEI) | 21B10A5 and 10E1H1 |
| Ezrin | 4A7A6C1 and 4A9H5 |
| Aminoacylase 1 | 2A7F6 and 11H7D9 |
| I-plastin | 3D11D10, 8C8C5, 3A3H2, 8G2D2 |
| Calreticulin | 5C10H10 and 11B6D11 |
| L-lactate dehydrogenase chain B (LDH) | 3F11E11 and 12F10G8 |
| Galectin-3 | 12F8A12 and 14A5G1 |

5.1. Methodology

The Caco-2 and HT-29 line cell culture extracts are prepared by directly lyzing the cell pellet with 600 µl of an aqueous solution of 8.3M urea, 2M thiourea, 4% 3[(3-cholamidopropyl)dimethylammonio]-1-propane sulfonate (CHAPS), 100 mM DTT, 2% Servalyte 4-9 (Serva, Heidelberg, Germany) and 0.1 g/l Orange G, and then treated according to the NuPAGE Novex gel sample preparation protocol (Invitrogen). To obtain the tissue extracts, tumor and mucosal biopsies of patients GHBD001, GHBD004 and CLSP109 were dissected with a scalpel, and were then subjected to 10 cycles of extraction in the Medimachine system (Becton Dickinson) using 50-µm Medicons with 1 ml of PBS buffer containing 2.5 mM EDTA and protease inhibitors (tablets, Roche). These 10 ml of cell suspension are pooled, made up to 25 ml, and then centrifuged for 15 min at 600 g. The supernatant corresponds to the tissue extract which is treated according to the NuPAGE Novex gel sample preparation protocol. Reduced samples are used, at a final total protein concentration of 0.4 mg/ml. The deposit volume is 20 µl per well, on a NuPAGE Novex Bis-Tris 4-12% gel, with MOPS running buffer. After migration (at 200 V, for 1 hour) and transfer onto a PVDF membrane (at 400 mA, for 45 min), the quality of the transfer is assessed by staining with amido black.

The membranes are saturated with 5% skimmed milk (Régilait) in a solution of TNT (15 mM Tris, 0.14M NaCl, 0.5% Tween 20, pH 8) at ambient temperature for 1 hour. After saturation, the membranes are incubated for 1 hour with the various test antibodies diluted to 10 µg/ml in the saturating solution. After rinsing with TNT, the membranes are incubated for 1 hour at ambient temperature with an anti-mouse-horseradish peroxidase conjugate diluted to 1:5000, (Cat No. 115-035-062, Jackson Immunoresearch) in the saturating solution. After rinsing, the developing is carried out with the Substrate Supersignal West Dura Extended kit (Cat No. 34076, Pierce) according to the recommended information for use.

The chemiluminescence signal on the membranes was measured with the VersaDoc imaging system from Biorad. Based on the image of the Western blot, the volumes of the bands which correspond to the various tumor markers were evaluated with the QuantityOne software (Bio-Rad). The volume corresponds to the intensity of the chemiluminescence signal multiplied by the surface area of the band.

5.2. Results

The Western blotting results are reproduced in Table 5, which gives the volume of the bands corresponding to the tumor marker of interest for the Western blotting analyses, as a function of the various samples tested. These results show that the tumor markers tested are indeed expressed by the Caco-2 and HT-29 colon cancer lines, and also in the tissues, as shown with the extracts of tumor and mucosa, obtained from the patients. The intensity of the signal obtained with an antibody on a sample can be compared to the signals obtained with the other samples and the same antibody. The technique used makes it possible to confirm the presence or absence of the marker in the tissue (non-remote sample) and the specificity of the antibodies with respect to the markers. This technique was not used in this example in the remote samples because it would not make it possible to come to a conclusion regarding the presence or absence of the tumor marker in the remote samples, nor to determine whether the concentration of said tumor marker is increased or decreased in said samples. Furthermore, the experimental scheme used does not make it possible to compare the reactivity of one antibody with another.

In order to obtain serum, the blood sample is taken on a dry tube. In order to obtain plasma, the blood sample is taken on an EDTA tube. After coagulation, the tube is centrifuged for 10 min at 1000 g, and the serum is removed, aliquoted and stored at −80° C. The tube of plasma is directly centrifuged for 10 min at 1000 g, and the plasma is removed, aliquoted and stored at −80° C. The samples are completely documented for the clinical history of the patients.

2. Serum Assay for the LEI Tumor Marker

The LEI protein was assayed using the antibodies described in Example 2 and an ELISA assay using the Vidas® automated device (bioMérieux). To do this, the

TABLE 5

| Tumor marker and antibody | Caco-2 | HT-29 | Tumor tissue GHBD001 | Mucosal tissue GHBD004 | Tumor tissue GHBD004 | Mucosal tissue CLSP109 | Tumor tissue CLSP109 |
|---|---|---|---|---|---|---|---|
| LEI | | | | | | | |
| 21B10A5 | 8365 | 7678 | NT | 60200 | 36506 | NT | NT |
| 10E1H1 | 0 | 0 | NT | 13357 | 6893 | NT | NT |
| Ezrin | | | | | | | |
| 4A9H5 | 7066 | 4742 | NT | NT | NT | 1588 | 2446 |
| 4A7A6C1 | 123436 | 116448 | 42480 | 15303 | 67439 | NT | NT |
| Aminoacylase 1 | | | | | | | |
| 2A7F6 | 10687 | 4787 | NT | NT | NT | 4477 | 7238 |
| 11H7D9 | 217664 | 232005 | 36093 | 10513 | 30233 | NT | NT |
| I-plastin | | | | | | | |
| 3D11D10 | 136725 | NT | NT | NT | NT | 275477 | 246564 |
| 8C8C5 | 557 | 1110 | 4364 | 77 | 0 | NT | NT |
| Calreticulin | | | | | | | |
| 5C10H10 | 2842 | 3040 | NT | NT | NT | 2503 | 3294 |
| 11B6D11 | 3261 | 2937 | NT | NT | NT | 2070 | 2764 |
| LDH | | | | | | | |
| 3F11E11 | 45391 | NT | NT | NT | NT | 30411 | 13942 |
| 12F10G8 | 122907 | 154593 | 11841 | 15811 | 53285 | NT | NT |
| Galectin-3 | | | | | | | |
| 12F8A12 | 245712 | 65790 | 18262 | 12961 | 7307 | NT | NT |
| 14A5G1 | 254531 | 120010 | 79833 | 98361 | 45872 | NT | NT |

NT: not tested.

5.3. Monoclonal Antibodies Directed Against I-Plastin

In the patient GHBD004, the 8C8C5 antibody does not light up, or only very weakly lights up, the band which corresponds to I-Plastin. The presence of I-Plastin in these samples can be demonstrated using, for example, the 8G2D2 antibody, which has a better affinity for I-Plastin in blotting.

Since I-Plastin is a member of a family of proteins comprising 2 other isoforms (L-Plastin and T-Plastin) with which it has more than 70% homology, we tested all the clones of monoclonal antibodies obtained, for their reactivity with respect to the GST-plastin-L and GST-Plastin-T proteins (provided by the Institut Curie). At the end of this screening, we selected the clones 3D11D10, 8C8C5, 3A3H2 and 8G2D2 which do not exhibit any cross-reactivity with the other members of the family. These antibodies are indeed specific for the I-Plastin isoform.

EXAMPLE 3: SERUM ASSAYS FOR THE TUMOR MARKERS

1. Patients and Specimens

Blood samples are collected from a network of 8 clinical centers distributed throughout France, in the context of 2 Huriet-law protocols.

ELISA assay was constructed using the reagents of the Vidas® HBs Ag Ultra kit (bioMérieux, Cat. No. 30315). The reagents were used as described in the corresponding information sheet (ref 11728 D-FR-2005/05), with the following modifications:

1. The cones were sensitized with the capture antibody 10E1H1 at a concentration of 10 μg/ml.
2. The content of the second well of the HBs Ag Ultra cartridge was replaced with 300 μl of revealing antibody 21B10A5, coupled to biotin, diluted to 1 μg/ml in the buffer of the second well of the Vidas® HBs Ag Ultra kit (buffer with goat serum and sodium azide at 1 g/l).
3. The serum, plasma or stool samples (50 μl) were diluted directly in the second well of the HBs Ag Ultra cartridge, pure or after a prior dilution to 1/20 in the buffer of the second well of the Vidas® HBs Ag Ultra kit (buffer with goat serum and sodium azide at 1 g/l).
4. The ELISA reaction was carried out using the Vidas® automated device and the protocol of the HBs Ag Ultra kit.
5. The results were obtained in the form of crude values after subtraction of the background noise (reading of the substrate before reaction).

A standard curve was established by assaying a range of concentrations of the tumor marker in the form of recombinant protein. The standard curve was plotted by reporting the concentration of the tumor marker along the x-axis and the signal read by Vidas® (RFV or Relative Fluorescence Value) along the y-axis. The concentration of tumor marker present in the body fluid to be assayed (blood, serum, plasma, stool) was calculated by reporting the concentration corresponding to the RFV signal read by Vidas®.

The amounts obtained for the patients analyzed are reported in FIG. 1. It may be noted, on this figure, that 3 sera of patients having stage IV colorectal cancer and 1 serum of a patient having stage III colorectal cancer show a clear increase in their amount of serum LEI.

3. Serum Assay for the Ezrin Tumor Marker

The Ezrin protein was assayed using the antibodies described in Example 2 and an ELISA assay using the Vidas® automated device (bioMérieux). To do this, the ELISA assay was constructed using the reagents of the Vidas® HBs Ag Ultra kit (bioMérieux, Cat. No. 30315). The reagents were used as described in the corresponding information sheet (ref. 11728 D-FR-2005/05), with the following modifications:

1. The cones were sensitized with the capture antibody 4A9H5 at a concentration of 30 μg/ml.
2. The content of the second well of the HBs Ag Ultra cartridge was replaced with 300 μl of revealing antibody 4A7A6C1, coupled to biotin, diluted to 1 μg/ml in the buffer of the second well of the Vidas® HBs Ag Ultra kit (buffer with goat serum and sodium azide at 1 g/l).
3. The serum, plasma and stool samples (50 μl) were diluted directly in the second well of the HBs Ag Ultra cartridge.
4. The ELISA reaction was carried out using the Vidas® automated device and the HBs Ag Ultra protocol, in which the step of incubating the sample with the capture and revealing antibodies had been taken to 100 cycles.
5. The results were obtained in the form of crude values after subtraction of the background noise (reading of the substrate before reaction).

The concentration of the tumor marker present in the body fluid to be assayed (blood, serum, plasma, stool) was calculated according to the procedure described in paragraph 2 regarding the assaying of LEI.

The amounts obtained for the patients analyzed are reported in FIG. 2. It may be noted, in this figure, that 3 sera from patients having stage IV colorectal cancer show a clear increase in their amount of serum Ezrin.

4. Serum Assay for the Aminoacylase 1 Tumor Marker

The Aminoacylase 1 protein was assayed using the antibodies described in Example 2 and an ELISA assay using the Vidas® automated device (bioMérieux). To do this, the ELISA assay was constructed using the reagents of the Vidas® HBs Ag Ultra kit (bioMérieux, Cat. No. 30315). The reagents were used as described in the corresponding information sheet (ref 11728 D-FR-2005/05), with the following modifications:

1. The cones were sensitized with the capture antibody 2A7F6 at a concentration of 20 μg/ml.
2. The content of the second well of the HBs Ag Ultra cartridge was replaced with 300 μl of revealing antibody 11H7D9, coupled to biotin, diluted to 1 μg/ml in the buffer of the second well of the Vidas® HBs Ag Ultra kit (buffer with goat serum and sodium azide at 1 g/l).
3. The serum, plasma or stool samples (100 μl) were diluted directly in the second well of the HBs Ag Ultra cartridge.
4. The ELISA reaction was carried out using the Vidas® automated device and the HBs Ag Ultra protocol, in which the step of incubating the sample with the capture and revealing antibodies had been taken to 100 cycles.
5. The results were obtained in the form of crude values after subtraction of the background noise (reading of the substrate before reaction).

The concentration of the tumor marker present in the body fluid to be assayed (blood, serum, plasma, stool) was calculated according to the procedure described in paragraph 2 regarding the assaying of LEI.

The amounts obtained for the patients analyzed are reported in FIG. 3. It may be noted, in this figure, that 1 serum from a patient having stage II colorectal cancer, 1 serum from a patient having stage III colorectal cancer and 2 sera from patients having stage IV colorectal cancer show a clear increase in their amount of serum Aminoacylase 1.

5. Serum Assay for the L-FABP Tumor Marker

We used an ELISA kit marketed by the company Hycult Biotechnology to assay the human L-FABP protein (Cat. No. HK404). This kit makes it possible to quantify the L-FABP protein in cell culture supernatants or in serum, plasma or urine, in order to determine the presence of lesions in the liver. We followed the procedure recommended by the manufacturer, with 2 modifications: the incubations were carried out at 37° C. and not at ambient temperature, the sera were diluted to $1/10^{th}$ before the assay. The assaying of the L-FABP protein can be carried out by alternative techniques, well known to those skilled in the art.

The results of the assaying of serum L-FABP in patients by ELISA are given in Table 6.

TABLE 6

| Pathological condition[a] | Sample identifier | Nature | Stage | L-FABP ng/ml |
|---|---|---|---|---|
| CRC+ | CLSP047/F0 | Serum | I | 6.3 |
| CRC+ | CBSE025/F0 | Serum | I | 14.1 |
| CRC+ | CLSP162/F0 | Serum | I | 10.9 |
| CRC+ | GHBD011/F0 | Serum | I | 17.2 |
| CRC+ | GHBD026/F0 | Serum | I | 6.0 |
| CRC+ | GHBD060/F0 | Serum | I | 8.6 |
| CRC+ | CBSE001/F0 | Serum | I | 29.0 |
| CRC+ | CLSP007/F0 | Serum | I | 19.3 |
| CRC+ | CLSP016/F0 | Serum | I | 25.9 |
| CRC+ | CSEM003/F0 | Serum | I | 30.3 |
| CRC+ | CLSP015/F0 | Serum | I | 5.0 |
| CRC+ | CBSE011/F0 | Serum | I | 10.3 |
| CRC+ | GHBD012/F0 | Serum | I | 7.2 |
| CRC+ | CLSP150/F0 | Serum | I | 4.9 |
| CRC+ | GHBD015/F0 | Serum | I | 13.6 |
| CRC+ | CBSE016/F0 | Serum | I | 10.3 |
| CRC+ | CBSE022/F0 | Serum | I | 8.8 |
| CRC+ | CLSP118/F0 | Serum | I | 7.1 |
| CRC+ | CLSP145/F0 | Serum | I | 12.2 |
| CRC+ | CBSE011/F0 | Serum | I | 7.6 |
| CRC+ | CLSP150/F0 | Serum | I | 3.6 |
| CRC+ | GHBD003/F0 | Serum | I | 9.1 |
| CRC+ | GHBD015/F0 | Serum | I | 12.4 |
| CRC+ | CLSP059/F0 | Serum | I | 16.3 |
| CRC+ | GHBD035/F0 | Serum | I | 11.8 |
| CRC+ | CLSP146/F0 | Serum | I | 21.7 |
| CRC+ | CLSP067/F0 | Serum | I | 21.0 |
| CRC+ | CLSP100/F0 | Serum | I | 21.6 |
| CRC+ | GHBD020/F0 | Serum | II | 14.4 |
| CRC+ | GHBD025/F0 | Serum | II | 7.7 |
| CRC+ | GHBD023/F0 | Serum | II | 5.1 |
| CRC+ | GHBD029/F0 | Serum | II | 10.5 |

TABLE 6-continued

| Pathological condition[a] | Sample identifier | Nature | Stage | L-FABP ng/ml |
|---|---|---|---|---|
| CRC+ | CLSP076/F0 | Serum | II | 16.5 |
| CRC+ | CLSP087/F0 | Serum | II | 7.6 |
| CRC+ | CLSP110/F0 | Serum | II | 10.1 |
| CRC+ | GHBD047/F0 | Serum | II | 34.5 |
| CRC+ | GHBD050/F0 | Serum | II | 20.8 |
| CRC+ | CLSP060/F0 | Serum | II | 18.6 |
| CRC+ | CLSP085/F0 | Serum | II | 9.8 |
| CRC+ | GHBD021/F0 | Serum | II | 8.1 |
| CRC+ | GHBD029/F0 | Serum | II | 9.5 |
| CRC+ | CLSP086/F0 | Serum | II | 7.4 |
| CRC+ | CLSP075/F0 | Serum | II | 14.6 |
| CRC+ | CLSP063/F0 | Serum | II | 12.6 |
| CRC+ | CLSP088/F0 | Serum | II | 16.6 |
| CRC+ | GHBD009/F0 | Serum | II | 13.1 |
| CRC+ | CBSE004/F0 | Serum | II | 3.5 |
| CRC+ | CLSP136/F0 | Serum | II | 12.3 |
| CRC+ | CLSP105/F0 | Serum | II | 8.8 |
| CRC+ | CLSP096/F0 | Serum | II | 9.7 |
| CRC+ | CLSP154/F0 | Serum | II | 7.6 |
| CRC+ | CBSE004/F0 | Serum | II | 4.7 |
| CRC+ | CLSP133/F0 | Serum | II | 9.4 |
| CRC+ | CLSP136/F0 | Serum | II | 8.9 |
| CRC+ | GHBD016/F0 | Serum | II | 7.3 |
| CRC+ | P38868 s1 | Serum | II | 13.1 |
| CRC+ | GHBD039/F0 | Serum | II | 16.1 |
| CRC+ | GHBD066/F0 | Serum | II | 18.0 |
| CRC+ | CLSP157/F0 | Serum | II | 7.7 |
| CRC+ | CLSP107/F0 | Serum | II | 17.0 |
| CRC+ | CLSP102/F0 | Serum | II | 13.8 |
| CRC+ | CLSP093/F0 | Serum | II | 25.9 |
| CRC+ | CLSP117/F0 | Serum | II | 20.3 |
| CRC+ | CLSP115/F0 | Serum | II | 50.4 |
| CRC+ | CBSE017/F0 | Serum | II | 13.8 |
| CRC+ | CLSP143/F0 | Serum | II | 14.2 |
| CRC+ | CLSP122/F0 | Serum | II | 7.4 |
| CRC+ | CLSP119/F0 | Serum | II | 16.7 |
| CRC+ | CLSP147/F0 | Serum | II | 7.9 |
| CRC+ | CLSP050/F0 | Serum | III | 15.7 |
| CRC+ | CLSP090/F0 | Serum | III | 3.7 |
| CRC+ | CLSP089/F0 | Serum | III | 5.8 |
| CRC+ | GHBD019/F0 | Serum | III | 9.1 |
| CRC+ | GHBD037/F0 | Serum | III | 14.1 |
| CRC+ | CLSP094/F0 | Serum | III | 5.3 |
| CRC+ | GHBD059/F0 | Serum | III | 22.4 |
| CRC+ | GHBD045/F0 | Serum | III | 5.4 |
| CRC+ | CLSP081/F0 | Serum | III | 7.5 |
| CRC+ | GHBD004/F0 | Serum | III | 10.4 |
| CRC+ | CLSP072/F0 | Serum | III | 6.6 |
| CRC+ | CLSP027/F0 | Serum | III | 4.6 |
| CRC+ | CLSP072/F0 | Serum | III | 15.5 |
| CRC+ | GHBD019/F0 | Serum | III | 10.4 |
| CRC+ | GHBD007/F0 | Serum | III | 42.3 |
| CRC+ | GHBD034/F0 | Serum | III | 11.1 |
| CRC+ | CLSP078/F0 | Serum | III | 53.0 |
| CRC+ | CLSP074/F0 | Serum | III | 14.2 |
| CRC+ | CLSP044/F0 | Serum | III | 5.0 |
| CRC+ | CBSE023/F0 | Serum | III | 11.9 |
| CRC+ | CLSP074/F0 | Serum | III | 9.5 |
| CRC+ | CLSP144/F0 | Serum | III | 5.0 |
| CRC+ | CLSP044/F0 | Serum | III | 4.1 |
| CRC+ | CLSP097/F0 | Serum | III | 10.4 |
| CRC+ | CLSP098/F0 | Serum | III | 11.5 |
| CRC+ | CLSP121/F0 | Serum | III | 8.3 |
| CRC+ | GHBD005/F0 | Serum | III | 7.9 |
| CRC+ | CBSE007/F0 | Serum | III | 59.6 |
| CRC+ | GHBD037/F0 | Serum | III | 14.1 |
| CRC+ | GHBD058/F0 | Serum | III | 12.3 |
| CRC+ | CBSE010/F0 | Serum | III | 23.3 |
| CRC+ | CBSE013/F0 | Serum | III | 19.1 |
| CRC+ | CLSP091/F0 | Serum | III | 18.6 |
| CRC+ | CLSP123/F0 | Serum | III | 42.5 |
| CRC+ | CBSE006/F0 | Serum | III | 11.8 |
| CRC+ | CLSP106/F0 | Serum | III | 18.9 |
| CRC+ | CLSP141/F0 | Serum | III | 28.9 |
| CRC+ | CLSP073/F0 | Serum | III | 16.3 |
| CRC+ | CLSP069/F0 | Serum | III | 9.7 |
| CRC+ | CLSP101/F0 | Serum | III | 18.9 |
| CRC+ | CLSP103/F0 | Serum | III | 7.2 |
| CRC+ | CLSP138/F0 | Serum | III | 8.5 |
| CRC+ | CBSE005/F0 | Serum | III | 21.0 |
| CRC+ | CLSP153/F0 | Serum | III | 47.9 |
| CRC+ | CLSP068/F0 | Serum | IV | 12.3 |
| CRC+ | CBSE026/F0 | Serum | IV | 18.4 |
| CRC+ | CLSP057/F0 | Serum | IV | 31.6 |
| CRC+ | GHBD027/F0 | Serum | IV | 8.4 |
| CRC+ | CBSE021/F0 | Serum | IV | 8.1 |
| CRC+ | CBSE027/F0 | Serum | IV | 16.2 |
| CRC+ | CLSP052/F0 | Serum | IV | 6.9 |
| CRC+ | CLSP068/F0 | Serum | IV | 21.4 |
| CRC+ | CLSP109/F0 | Serum | IV | 97.8 |
| CRC+ | CBSE012/F0 | Serum | IV | 5.0 |
| CRC+ | CLSP079/F0 | Serum | IV | 11.4 |
| CRC+ | CLSP083/F0 | Serum | IV | 9.6 |
| CRC+ | GHBD022/F0 | Serum | IV | 16.8 |
| CRC+ | CLSP095/F0 | Serum | IV | 15.8 |
| CRC+ | CLSP161/F0 | Serum | IV | 13.0 |
| CRC+ | GHBD056/F0 | Serum | IV | 32.3 |
| CRC+ | CB5E027/F0 | Serum | IV | 12.2 |
| CRC+ | CLSP109/F0 | Serum | IV | 99.0 |
| CRC+ | GHBD071/F0 | Serum | IV | 38.0 |
| CRC+ | GHBD030/F0 | Serum | IV | 12.3 |
| CRC+ | CLSP156/F0 | Serum | IV | 11.7 |
| CRC+ | CLSP159/F0 | Serum | IV | 12.5 |
| CRC+ | CLSP042/F0 | Serum | IV | 22.8 |
| CRC+ | CBSE019/F0 | Serum | IV | 19.5 |
| CRC+ | CLSP160/F0 | Serum | IV | 101.8 |
| CRC+ | CLSP132/F0 | Serum | IV | 29.8 |
| CRC+ | CBSE008/F0 | Serum | IV | 4.8 |
| CRC+ | CBSE003/F0 | Serum | IV | 17.1 |
| CRC− | N017250 | Serum | HEALTHY | 4.8 |
| CRC− | N017197 | Serum | HEALTHY | 5.3 |
| CRC− | N018640 | Serum | HEALTHY | 10.0 |
| CRC− | N006586 | Serum | HEALTHY | 4.3 |
| CRC− | N376760 | Serum | HEALTHY | 8.2 |
| CRC− | N750712 | Serum | HEALTHY | 3.8 |
| CRC− | N491415 | Serum | HEALTHY | 7.5 |
| CRC− | N857501 | Serum | HEALTHY | 7.7 |
| CRC− | N858045 | Serum | HEALTHY | 8.9 |
| CRC− | N518518 | Serum | HEALTHY | 7.9 |
| CRC− | N511498 | Serum | HEALTHY | 5.6 |
| CRC− | N858491 | Serum | HEALTHY | 5.2 |
| CRC− | N418724 | Serum | HEALTHY | 3.3 |
| CRC− | N417836 | Serum | HEALTHY | 4.8 |
| CRC− | N318421 | Serum | HEALTHY | 8.9 |
| CRC− | N858037 | Serum | HEALTHY | 5.6 |
| CRC− | N318384 | Serum | HEALTHY | 3.7 |
| CRC− | N418687 | Serum | HEALTHY | 5.2 |
| CRC− | N418556 | Serum | HEALTHY | 9.0 |
| CRC− | N858459 | Serum | HEALTHY | 5.4 |
| CRC− | N519078 | Serum | HEALTHY | 3.5 |
| CRC− | N748049 | Serum | HEALTHY | 3.9 |
| CRC− | N55771- | Serum | HEALTHY | 5.7 |
| CRC− | N37663- | Serum | HEALTHY | 7.3 |
| CRC− | N593167 | Serum | HEALTHY | 5.0 |
| CRC− | N418783 | Serum | HEALTHY | 4.1 |
| CRC− | N49128- | Serum | HEALTHY | 7.2 |
| CRC− | N857704 | Serum | HEALTHY | 4.3 |
| CRC− | N147153 | Serum | HEALTHY | 5.2 |
| CRC− | N146601 | Serum | HEALTHY | 7.8 |
| CRC− | N469716 | Serum | HEALTHY | 4.5 |
| CRC− | N593351 | Serum | HEALTHY | 6.7 |
| CRC− | N519043 | Serum | HEALTHY | 4.4 |
| CRC− | N491247 | Serum | HEALTHY | 7.6 |
| CRC− | N511447 | Serum | HEALTHY | 5.1 |
| CRC− | N836141 | Serum | HEALTHY | 4.3 |
| CRC− | N370537 | Serum | HEALTHY | 6.9 |
| CRC− | N836256 | Serum | HEALTHY | 5.4 |
| CRC− | N557680 | Serum | HEALTHY | 3.1 |
| CRC− | N469740 | Serum | HEALTHY | 5.9 |
| CRC− | N418900 | Serum | HEALTHY | 5.6 |
| CRC− | N836205 | Serum | HEALTHY | 3.7 |
| CRC− | N748153 | Serum | HEALTHY | 5.9 |
| CRC− | N148279 | Serum | HEALTHY | 5.3 |
| CRC− | N511463 | Serum | HEALTHY | 5.0 |

TABLE 6-continued

| Pathological condition[a] | Sample identifier | Nature | Stage | L-FABP ng/ml |
|---|---|---|---|---|
| CRC- | N314420 | Serum | HEALTHY | 6.7 |
| CRC- | N146695 | Serum | HEALTHY | 6.3 |
| CRC- | N318077 | Serum | HEALTHY | 9.4 |
| CRC- | N148340 | Serum | HEALTHY | 7.8 |
| CRC- | N148420 | Serum | HEALTHY | 6.4 |
| CRC- | N491052 | Serum | HEALTHY | 17.0 |
| CRC- | N858088 | Serum | HEALTHY | 6.1 |
| CRC- | N469708 | Serum | HEALTHY | 5.2 |
| CRC- | N593255 | Serum | HEALTHY | 6.5 |
| CRC- | N887815 | Serum | HEALTHY | 6.6 |
| CRC- | N491685 | Serum | HEALTHY | 8.4 |
| CRC- | N511471 | Serum | HEALTHY | 8.5 |
| CRC- | N148316 | Serum | HEALTHY | 9.1 |
| CRC- | N835800 | Serum | HEALTHY | 6.0 |
| CRC- | N440507 | Serum | HEALTHY | 7.8 |
| CRC- | N858467 | Serum | HEALTHY | 6.8 |
| CRC- | N748102 | Serum | HEALTHY | 5.1 |
| CRC- | N325015 | Serum | HEALTHY | 6.3 |
| CRC- | N557699 | Serum | HEALTHY | 5.5 |
| CRC- | N687916 | Serum | HEALTHY | 6.0 |
| CRC- | N557701 | Serum | HEALTHY | 9.1 |
| CRC- | N862239 | Serum | HEALTHY | 5.2 |
| CRC- | N314164 | Serum | HEALTHY | 8.6 |
| CRC- | N858248 | Serum | HEALTHY | 7.8 |
| CRC- | N376904 | Serum | HEALTHY | 4.2 |
| CRC- | N491239 | Serum | HEALTHY | 5.1 |
| CRC- | N83615- | Serum | HEALTHY | 9.3 |
| CRC- | N557760 | Serum | HEALTHY | 14.7 |
| CRC- | N519086 | Serum | HEALTHY | 8.9 |
| CRC- | N836280 | Serum | HEALTHY | 6.9 |
| CRC- | N83586- | Serum | HEALTHY | 4.7 |
| CRC- | N488988 | Serum | HEALTHY | 6.7 |
| CRC- | N518067 | Serum | HEALTHY | 7.5 |
| CRC- | N491079 | Serum | HEALTHY | 13.9 |
| CRC- | N440363 | Serum | HEALTHY | 6.0 |
| CRC- | N748268 | Serum | HEALTHY | 7.6 |
| CRC- | N469775 | Serum | HEALTHY | 7.8 |
| CRC- | N376920 | Serum | HEALTHY | 6.5 |
| CRC- | N491677 | Serum | HEALTHY | 8.4 |
| CRC- | N418994 | Serum | HEALTHY | 5.6 |
| CRC- | N491028 | Serum | HEALTHY | 5.8 |
| CRC- | N491044 | Serum | HEALTHY | 6.2 |
| CRC- | N518059 | Serum | HEALTHY | 11.7 |
| CRC- | N748161 | Serum | HEALTHY | 5.3 |
| CRC- | N858133 | Serum | HEALTHY | 9.7 |
| CRC- | N557736 | Serum | HEALTHY | 3.6 |
| CRC- | N491386 | Serum | HEALTHY | 7.5 |
| CRC- | N527100 | Serum | HEALTHY | 6.3 |
| CRC- | N857552 | Serum | HEALTHY | 9.8 |
| CRC- | N469767 | Serum | HEALTHY | 7.4 |
| CRC- | N518542 | Serum | HEALTHY | 0.0 |
| CRC- | N49806- | Serum | HEALTHY | 7.8 |
| CRC- | N858061 | Serum | HEALTHY | 6.6 |
| CRC- | N491124 | Serum | HEALTHY | 5.6 |
| CRC- | N030068 | Serum | HEALTHY | 6.2 |
| CRC- | N143574 | Serum | HEALTHY | 7.0 |
| CRC- | N836301 | Serum | HEALTHY | 4.3 |
| CRC- | N146636 | Serum | HEALTHY | 14.5 |
| CRC- | N314324 | Serum | HEALTHY | 7.0 |
| CRC- | N491722 | Serum | HEALTHY | 15.2 |
| CRC- | N370510 | Serum | HEALTHY | 5.3 |
| CRC- | N836125 | Serum | HEALTHY | 4.2 |
| CRC- | N836221 | Serum | HEALTHY | 8.0 |
| CRC- | N518569 | Serum | HEALTHY | 9.6 |
| CRC- | N744056 | Serum | HEALTHY | 3.4 |
| CRC- | N148324 | Serum | HEALTHY | 3.3 |
| CRC- | N314199 | Serum | HEALTHY | 2.1 |

[a]CRC+: patients having colorectal cancer/CRC-: healthy individual

FIG. 4 gives the results of this assay. In the serum panel that we tested, 41 patients out of 141 having colorectal cancer have a serum L-FABP concentration of greater than 17 ng/ml, whereas, in the control group, no individual exceeds this value. Among these 41 patients, are 8 patients with stage I colorectal cancer, 8 with stage II colorectal cancer, 13 with stage III colorectal cancer and 12 with stage IV colorectal cancer. The mean serum L-FABP concentration observed for 141 patients with colorectal cancer is 16.6±1.3 ng/ml. The mean value is 6.6±0.2 ng/ml for 112 healthy individuals (negative controls). This difference is statistically significant (P<0.0001, one-sided t-test with Welch's correction for unequal variances).

6. Serum Assay for the I-FABP Tumor Marker

We used an ELISA kit marketed by the company Hycult Biotechnology to assay the human I-FABP protein (Cat. No. HK406). This kit makes it possible to quantify the I-FABP protein in cell culture supernatants or in serum, plasma or urine, in order to determine the presence of ischemic lesions in the small intestine. We followed the procedure recommended by the manufacturer. The assaying of the I-FABP protein can be carried out by alternative techniques, well known to those skilled in the art.

FIG. 5 gives the results of this assay. In the serum panel that we tested, 15 patients out of 40 having colorectal cancer have a serum I-FABP concentration of greater than 40 pg/ml, whereas, in the control group, only 2 individuals out of 24 exceed this value. More clearly, 3 sera of patients having stage I colorectal cancer, 2 sera of patients having stage III colorectal cancer and 1 serum of a patient having stage IV colorectal cancer have a serum I-FABP concentration of greater than 100 pg/ml. No concentration above this value was found in the CRC- control group.

7. Serum Assay for the Apolipoprotein AI Tumor Marker

The assaying of serum Apolipoprotein AI was carried out by means of two different immunoassay techniques. Firstly, we used a microplate sandwich ELISA. The 96-well plates were coated with the anti-Apo AI monoclonal antibody, clone 1404 (Biodesign Cat. No. H45404) at 1 µg per well. After 3 washes with PBS-0.05% Tween 20 (PBS-T), the plates were saturated with 10% milk in PBS-T for 1 h at 37° C. The plates were washed a further 3 times in PBS-T, 100 µl of the dilutions of the standard range or 100 µl of the 1/100 000 dilution of the test serum samples were deposited onto the plates, and the plates were incubated for 2 h at 37° C. The standard range was prepared by diluting the Apo AI protein (Biodesign Cat. No. A50620H) in PBS-T, BSA 1% (1.6 to 100 ng/ml). After 3 washes with PBS-T, the polyclonal detection antibody coupled to horseradish peroxidase (Biodesign Cat. No. K45452P) was added at 0.1 µg per well, and the plates were incubated for 2 h at 37° C. A further 3 washes with PBS-T were carried out, before adding the OptEIA substrate (BD), at 100 µl/well. After 20 min, when the development of the color had taken place, the reaction was stopped with 2N sulfuric acid and the absorbence at 450 nm was measured.

FIG. 6A gives the results of this assay. We demonstrated a decrease in serum concentration of Apo AI in individuals with colorectal cancer. The mean concentration in 38 individuals with stage I to IV CRC is 675±36 µg/ml, whereas it is much higher in 27 healthy individuals (controls): 1040±39 µg/ml. This difference is statistically very significant (P<0.0001, one-sided t-test). By way of comparison, in 13 individuals with liver cancer, the mean serum concentration of Apo AI is 1175±87 µg/ml with the sandwich ELISA technique used. The decrease in the serum concentration demonstrates that Apo AI is therefore a specific marker of colorectal cancer, it being possible for this decrease to be demonstrated by means of an immunoassay.

The second assaying technique that was used is a multiplex assay marketed by the company Linco, which makes it possible to assay several Apolipoproteins, including AI and AII, simultaneously, in the same sample (Cat. No. APO-62K). The procedure recommended by the manufacturer was applied.

FIG. 6B gives the results of this assay. The decrease in the serum concentration of Apo AI in patients with CRC is confirmed with this second technique. The mean concentration of Apo AI in 34 individuals with stage I to IV CRC is 768±30 µg/ml, whereas it is much higher in 17 healthy individuals (controls): 1194±51 µg/ml. This difference is statistically very significant (P<0.0001, one-sided t-test).

8. Serum Assay for the Apolipoprotein AII Tumor Marker

The assaying of serum Apolipoprotein AII was carried out with the Linco multiplex kit. FIG. 7 gives the results of this assay. We demonstrated a decrease in the serum concentration of Apo AII in the individuals with colorectal cancer. The mean concentration of Apo AII in 34 individuals with stage I to IV CRC is 170±11 µg/ml, whereas it is much higher in 17 healthy individuals (controls): 277±16 µg/ml. This difference is statistically very significant (P<0.0001, one-sided t-test).

9. Serum Assay for the I-Plastin Tumor Marker

The I-Plastin protein was assayed using the antibodies described in Example 2 and an ELISA assay using the Vidas® automated device (bioMérieux). To do this, the ELISA assay was constructed using the reagents of the Vidas® HBs Ag Ultra kit (bioMérieux, Cat. No. 30315). The reagents were used as described in the corresponding information sheet (ref. 11728 D-FR-2005/05), with the following modifications:

1. The cones were sensitized with the capture antibody 3D11D10 at a concentration of 15 µg/ml.
2. The content of the second well of the HBs Ag Ultra cartridge was replaced with 300 µl of revealing antibody 8C8C5, coupled to biotin, diluted to 1 µg/ml in the buffer of the second well of the Vidas® HBs Ag Ultra kit (buffer with goat serum and sodium azide at 1 g/l).
3. The serum, plasma or stool samples (100 µl) were diluted directly in the second well of the HBs Ag Ultra cartridge.
4. The ELISA reaction was carried out using the Vidas® automated device and the HBs Ag Ultra protocol.
5. The results were obtained in the form of crude values after subtraction of the background noise (reading of the substrate before reaction).

The concentration of the tumor marker present in the body fluid to be assayed (blood, serum, plasma, stool) was calculated according to the procedure described in paragraph 2 regarding the assaying of LEI.

The amounts obtained for the patients analyzed are reported in FIG. 8. The 2 sera of patients having colorectal cancer who were tested show a clear increase in their amount of serum I-Plastin.

10. Serum Assay for the Group-B, ACE, CA19-9 and Galectin-3 Tumor Markers

The Beta2-Microglobulin, ACE, CA19-9 and Testosterone tumor markers were assayed using the assay kits of the applicant, respectively Vidas® β2-microglobulin, Vidas® ACE, Vidas® CA19-9™ and Vidas® Testosterone, according to the procedure specific to each kit.

The E-Cadherin protein was assayed using the E-Cadherin EIA kit (Takara Biochemicals, Tokyo, Japan) according to the procedure of the kit.

The Regenerating Islet-Derived Protein 3 Alpha protein, otherwise known as Pancreatitis Associated Protein (PAP1), was assayed using the PANCREPAP ELISA kit (DynaBio, Marseilles, France) according to the procedure of the kit.

The Galectin-3 and LDH proteins were assayed using the antibodies described in Example 2. The Proteasome 20 S was assayed using the antibodies described in patent EP 0434670. To do this, the ELISA assays were constructed using the Vidas® automated device (bioMérieux) and the reagents of the Vidas® HBs Ag Ultra kit (bioMérieux, Cat. No. 30315). The reagents were used as described in the corresponding information sheet (ref. 11728 D-FR-2005/05), with the following modifications:

1. The cones were sensitized with the capture antibody at a concentration of between 5 and 30 µg/ml.
2. The content of the second well of the HBs Ag Ultra cartridge was replaced with 300 µl of revealing antibody, coupled to biotin, diluted to 1 µg/ml in buffer with goat serum and sodium azide at 1 g/l.
3. The serum, plasma or stool samples were diluted directly in the second well of the HBs Ag Ultra cartridge after, if necessary, a dilution in buffer of the second well.
4. The ELISA reaction was carried out using the Vidas® automated device and the HBs Ag Ultra protocol. The step of incubating the sample with the capture and revealing antibodies was between 14 and 100 cycles.
5. The results were obtained in the form of crude values after subtraction of the background noise (reading of the substrate before reaction).

The concentration of the tumor marker present in the body fluid to be assayed (blood, serum, plasma, stool) was calculated according to the procedure described in paragraph 2 regarding the assaying of LEI. The assay conditions for various tumor markers have been reproduced in Table 7.

TABLE 7

| Protein | Galectin-3 | LDH-B | Proteasome 20 S |
|---|---|---|---|
| Capture antibody | 12F8A12 at 15 µg/mL | 3F11E11 at 10 µg/mL | GD6 at 30 µg/mL |
| Revealing antibody | 14A5G1 | 12F10G8 | 7A11 |
| Goat Serum in dilution buffer | with | with | without |
| Stool volume | 50 µL | 50 µL | 200 µL |
| Serum volume | 50 µL | 50 µL | 100 µL |
| Sample deposit | $2^{nd}$ well | $2^{nd}$ well | $1^{st}$ well |
| Incubation time | 100 cycles | 14 cycles | 14 cycles |

The amounts obtained for the patients analyzed with the Beta2-Microglobulin, ACE, CA19-9, Testosterone, E-Cadherin, Regenerating Islet-Derived Protein 3 Alpha, Galectin-3, LDH and Proteasome 20S tumor markers have been reported respectively in FIGS. 9 to 17.

Three sera of patients having colorectal cancer show an increase in their amount of serum β2-microglobulin.

Ten sera of patients having colorectal cancer show an increase in their amount of serum ACE. More clearly, 1 serum of a patient having stage III colorectal cancer and 7 sera of patients having stage IV colorectal cancer show a considerable increase in their amount of serum ACE.

Nine sera of patients having colorectal cancer show an increase in their amount of serum CA 19-9. More clearly, 1 serum of a patient having stage III colorectal cancer and 7 sera of patients having stage IV colorectal cancer show a considerable increase in their amount of serum CA 19-9.

Ten sera of patients having colorectal cancer show a decrease in their amount of serum Testosterone. More clearly, 1 serum of a patient having stage II colorectal cancer, 1 serum of a patient having stage III colorectal cancer and 2 sera of patients having stage IV colorectal cancer show a fall in their amount of serum testosterone.

Two sera of patients having colorectal cancer show an increase in their amount of serum Regenerating Islet-Derived Protein 3 Alpha.

Four sera of patients having stage IV colorectal cancer, 2 sera of patients having stage III colorectal cancer and 1 serum of a patient having stage II colorectal cancer show a clear increase in their amount of serum Galectin-3.

EXAMPLE 4: USE OF THE SERUM ASSAYS FOR TUMOR MARKERS IN COMBINATION

The applicant showed in Example 3 that abnormally elevated or abnormally reduced amounts of tumor markers could be observed in the bloodstream of certain patients having colorectal cancer. Surprisingly, the increase or the decrease in the amount, in the blood, of two given markers is not systematically observed in the same patients. As a result, the combination of several tumor markers makes it possible to increase the number of patients identified as having colorectal cancer. Thus, a patient A may present an increase or a decrease in one or more tumor markers (group X), it being possible for said markers of group X to be normal in a patient B; in this same patient B, one or more other tumor markers (group Y) may be elevated or reduced, it being possible for said markers of group Y to be normal in patient A.

The various tumor markers assayed by the applicant may thus be combined by means of various mathematical algorithms well known to those skilled in the art. By way of illustration, and without this example being exhaustive in nature, the following method was carried out:

1. A threshold value was set for each tumor marker.
2. When the amount of the tumor marker in the blood was increased in the case of colorectal cancer, the amount in the blood, obtained for a given patient, was divided by its threshold value. When the amount of the tumor marker in the blood was decreased in the case of colorectal cancer, the amount in the blood, obtained for a given patient, was inverted and then multiplied by its threshold value.
3. When the "amount in the blood divided by threshold value" ratio was greater than 1, the ratio was multiplied by a coefficient, for example 10. The value thus obtained was named the "score", for the patient studied, for the tumor marker under consideration.
4. The scores obtained for various tumor markers were added, with them being weighted by a factor specific to each marker. In the case of the example below, all the weighting factors were set at 1.
5. The sum of the scores was divided by the total number of scores added, and the value thus obtained was named the "total score".
6. The patient is diagnosed as having colorectal cancer when his or her total score is increased relative to a threshold score.

The total scores for a selection of 2, 3, 4, 5, 8 and 9 markers comprising L-FABP are given in Table 8.

The combination of the L-FABP and LEI tumor markers thus makes it possible to obtain, for the same group of 79 patients, increased total scores "2" in 29 patients having colorectal cancer, whereas assaying L-FABP or LEI alone showed an increase, respectively, in 27 and 4 patients only.

The combination of the L-FABP, ACE and CA19-9 tumor markers thus makes it possible to obtain, for the same group of 79 patients, increased total scores "3" in 48 patients having colorectal cancer, whereas assaying L-FABP, ACE or CA19-9 alone showed an increase, respectively, in 27, 23 and 12 patients only.

The combination of the L-FABP, ACE, CA19-9 and Gal-3 tumor markers thus makes it possible to obtain, for the same group of 79 patients, increased total scores "4c" in 50 patients having colorectal cancer, whereas assaying L-FABP, ACE, CA19-9 or Gal-3 alone showed an increase, respectively, in 27, 23, 12 and 10 patients only.

The combination of the L-FABP, ACE, LEI and Aminoacylase 1 tumor markers thus makes it possible to obtain, for the same group of 79 patients, increased total scores "4d" in 46 patients having colorectal cancer, whereas assaying L-FABP, ACE, LEI or Aminoacylase 1 alone showed an increase, respectively, in 27, 23, 4 and 3 patients only.

The combination of the L-FABP, ACE, CA19-9 and ApoA1 tumor markers thus makes it possible to obtain, for the same group of 79 patients, increased total scores "4e" in 51 patients having colorectal cancer, whereas assaying L-FABP, ACE or CA19-9 alone showed an increase, respectively, in 27, 23 and 12 patients only, and assaying ApoA1 alone showed a decrease in 3 patients only.

The combination of the L-FABP, ACE, CA19-9 and LEI tumor markers thus makes it possible to obtain, for the same group of 79 patients, increased total scores "4f" in 50 patients having colorectal cancer, whereas assaying L-FABP, ACE, CA19-9 or LEI alone showed an increase, respectively, in 27, 23, 12 and 4 patients only.

The combination of the L-FABP, ACE, CA19-9, LEI and ACY tumor markers thus makes it possible to obtain, for the same group of 79 patients, increased total scores "5" in 50 patients having colorectal cancer, whereas assaying L-FABP, ACE, CA19-9, LEI or ACY alone showed an increase, respectively, in 27, 23, 12, 4 and 3 patients only.

The combination of the L-FABP, ACE, LEI, ACY, Beta2-Microglobulin, Proteasome 20S, PAP and E-Cadherin tumor markers thus makes it possible to obtain, for the same group of 79 patients, increased total scores "8" in 52 patients having colorectal cancer, whereas assaying L-FABP, ACE, LEI, ACY, Beta2-Microglobulin, Proteasome 20S, PAP or E-Cadherin alone showed an increase, respectively, in 27, 23, 4, 3, 8, 5, 6 and 1 patient(s) only.

The combination of the L-FABP, ACE, CA19-9, LEI, ACY, Beta2-Microglobulin, Proteasome 20S, PAP and E-Cadherin tumor markers thus makes it possible to obtain, for the same group of 79 patients, increased total scores "91" in 55 patients having colorectal cancer, whereas assaying L-FABP, ACE, CA19-9, LEI, ACY, Beta2-Microglobulin, Proteasome 20S, PAP or E-Cadherin alone showed an increase, respectively, in 27, 23, 12, 4, 3, 8, 5, 6 and 1 patient(s) only.

The combination of the L-FABP, ACE, CA19-9, LEI, ACY, Beta2-Microglobulin, Proteasome 20S, Gal-3 and ApoA1 tumor markers thus makes it possible to obtain, for the same group of 79 patients, increased total scores "9j" in 60 patients having colorectal cancer, whereas assaying L-FABP, ACE, CA19-9, LEI, ACY, Beta2-Microglobulin, Proteasome 20S or Gal-3 alone showed an increase, respectively, in 27, 23, 12, 4, 3, 8, 5 and 10 patients only, and assaying ApoA1 alone showed a decrease in 3 patients only.

TABLE 8

| Pathological condition | Sample identifier | Stage | L-FABP ng/ml | Total score 2[a] | Total score 3[b] | Total score 4[c] | Total score 4[d] | Total score 4[e] | Total score 4[f] | Total score 5[g] | Total score 8[h] | Total score 9[i] | Total score 9[j] |
|---|---|---|---|---|---|---|---|---|---|---|---|---|---|
| Healthy individual | N017250 | | 4.77 | 0.19 | 0.19 | 0.19 | 0.17 | 0.19 | 0.17 | 0.17 | 0.38 | 0.33 | 0.17 |
| Healthy individual | N017197 | | 5.26 | 0.20 | 0.28 | 0.28 | 0.25 | 0.25 | 0.23 | 0.23 | 0.25 | 0.23 | 0.23 |
| Healthy individual | N018640 | | 10.01 | 0.33 | 0.29 | 0.22 | 0.26 | 0.29 | 0.24 | 0.24 | 0.34 | 0.30 | 0.19 |
| Healthy individual | N006586 | | 4.32 | 0.37 | 0.51 | 0.42 | 0.27 | 0.51 | 0.50 | 0.41 | 0.23 | 0.35 | 0.32 |
| Healthy individual | N376760 | | 8.21 | 0.46 | 0.62 | 0.67 | 0.42 | 0.62 | 0.58 | 0.46 | 0.38 | 0.43 | 0.48 |
| Healthy individual | N750712 | | 3.78 | 0.13 | 0.26 | 0.27 | 0.13 | 0.26 | 0.21 | 0.17 | 0.14 | 0.17 | 0.19 |
| Healthy individual | N491415 | | 7.53 | 0.24 | 0.22 | 0.26 | 0.14 | 0.22 | 0.17 | 0.16 | 0.14 | 0.15 | 0.18 |
| Healthy individual | N857501 | | 7.65 | 0.29 | 0.43 | 0.40 | 0.30 | 0.43 | 0.35 | 0.28 | 0.28 | 0.27 | 0.28 |
| Healthy individual | N858045 | | 8.90 | 0.52 | 0.25 | 0.29 | 0.27 | 0.25 | 0.31 | 0.25 | 0.24 | 0.23 | 0.26 |
| Healthy individual | N518518 | | 7.95 | 0.48 | 0.35 | 0.28 | 0.35 | 0.35 | 0.38 | 0.31 | 0.30 | 0.27 | 0.24 |
| Healthy individual | N511498 | | 5.63 | 0.19 | 0.23 | 0.21 | 0.15 | 0.23 | 0.18 | 0.15 | 0.14 | 0.14 | 0.14 |
| Healthy individual | N858491 | | 5.23 | 0.18 | 0.15 | 0.24 | 0.12 | 0.15 | 0.13 | 0.11 | 0.11 | 0.11 | 0.16 |
| Healthy individual | N418724 | | 3.32 | 0.25 | 0.11 | 0.15 | 0.14 | 0.11 | 0.16 | 0.12 | 0.16 | 0.14 | 0.17 |
| Healthy individual | N417836 | | 4.82 | 0.33 | 0.19 | 0.32 | 0.22 | 0.19 | 0.24 | 0.19 | 0.26 | 0.23 | 0.30 |
| Healthy individual | N318421 | | 8.89 | 0.36 | 0.40 | 0.49 | 0.33 | 0.40 | 0.35 | 0.28 | 0.33 | 0.29 | 0.36 |
| Healthy individual | N858037 | | 5.61 | 0.40 | 0.17 | 0.31 | 0.23 | 0.17 | 0.24 | 0.19 | 0.25 | 0.21 | 0.29 |
| Healthy individual | N318384 | | 3.74 | 0.23 | 0.20 | 0.27 | 0.21 | 0.20 | 0.21 | 0.17 | 0.26 | 0.22 | 0.25 |
| Healthy individual | N418687 | | 5.22 | 0.41 | 0.21 | 0.25 | 0.28 | 0.21 | 0.29 | 0.23 | 0.32 | 0.27 | 0.28 |
| Healthy individual | N418556 | | 9.02 | 0.52 | 0.24 | 0.32 | 0.30 | 0.24 | 0.30 | 0.24 | 0.33 | 0.28 | 0.33 |
| Healthy individual | N858459 | | 5.37 | 0.18 | 0.38 | 0.35 | 0.32 | 0.38 | 0.29 | 0.26 | 0.29 | 0.25 | 0.25 |
| Healthy individual | N519078 | | 3.50 | 0.35 | 0.08 | 0.16 | 0.18 | 0.08 | 0.18 | 0.14 | 0.18 | 0.15 | 0.19 |
| Healthy individual | N748049 | | 3.92 | 0.13 | 0.49 | 0.41 | 0.12 | 0.49 | 0.37 | 0.30 | 0.12 | 0.26 | 0.25 |
| Healthy individual | N55771- | | 5.69 | 0.35 | 0.52 | 0.47 | 0.24 | 0.52 | 0.48 | 0.39 | 0.24 | 0.36 | 0.36 |
| Healthy individual | N37663- | | 7.25 | 0.36 | 0.55 | 0.56 | 0.26 | 0.55 | 0.48 | 0.39 | 0.30 | 0.40 | 0.42 |
| Healthy individual | N593167 | | 5.04 | 0.33 | 0.37 | 0.46 | 0.25 | 0.37 | 0.36 | 0.31 | 0.25 | 0.30 | 0.37 |
| Healthy individual | N418783 | | 4.12 | 0.37 | 0.32 | 0.35 | 0.22 | 0.32 | 0.37 | 0.29 | 0.30 | 0.34 | 0.36 |
| Healthy individual | N49128- | | 7.24 | 0.31 | 0.38 | 0.45 | 0.43 | 0.35 | 0.33 | 0.46 | 0.52 | 0.52 | 0.51 |
| Healthy individual | N857704 | | 4.32 | 0.34 | 0.31 | 0.37 | 0.22 | 0.27 | 0.34 | 0.27 | 0.22 | 0.26 | 0.28 |
| Healthy individual | N147153 | | 5.21 | 0.31 | 0.29 | 0.32 | 0.19 | 0.29 | 0.29 | 0.23 | 0.27 | 0.29 | 0.31 |
| Healthy individual | N146601 | | 7.81 | 0.47 | 0.42 | 0.48 | 0.34 | 0.42 | 0.43 | 0.35 | 0.36 | 0.36 | 0.40 |
| Healthy individual | N469716 | | 4.45 | 0.35 | 0.29 | 0.32 | 0.25 | 0.29 | 0.33 | 0.26 | 0.25 | 0.26 | 0.28 |
| Healthy individual | N593351 | | 6.75 | 0.54 | 0.40 | 0.50 | 0.42 | 0.40 | 0.47 | 0.38 | 0.43 | 0.40 | 0.45 |
| Healthy individual | N519043 | | 4.39 | 0.31 | 0.20 | 0.21 | 0.19 | 0.20 | 0.24 | 0.20 | 0.18 | 0.18 | 0.19 |
| Healthy individual | N491247 | | 7.62 | 0.33 | 0.34 | 0.39 | 0.26 | 0.34 | 0.30 | 0.24 | 0.29 | 0.27 | 0.31 |
| Healthy individual | N511447 | | 5.06 | 0.31 | 0.20 | 0.34 | 0.19 | 0.20 | 0.23 | 0.18 | 0.20 | 0.19 | 0.27 |
| Healthy individual | N836141 | | 4.29 | 0.40 | 0.15 | 0.16 | 0.21 | 0.18 | 0.25 | 0.20 | 0.20 | 0.20 | 0.20 |
| Healthy individual | N370537 | | 6.87 | 0.25 | 0.25 | 0.34 | 0.17 | 0.21 | 0.21 | 0.17 | 0.19 | 0.18 | 0.23 |
| Healthy individual | N836256 | | 5.40 | 0.40 | 0.22 | 0.33 | 0.25 | 0.37 | 0.29 | 0.23 | 0.25 | 0.23 | 0.36 |

TABLE 8-continued

| Pathological condition | Sample identifier | Stage | L-FABP ng/ml | Total score 2$^a$ | Total score 3$^b$ | Total score 4$^c$ | Total score 4$^d$ | Total score 4$^e$ | Total score 4$^f$ | Total score 5$^g$ | Total score 8$^h$ | Total score 9$^i$ | Total score 9$^j$ |
|---|---|---|---|---|---|---|---|---|---|---|---|---|---|
| Healthy individual | N557680 | | 3.09 | 0.35 | 0.19 | 0.28 | 0.23 | 0.19 | 0.27 | 0.22 | 0.22 | 0.20 | 0.25 |
| Healthy individual | N469740 | | 5.93 | 0.44 | 0.23 | 0.31 | 0.27 | 0.23 | 0.31 | 0.25 | 0.30 | 0.27 | 0.31 |
| Healthy individual | N418900 | | 5.56 | 0.30 | 0.21 | 0.28 | 0.19 | 0.21 | 0.22 | 0.18 | 0.23 | 0.21 | 0.25 |
| Healthy individual | N836205 | | 3.68 | 0.42 | 0.13 | 0.10 | 0.22 | 0.32 | 0.25 | 0.20 | 0.20 | 0.19 | 0.26 |
| Healthy individual | N748153 | | 5.88 | 0.31 | 0.21 | 0.26 | 0.21 | 0.25 | 0.23 | 0.20 | 0.23 | 0.22 | 0.26 |
| Healthy individual | N148279 | | 5.30 | 0.41 | 0.20 | 0.27 | 0.24 | 0.20 | 0.28 | 0.22 | 0.27 | 0.24 | 0.28 |
| Healthy individual | N511463 | | 5.05 | 0.32 | 0.16 | 0.24 | 0.18 | 0.25 | 0.21 | 0.17 | 0.16 | 0.16 | 0.24 |
| Healthy individual | N314420 | | 6.67 | 0.22 | 0.23 | 0.25 | 0.18 | 0.23 | 0.19 | 0.17 | 0.22 | 0.20 | 0.21 |
| Healthy individual | N146695 | | 6.31 | 0.37 | 0.17 | 0.22 | 0.20 | 0.17 | 0.22 | 0.18 | 0.25 | 0.23 | 0.25 |
| Healthy individual | N318077 | | 9.39 | 0.41 | 0.31 | 0.38 | 0.28 | 0.31 | 0.30 | 0.24 | 0.34 | 0.30 | 0.34 |
| Healthy individual | N148340 | | 7.75 | 0.29 | 0.20 | 0.23 | 0.16 | 0.20 | 0.18 | 0.14 | 0.19 | 0.18 | 0.20 |
| Healthy individual | N148420 | | 6.44 | 0.29 | 0.18 | 0.33 | 0.16 | 0.18 | 0.18 | 0.14 | 0.20 | 0.18 | 0.27 |
| Healthy individual | N491052 | | 16.96 | 0.73 | 0.36 | 0.43 | 0.37 | 0.41 | 0.38 | 0.31 | 0.40 | 0.34 | 0.41 |
| Healthy individual | N858088 | | 6.14 | 0.21 | 0.17 | 0.14 | 0.15 | 0.17 | 0.14 | 0.13 | 0.14 | 0.12 | 0.12 |
| Healthy individual | N469708 | | 5.23 | 0.45 | 0.22 | 0.28 | 0.30 | 0.22 | 0.32 | 0.25 | 0.36 | 0.31 | 0.33 |
| Healthy individual | N593255 | | 6.52 | 0.69 | 0.22 | 0.25 | 0.42 | 0.22 | 0.42 | 0.35 | 0.37 | 0.32 | 0.32 |
| Healthy individual | N887815 | | 6.58 | 0.21 | 0.17 | 0.14 | 0.14 | 0.17 | 0.13 | 0.12 | 0.11 | 0.10 | 0.09 |
| Healthy individual | N491685 | | 8.39 | 0.36 | 0.25 | 0.36 | 0.23 | 0.25 | 0.24 | 0.19 | 0.23 | 0.20 | 0.27 |
| Healthy individual | N511471 | | 8.46 | 0.48 | 0.24 | 0.24 | 0.28 | 0.22 | 0.29 | 0.23 | 0.25 | 0.22 | 0.22 |
| Healthy individual | N148316 | | 9.05 | 0.41 | 0.21 | 0.26 | 0.22 | 0.21 | 0.23 | 0.19 | 0.24 | 0.21 | 0.23 |
| Healthy individual | N835800 | | 5.99 | 0.41 | 0.21 | 0.29 | 0.26 | 0.29 | 0.27 | 0.22 | 0.24 | 0.21 | 0.29 |
| Healthy individual | N440507 | | 7.82 | 0.48 | 0.24 | 0.41 | 0.32 | 0.24 | 0.31 | 0.26 | 0.42 | 0.35 | 0.43 |
| Healthy individual | N858467 | | 6.76 | 0.22 | 0.47 | 0.38 | 0.41 | 0.47 | 0.36 | 0.33 | 0.36 | 0.30 | 0.27 |
| Healthy individual | N748102 | | 5.10 | 0.29 | 0.48 | 0.46 | 0.31 | 0.48 | 0.43 | 0.39 | 0.30 | 0.36 | 0.38 |
| Healthy individual | N325015 | | 6.25 | 0.28 | 0.48 | 0.43 | 0.25 | 0.39 | 0.41 | 0.33 | 0.25 | 0.32 | 0.29 |
| Healthy individual | N557699 | | 5.52 | 0.40 | 0.43 | 0.42 | 0.29 | 0.35 | 0.44 | 0.35 | 0.26 | 0.32 | 0.30 |
| Healthy individual | N687916 | | 5.98 | 0.29 | 0.42 | 0.42 | 0.24 | 0.36 | 0.37 | 0.30 | 0.23 | 0.28 | 0.29 |
| Healthy individual | N557701 | | 9.06 | 0.44 | 0.37 | 0.42 | 0.26 | 0.48 | 0.36 | 0.29 | 0.25 | 0.28 | 0.38 |
| Healthy individual | N862239 | | 5.16 | 0.32 | 0.36 | 0.33 | 0.25 | 0.36 | 0.35 | 0.28 | 0.24 | 0.27 | 0.27 |
| Healthy individual | N314164 | | 8.62 | 0.37 | 0.33 | 0.40 | 0.22 | 0.27 | 0.31 | 0.25 | 0.28 | 0.29 | 0.31 |
| Healthy individual | N858248 | | 7.82 | 0.29 | 0.33 | 0.36 | 0.20 | 0.30 | 0.28 | 0.22 | 0.18 | 0.21 | 0.23 |
| Healthy individual | N376904 | | 4.17 | 0.29 | 0.19 | 0.20 | 0.16 | 0.16 | 0.22 | 0.18 | 0.22 | 0.23 | 0.22 |
| Healthy individual | N491239 | | 5.10 | 0.27 | 0.25 | 0.24 | 0.20 | 0.26 | 0.25 | 020 | 0.27 | 0.26 | 0.26 |
| Healthy individual | N83615- | | 9.28 | 0.46 | 0.30 | 0.28 | 0.27 | 0.34 | 0.32 | 0.25 | 0.25 | 0.24 | 0.27 |
| Healthy individual | N557760 | | 14.65 | 0.50 | 0.41 | 0.47 | 0.29 | 0.51 | 0.34 | 0.27 | 0.27 | 0.26 | 0.38 |
| Healthy individual | N519086 | | 8.94 | 0.46 | 0.29 | 0.33 | 0.27 | 0.26 | 0.31 | 0.25 | 0.26 | 0.25 | 0.26 |
| Healthy individual | N836280 | | 6.85 | 0.42 | 0.20 | 0.15 | 0.21 | 0.25 | 0.26 | 0.21 | 0.19 | 0.19 | 0.20 |
| Healthy individual | N83586- | | 4.75 | 0.42 | 0.21 | 0.17 | 0.25 | 0.20 | 0.30 | 0.24 | 0.24 | 0.23 | 0.20 |

TABLE 8-continued

| Pathological condition | Sample identifier | Stage | L-FABP ng/ml | Total score 2[a] | Total score 3[b] | Total score 4[c] | Total score 4[d] | Total score 4[e] | Total score 4[f] | Total score 5[g] | Total score 8[h] | Total score 9[i] | Total score 9[j] |
|---|---|---|---|---|---|---|---|---|---|---|---|---|---|
| Healthy individual | N488988 | | 6.68 | 0.31 | 0.26 | 0.28 | 0.21 | 0.38 | 0.25 | 0.20 | 0.24 | 0.23 | 0.31 |
| Healthy individual | N518067 | | 7.45 | 0.42 | 0.32 | 0.30 | 0.31 | 0.32 | 0.34 | 0.27 | 0.31 | 0.28 | 0.28 |
| Healthy individual | N491079 | | 13.85 | 0.45 | 0.36 | 0.33 | 0.28 | 0.36 | 0.29 | 0.25 | 0.32 | 0.29 | 0.28 |
| Healthy individual | N440363 | | 6.02 | 0.42 | 0.23 | 0.35 | 0.27 | 0.28 | 0.30 | 0.24 | 0.31 | 0.27 | 0.35 |
| Healthy individual | N748268 | | 7.59 | 0.31 | 0.24 | 0.20 | 0.20 | 0.27 | 0.22 | 0.18 | 0.23 | 0.20 | 0.21 |
| Healthy individual | N469775 | | 7.82 | 0.47 | 0.24 | 0.30 | 0.28 | 0.37 | 0.30 | 0.24 | 0.31 | 0.27 | 0.36 |
| Healthy individual | N376920 | | 6.49 | 0.24 | 0.21 | 0.29 | 0.16 | 0.18 | 0.18 | 0.15 | 0.23 | 0.21 | 0.23 |
| Healthy individual | N491677 | | 8.44 | 0.34 | 0.25 | 0.18 | 0.25 | 0.23 | 0.23 | 0.22 | 0.25 | 0.22 | 0.19 |
| Healthy individual | N418994 | | 5.55 | 0.29 | 0.18 | 0.23 | 0.18 | 0.22 | 0.20 | 0.16 | 0.21 | 0.19 | 0.23 |
| Healthy individual | N491028 | | 5.78 | 0.32 | 0.19 | 0.28 | 0.20 | 0.36 | 0.22 | 0.17 | 0.25 | 0.22 | 0.34 |
| Healthy individual | N491044 | | 6.20 | 0.32 | 0.20 | 0.25 | 0.20 | 0.34 | 0.22 | 0.17 | 0.21 | 0.19 | 0.29 |
| Healthy individual | N518059 | | 11.71 | 0.57 | 0.29 | 0.39 | 0.31 | 0.29 | 0.33 | 0.26 | 0.28 | 0.24 | 0.30 |
| Healthy individual | N748161 | | 5.32 | 0.26 | 0.17 | 0.27 | 0.17 | 0.18 | 0.18 | 0.15 | 0.18 | 0.16 | 0.21 |
| Healthy individual | N858133 | | 9.67 | 0.55 | 0.22 | 0.36 | 0.29 | 0.39 | 0.30 | 0.24 | 0.27 | 0.23 | 0.39 |
| Healthy individual | N557736 | | 3.57 | 0.20 | 0.32 | 0.34 | 0.52 | 0.28 | 0.28 | 0.43 | 0.46 | 0.39 | 0.37 |
| Healthy individual | N491386 | | 7.48 | 0.40 | 0.16 | 0.21 | 0.21 | 0.18 | 0.21 | 0.18 | 0.26 | 0.22 | 0.24 |
| Healthy individual | N527100 | | 6.27 | 0.39 | 0.14 | 0.19 | 0.25 | 0.15 | 0.21 | 0.20 | 0.24 | 0.20 | 0.22 |
| Healthy individual | N857552 | | 9.79 | 0.39 | 0.31 | 0.29 | 0.28 | 0.48 | 0.28 | 0.22 | 0.31 | 0.26 | 0.35 |
| Healthy individual | N469767 | | 7.41 | 0.43 | 0.22 | 0.27 | 0.27 | 0.38 | 0.27 | 0.22 | 0.33 | 0.28 | 0.37 |
| Healthy individual | N518542 | | 0.00 | 0.14 | 0.05 | 0.09 | 0.11 | 0.21 | 0.11 | 0.09 | 0.11 | 0.10 | 0.18 |
| Healthy individual | N49806- | | 7.77 | 0.43 | 0.20 | 0.26 | 0.25 | 0.31 | 0.25 | 0.20 | 0.23 | 0.20 | 0.28 |
| Healthy individual | N858061 | | 6.55 | 0.61 | 0.22 | 0.40 | 0.38 | 0.30 | 0.38 | 0.30 | 0.35 | 0.29 | 0.40 |
| Healthy individual | N491124 | | 5.63 | 0.22 | 0.31 | 0.29 | 0.18 | 0.31 | 0.26 | 0.22 | 0.21 | 0.23 | 0.23 |
| Healthy individual | N030068 | | 6.20 | 0.27 | 0.33 | 0.31 | 0.26 | 0.33 | 0.29 | 0.24 | 0.36 | 0.33 | 0.25 |
| Healthy individual | N143574 | | 7.02 | 0.25 | 0.37 | 0.37 | 0.27 | 0.37 | 0.30 | 0.24 | 0.44 | 0.40 | 0.38 |
| Healthy individual | N836301 | | 4.34 | 0.26 | 0.26 | 0.34 | 0.23 | 0.26 | 0.26 | 0.20 | 0.57 | 0.51 | 0.44 |
| Healthy individual | N146636 | | 14.49 | 0.64 | 0.35 | 0.51 | 0.35 | 0.35 | 0.37 | 0.30 | 0.49 | 0.43 | 0.50 |
| Healthy individual | N314324 | | 7.03 | 0.24 | 0.27 | 0.20 | 0.16 | 0.27 | 0.22 | 0.19 | 0.43 | 0.41 | 0.28 |
| Healthy individual | N491722 | | 15.21 | 0.63 | 0.39 | 0.29 | 0.39 | 0.39 | 0.38 | 0.34 | 0.42 | 0.38 | 0.32 |
| Healthy individual | N370510 | | 5.34 | 0.20 | 0.32 | 0.30 | 0.23 | 0.32 | 0.26 | 0.21 | 0.36 | 0.33 | 0.27 |
| Healthy individual | N836125 | | 4.22 | 0.45 | 0.13 | 0.13 | 0.23 | 0.13 | 0.26 | 0.21 | 0.32 | 0.30 | 0.29 |
| Healthy individual | N836221 | | 7.98 | 0.28 | 0.33 | 0.35 | 0.24 | 0.33 | 0.27 | 0.22 | 0.36 | 0.33 | 0.34 |
| Healthy individual | N518569 | | 9.64 | 0.30 | 0.29 | 0.29 | 0.20 | 0.29 | 0.23 | 0.19 | 0.45 | 0.41 | 0.30 |
| Healthy individual | N744056 | | 3.37 | 0.16 | 0.33 | 0.33 | 0.14 | 0.33 | 0.28 | 0.23 | 0.32 | 0.35 | 0.30 |
| Healthy individual | N148324 | | 3.33 | 0.16 | 0.20 | 0.26 | 0.13 | 0.20 | 0.18 | 0.15 | 0.41 | 0.38 | 0.35 |
| Healthy individual | N314199 | | 2.10 | 0.08 | 0.21 | 0.23 | 0.13 | 0.21 | 0.17 | 0.14 | 0.30 | 0.29 | 0.19 |
| Benign T. | CLSP148 | | 5.73 | 0.22 | 0.15 | 0.25 | 0.12 | 0.15 | 0.14 | 0.11 | 0.19 | 0.17 | 0.22 |
| Benign T. | CLSP149 | | 111.39 | 32.90 | 21.93 | 16.50 | 16.46 | 21.93 | 16.47 | 13.18 | 13.22 | 11.02 | 9.48 |
| Benign T. | CLSP108 | | 4.34 | 0.17 | 0.12 | 0.19 | 0.12 | 0.12 | 0.11 | 0.10 | 0.18 | 0.16 | 0.19 |
| Benign T. | CLSP120 | | 8.41 | 0.29 | 0.18 | 0.23 | 0.16 | 0.18 | 0.16 | 0.13 | 0.18 | 0.15 | 0.18 |
| Benign T. | CLSP116 | | 17.64 | 5.26 | 3.74 | 2.92 | 2.73 | 3.74 | 2.83 | 2.27 | 2.27 | 1.96 | 1.75 |

TABLE 8-continued

| Pathological condition | Sample identifier | Stage | L-FABP ng/ml | Total score 2[a] | Total score 3[b] | Total score 4[c] | Total score 4[d] | Total score 4[e] | Total score 4[f] | Total score 5[g] | Total score 8[h] | Total score 9[i] | Total score 9[j] |
|---|---|---|---|---|---|---|---|---|---|---|---|---|---|
| Benign T. | CLSP142 | | 6.55 | 0.32 | 0.27 | 0.25 | 0.27 | 0.27 | 0.27 | 0.21 | 0.27 | 0.23 | 0.22 |
| Benign T. | CLSP099 | | 17.72 | 5.25 | 3.59 | 2.81 | 2.74 | 3.59 | 2.70 | 2.19 | 2.26 | 1.88 | 1.68 |
| Benign T. | CLSP055 | | 5.74 | 0.24 | 0.17 | 0.22 | 0.16 | 0.17 | 0.16 | 0.13 | 0.16 | 0.13 | 0.17 |
| Benign T. | CLSP061 | | 10.96 | 0.37 | 0.39 | 0.37 | 0.20 | 0.39 | 0.32 | 0.25 | 0.22 | 0.26 | 0.26 |
| CRC+ | CLSP104 | 0 | 10.91 | 0.46 | 4.45 | 3.48 | 0.29 | 4.45 | 3.40 | 2.72 | 0.38 | 2.39 | 2.13 |
| CRC+ | CBSE025 | I | 14.10 | 0.58 | 0.51 | 0.51 | 0.41 | 0.51 | 0.46 | 0.37 | 0.37 | 0.34 | 0.34 |
| CRC+ | CLSP146 | I | 21.72 | 6.57 | 4.42 | 3.49 | 3.32 | 3.44 | 3.40 | 2.72 | 2.76 | 2.35 | 1.91 |
| CRC+ | CBSE011 | I | 10.30 | 0.57 | 0.25 | 0.25 | 0.31 | 0.27 | 0.32 | 0.26 | 0.27 | 0.24 | 0.25 |
| CRC+ | CLSP067 | I | 20.99 | 6.28 | 4.18 | 3.23 | 3.18 | 4.18 | 3.19 | 2.55 | 2.56 | 2.14 | 1.89 |
| CRC+ | CLSP118 | I | 7.10 | 0.27 | 0.15 | 0.21 | 0.14 | 0.16 | 0.14 | 0.11 | 0.18 | 0.16 | 0.19 |
| CRC+ | CBSE016 | I | 10.35 | 0.42 | 6.84 | 6.84 | 5.23 | 5.16 | 5.19 | 4.19 | 4.25 | 3.54 | 3.05 |
| CRC+ | CLSP100 | I | 21.61 | 6.39 | 4.46 | 3.46 | 3.31 | 3.46 | 3.35 | 2.68 | 2.68 | 2.26 | 1.81 |
| CRC+ | CLSP145 | I | 12.23 | 0.45 | 0.34 | 0.48 | 0.28 | 0.34 | 0.30 | 0.24 | 0.27 | 0.24 | 0.33 |
| CRC+ | CLSP047 | I | 6.30 | 0.23 | 0.20 | 0.25 | 0.17 | 0.20 | 0.17 | 0.14 | 2.16 | 1.85 | 1.67 |
| CRC+ | CLSP059 | I | 16.34 | 0.53 | 0.46 | 0.40 | 0.35 | 0.38 | 0.37 | 0.30 | 0.33 | 0.29 | 0.26 |
| CRC+ | CLSP157 | II | 7.65 | 0.29 | 0.23 | 0.31 | 0.19 | 0.23 | 0.20 | 0.16 | 0.19 | 0.17 | 0.23 |
| CRC+ | CLSP107 | II | 17.01 | 5.06 | 3.73 | 2.87 | 2.66 | 3.73 | 2.82 | 2.26 | 2.18 | 1.93 | 1.69 |
| CRC+ | CLSP102 | II | 13.79 | 0.49 | 0.46 | 0.52 | 0.26 | 3.09 | 0.33 | 0.30 | 0.25 | 0.29 | 1.68 |
| CRC+ | CBSE004 | II | 4.75 | 19.61 | 0.41 | 0.41 | 9.94 | 0.35 | 10.05 | 8.04 | 7.99 | 6.73 | 5.79 |
| CRC+ | CLSP154 | II | 7.57 | 0.42 | 5.06 | 3.93 | 3.81 | 3.84 | 3.89 | 3.12 | 3.12 | 2.66 | 2.08 |
| CRC+ | CLSP136 | II | 12.34 | 0.48 | 0.46 | 0.56 | 0.32 | 0.41 | 0.40 | 0.32 | 0.32 | 0.33 | 0.38 |
| CRC+ | CLSP096 | II | 9.67 | 0.34 | 10.09 | 7.65 | 7.52 | 7.62 | 7.60 | 6.08 | 6.04 | 5.09 | 3.88 |
| CRC+ | CLSP093 | II | 25.85 | 7.66 | 5.24 | 4.01 | 3.88 | 5.24 | 3.95 | 3.16 | 3.15 | 2.67 | 2.33 |
| CRC+ | CLSP117 | II | 20.32 | 6.16 | 4.24 | 3.41 | 3.20 | 3.37 | 3.26 | 2.61 | 2.68 | 2.27 | 1.92 |
| CRC+ | CLSP133 | II | 9.37 | 0.30 | 0.30 | 0.37 | 0.18 | 0.28 | 0.23 | 0.19 | 0.19 | 0.19 | 0.25 |
| CRC+ | CLSP115 | II | 50.36 | 14.98 | 10.09 | 10.14 | 7.59 | 7.80 | 7.63 | 6.10 | 6.15 | 5.15 | 5.27 |
| CRC+ | CBSE017 | II | 13.84 | 0.45 | 8.84 | 8.84 | 6.74 | 6.79 | 6.65 | 5.42 | 5.44 | 4.56 | 4.00 |
| CRC+ | CLSP085 | II | 9.77 | 0.39 | 0.28 | 0.37 | 0.23 | 0.28 | 0.26 | 0.21 | 0.22 | 0.20 | 0.26 |
| CRC+ | CLSP143 | II | 14.20 | 0.46 | 4.10 | 3.20 | 3.07 | 3.25 | 3.09 | 2.48 | 2.52 | 2.12 | 1.74 |
| CRC+ | CLSP110 | II | 10.12 | 0.36 | 0.23 | 0.26 | 0.19 | 0.23 | 0.20 | 0.16 | 0.21 | 0.19 | 0.21 |
| CRC+ | CLSP060 | II | 18.62 | 5.64 | 4.01 | 3.15 | 2.93 | 4.01 | 3.08 | 2.46 | 2.42 | 2.11 | 1.89 |
| CRC+ | CLSP122 | II | 7.35 | 0.26 | 0.47 | 0.51 | 0.29 | 2.94 | 0.38 | 0.30 | 0.33 | 0.33 | 1.61 |
| CRC+ | CLSP119 | II | 16.72 | 0.55 | 0.36 | 0.47 | 0.28 | 2.85 | 0.30 | 0.24 | 0.33 | 0.29 | 1.61 |
| CRC+ | CLSP147 | II | 7.94 | 0.29 | 0.26 | 2.87 | 0.21 | 0.32 | 0.22 | 0.18 | 0.35 | 0.29 | 1.62 |
| CRC+ | CLSP105 | II | 8.80 | 0.41 | 12.03 | 11.73 | 8.90 | 9.07 | 9.10 | 7.28 | 7.17 | 6.11 | 5.96 |
| CRC+ | CLSP075 | II | 14.61 | 0.49 | 0.40 | 0.37 | 0.30 | 0.40 | 0.33 | 0.26 | 0.30 | 0.27 | 0.27 |
| CRC+ | CLSP088 | II | 16.64 | 0.53 | 11.70 | 8.78 | 5.34 | 11.70 | 8.80 | 7.04 | 5.37 | 6.58 | 5.75 |
| CRC+ | CLSP086 | II | 7.36 | 0.25 | 83.24 | 62.51 | 62.37 | 83.24 | 62.45 | 49.96 | 49.91 | 41.65 | 35.74 |
| CRC+ | GHBD020 | II | 14.40 | 0.47 | 0.38 | 0.34 | 0.27 | 0.38 | 0.31 | 0.26 | 3.09 | 2.77 | 1.78 |
| CRC+ | GHBD029 | II | 10.52 | 0.34 | 0.33 | 0.36 | 0.26 | 0.33 | 0.26 | 0.27 | 0.46 | 0.44 | 0.41 |
| CRC+ | GHBD025 | II | 7.67 | 0.25 | 0.22 | 0.37 | 0.16 | 0.22 | 0.18 | 0.15 | 2.49 | 2.19 | 2.17 |
| CRC+ | CLSP076 | II | 16.46 | 0.51 | 0.40 | 0.41 | 0.32 | 0.40 | 0.31 | 0.26 | 2.85 | 2.53 | 1.59 |
| CRC+ | CBSE007 | III | 59.64 | 17.94 | 11.83 | 11.83 | 17.31 | 8.90 | 9.05 | 13.88 | 13.95 | 11.65 | 10.00 |
| CRC+ | CBSE010 | III | 23.32 | 7.00 | 34.14 | 34.14 | 3.76 | 34.14 | 25.66 | 20.56 | 3.03 | 17.15 | 17.15 |
| CRC+ | CBSE013 | III | 19.10 | 5.66 | 4.25 | 4.25 | 3.05 | 3.30 | 3.21 | 2.64 | 2.54 | 2.28 | 2.02 |
| CRC+ | CBSE023 | III | 11.91 | 0.45 | 0.56 | 0.56 | 0.36 | 0.46 | 0.47 | 0.38 | 0.37 | 0.38 | 0.35 |
| CRC+ | CLSP091 | III | 18.63 | 5.57 | 4.05 | 3.13 | 2.99 | 4.05 | 3.07 | 2.46 | 2.40 | 2.06 | 1.81 |
| CRC+ | CLSP144 | III | 4.98 | 0.18 | 0.35 | 0.26 | 0.21 | 0.30 | 0.28 | 0.22 | 0.21 | 0.22 | 0.18 |
| CRC+ | CLSP123 | III | 42.46 | 12.72 | 8.50 | 9.33 | 6.41 | 8.50 | 6.48 | 5.18 | 5.28 | 4.44 | 5.49 |
| CRC+ | CBSE006 | III | 11.78 | 10.90 | 0.34 | 0.34 | 16.22 | 0.33 | 5.53 | 13.02 | 12.98 | 10.85 | 9.34 |
| CRC+ | CLSP097 | III | 10.37 | 0.36 | 0.32 | 0.29 | 0.22 | 0.28 | 0.27 | 0.21 | 0.21 | 0.21 | 0.20 |
| CRC+ | CLSP106 | III | 18.88 | 5.63 | 3.76 | 2.95 | 2.81 | 3.76 | 2.85 | 2.28 | 2.29 | 1.93 | 1.73 |
| CRC+ | CLSP141 | III | 28.93 | 8.60 | 5.77 | 4.52 | 4.34 | 5.77 | 4.36 | 3.49 | 3.52 | 2.95 | 2.64 |
| CRC+ | CLSP073 | III | 16.34 | 0.55 | 8.64 | 6.54 | 0.37 | 6.69 | 6.51 | 5.21 | 0.32 | 4.36 | 3.41 |
| CRC+ | CLSP069 | III | 9.72 | 0.33 | 0.41 | 0.41 | 0.22 | 0.44 | 0.33 | 0.26 | 0.22 | 0.26 | 0.31 |
| CRC+ | CLSP121 | III | 8.28 | 0.34 | 0.27 | 2.76 | 0.21 | 0.24 | 0.25 | 0.20 | 0.26 | 0.25 | 1.49 |
| CRC+ | CLSP101 | III | 18.92 | 5.59 | 3.96 | 3.20 | 2.94 | 3.21 | 2.98 | 2.39 | 2.39 | 2.02 | 1.74 |
| CRC+ | CLSP103 | III | 7.16 | 0.29 | 0.22 | 0.24 | 0.18 | 0.24 | 0.20 | 0.16 | 0.22 | 0.19 | 0.22 |
| CRC+ | CLSP098 | III | 11.49 | 0.38 | 0.31 | 0.23 | 0.20 | 0.30 | 0.25 | 0.20 | 0.17 | 0.19 | 0.18 |
| CRC+ | CLSP138 | III | 8.51 | 0.34 | 4.79 | 3.72 | 3.62 | 4.79 | 3.64 | 2.91 | 3.03 | 2.54 | 2.25 |
| CRC+ | CLSP044 | III | 4.98 | 0.23 | 51.43 | 38.69 | 38.56 | 38.62 | 38.61 | 30.89 | 30.88 | 25.77 | 19.41 |
| CRC+ | CBSE005 | III | 20.97 | 15.29 | 4.30 | 3.43 | 17.66 | 4.30 | 7.78 | 14.23 | 28.03 | 24.10 | 20.61 |
| CRC+ | CLSP074 | III | 14.21 | 0.47 | 0.48 | 0.42 | 0.29 | 0.41 | 0.39 | 0.32 | 0.26 | 0.29 | 0.27 |
| CRC+ | CLSP153 | III | 47.87 | 14.16 | 25.18 | 18.89 | 14.45 | 25.18 | 18.91 | 15.14 | 11.09 | 11.94 | 10.90 |
| CRC+ | CLSP050 | III | 15.69 | 0.49 | 0.44 | 0.41 | 0.32 | 0.44 | 0.34 | 0.28 | 3.34 | 2.88 | 2.56 |
| CRC+ | CLSP072 | III | 15.50 | 0.49 | 5.98 | 4.63 | 0.45 | 5.98 | 4.50 | 3.60 | 3.56 | 5.36 | 4.76 |
| CRC+ | CLSP089 | III | 5.75 | 0.20 | 12.91 | 9.88 | 9.53 | 12.91 | 9.70 | 7.77 | 8.92 | 8.01 | 7.73 |
| CRC+ | CLSP078 | III | 53.04 | 15.76 | 10.48 | 7.96 | 7.90 | 10.48 | 7.92 | 6.34 | 4.24 | 3.78 | 4.20 |
| CRC+ | GHBD019 | III | 10.37 | 0.34 | 3.57 | 2.76 | 2.70 | 3.57 | 2.69 | 2.16 | 1.66 | 1.47 | 1.57 |
| CRC+ | CLSP159 | IV | 12.45 | 0.52 | 53.31 | 42.90 | 25.12 | 53.31 | 40.06 | 32.05 | 20.24 | 26.83 | 24.66 |
| CRC+ | CBSE012 | IV | 4.98 | 0.23 | 7.49 | 7.49 | 0.32 | 7.49 | 5.66 | 4.52 | 0.33 | 3.83 | 3.83 |
| CRC+ | CLSP042 | IV | 22.79 | 16.50 | 80.47 | 63.87 | 65.23 | 80.47 | 65.24 | 52.32 | 52.23 | 43.64 | 39.42 |
| CRC+ | CLSP161 | IV | 12.99 | 0.43 | 9.27 | 7.13 | 6.82 | 7.00 | 6.97 | 5.58 | 5.53 | 4.71 | 3.65 |
| CRC+ | CBSE019 | IV | 19.47 | 5.80 | 4.26 | 4.26 | 3.12 | 3.44 | 3.22 | 2.58 | 2.52 | 2.17 | 2.00 |
| CRC+ | CLSP057 | IV | 31.56 | 9.53 | 13.81 | 10.59 | 10.41 | 13.81 | 10.46 | 8.37 | 8.44 | 7.07 | 6.20 |
| CRC+ | CLSP160 | IV | 101.79 | 30.07 | 20.33 | 15.36 | 15.22 | 20.33 | 15.27 | 12.22 | 12.25 | 10.25 | 8.85 |
| CRC+ | CLSP095 | IV | 15.79 | 0.65 | 74.92 | 56.37 | 56.10 | 56.24 | 56.28 | 45.03 | 44.92 | 37.56 | 28.28 |

TABLE 8-continued

| Pathological condition | Sample identifier | Stage | L-FABP ng/ml | Total score 2[a] | Total score 3[b] | Total score 4[c] | Total score 4[d] | Total score 4[e] | Total score 4[f] | Total score 5[g] | Total score 8[h] | Total score 9[i] | Total score 9[j] |
|---|---|---|---|---|---|---|---|---|---|---|---|---|---|
| CRC+ | CLSP132 | IV | 29.79 | 8.84 | 6.23 | 7.57 | 4.53 | 4.83 | 4.70 | 3.76 | 3.74 | 3.24 | 3.95 |
| CRC+ | CBSE008 | IV | 4.77 | 0.18 | 0.20 | 0.16 | 0.36 | 0.20 | 0.17 | 0.32 | 0.37 | 0.34 | 0.31 |
| CRC+ | CBSE003 | IV | 17.08 | 5.07 | 72.70 | 54.58 | 48.16 | 72.70 | 54.54 | 43.72 | 32.36 | 31.45 | 36.47 |
| CRC+ | CLSP068 | IV | 21.38 | 6.64 | 241.47 | 184.41 | 128.03 | 241.47 | 181.27 | 145.03 | 84.44 | 100.51 | 115.01 |
| CRC+ | CBSE026 | IV | 18.36 | 5.71 | 171.19 | 128.55 | 75.29 | 171.19 | 128.54 | 102.84 | 46.46 | 67.29 | 75.20 |
| CRC+ | CLSP156 | IV | 11.69 | 0.38 | 36.88 | 32.92 | 17.04 | 36.88 | 27.67 | 22.15 | 11.68 | 15.55 | 20.63 |
| CRC+ | CBSE021 | IV | 8.06 | 0.36 | 121.06 | 90.93 | 90.62 | 121.06 | 90.86 | 72.69 | 54.24 | 47.58 | 54.30 |
| | Threshold | | 16.96 | 0.73 | 0.62 | 0.67 | 0.52 | 0.62 | 0.58 | 0.46 | 0.57 | 0.52 | 0.51 |
| | Specificity (%) | | 100 | 100 | 100 | 100 | 100 | 100 | 100 | 100 | 100 | 100 | 100 |
| | Sensitivity (%) | | 33.75 | 36.25 | 60.00 | 62.50 | 57.50 | 63.75 | 62.50 | 62.50 | 65.00 | 68.75 | 75.00 |
| | CRC + greater than the threshold | | 27 | 29 | 48 | 50 | 46 | 51 | 50 | 50 | 52 | 55 | 60 |

[a]combination of L-FABP and LEI
[b]combination of L-FABP, ACE and CA 19-9
[c]combination of L-FABP, ACE, CA 19-9 and Gal-3
[d]combination of L-FABP, ACE, ACY and LEI
[e]combination of L-FABP, ACE, CA 19-9 and Apo A1
[f]combination of L-FABP, ACE, CA 19-9 and LEI
[g]combination of L-FABP, ACE, CA 19-9, LEI and ACY
[h]combination of L-FABP, ACE, LEI, ACY, Beta2-Microglobulin, E-Cadherin, PAP and Proteasome 20S
[i]combination of L-FABP, ACE, CA19-9, LEI, ACY, Beta2-Microglobulin, E-Cadherin, PAP and Proteasome 20S
[j]combination of L-FABP, ACE, CA19-9, LEI, ACY, Beta2-Microglobulin, Gal-3, Apo A1 and Proteasome 20S

EXAMPLE 5: FECAL TUMOR MARKER ASSAYS

The stools are extracted using a piece weighing approximately 1 g, to which 10 ml of 100 mM sodium phosphate buffer, pH 7.2, containing 1 g/L of azide are added. The mixture is homogenized on a vortex for 1 min. The sample is then subjected to 4 cycles of ultrasound for 7 s on ice. The unsolubilized fraction is removed by centrifugation at 2000 g, for 10 min at 4° C. The supernatant is stored at −30° C. until it is assayed.

The ELISA assays described in Example 3 were used to search for the tumor markers in the stools after, if necessary, an appropriate dilution of the stools in the buffer of the first well of the HBs Ag Ultra cartridge.

The assay determinations with the tests, Aminoacylase 1, Galectin-3 and Proteasome 20S, have been represented, respectively, in FIGS. 18 to 20. An increase in the amount of Aminoacylase 1, of Galectin-3 and of Proteasome 20S is observed, respectively, for 10, 14 and 8 stools of patients having colorectal cancer.

EXAMPLE 6: DETECTION OF THE TUMOR MARKERS BY THE ELISPOT TECHNIQUE

1. Cell Culture

The LnCAP prostate cancer line is cultured in RPMI 1640 medium supplemented with 2 mM L-glutamine, 10 mM HEPES, 1 mM sodium pyruvate and 10% FCS (all Gibco). The cells are used as a negative control.

The Caco-2 colorectal cancer line is cultured in DMEM medium containing 2 mM L-glutamine, without FCS (all Gibco).

The HT-29 colorectal cancer line is cultured in MEM medium containing 2 mM L-glutamine and 10% FCS (all Gibco).

The HT-29/B6 colorectal cancer line is cultured in DMEM medium containing 4 mM L-glutamine, without FCS (all Gibco).

The cells are maintained at 37° C., in an incubator with 5% $CO_2$.

2. The ELISPOT Technique

This procedure makes it possible to determine the number of cells secreting the protein. The 96-well ELISPOT plates with PVDF membranes (Multiscreen IP, Millipore) are coated with the mouse anti-tumor marker monoclonal antibody at 10 µg/ml (capture antibody, see Table 9 below, which gives the antibodies used in ELISPOT), 100 µl per well, in sterile PBS, overnight at +4° C. The plates are then washed with PBS and saturated with culture medium containing 10% FCS. In parallel, the cells are trypsinized, counted, and then diluted to $10^5$ cells/ml. 200 µl of this cell suspension are distributed per well, as are cascade dilutions of this stock solution. The plates are then incubated for 20 h at 37° C. in a humid atmosphere at 5% $CO_2$, and then washed with PBS containing 0.05% Tween-20. The remaining cells are then lyzed by treatment with ice-cold water for 10 minutes, and then the plates are again washed. The revealing antibody, the biotinylated monoclonal directed against the tumor marker to be assayed (Table 9), is then added at 0.1 µg/well (incubation for 2 h at ambient temperature). The spots are revealed by adding extravidin-alkaline phosphatase (Sigma) and the substrate 5-bromo-4-chloro-3-indolyl phosphate/nitro blue tetrazolium (BCIP/NBT, Biorad). The background noise corresponds to the number of spots measured in the LnCap wells and varies between 0 and 8 spots under the reading conditions used. The average number of nonspecific spots was subtracted from the specific signal.

TABLE 9

| Marker | Capture Ab | Detection Ab |
|---|---|---|
| LEI | 10E1H1 | 21B10A5 |
| Ezrin | 4A9H5 | 4A7A6C1 |
| Galectin-3 | 12F8A12 | 14A5G1 |

3. Results

The number of Caco-2, HT-29 and HT-29/B6 cells secreting the tumor marker of interest, per million incubated cells, is shown in FIG. 21. The ELISPOT technique makes it possible to confirm the release or the secretion of the tumor markers by the colon cancer lines. It will be possible to carry out a search for circulating tumor cells in patients using this technique, according to the method of patent application WO 03/076942 filed by the applicant.

EXAMPLE 7: IMMUNOHISTOCHEMICAL DETECTION OF THE TUMOR MARKERS USING COLONIC TISSUES

1. Methodology

Firstly, the tissue-microarray slides are deparaffinized. For this, they are incubated successively in the following baths for 10 minutes: methylcyclohexane (twice), 100% ethanol, 95% ethanol, 70% ethanol and water. The slides are then rinsed with TBS containing 0.1% Tween 20 (TBS-T), for 10 min, with stirring. The antigens are reactivated in 10 mM citrate buffer, pH 6, by heating to 90° C. for 40 min, and then by allowing to cool to ambient temperature for 30 min. The endogenous peroxidases are inhibited by incubation in TBS-T containing 3% $H_2O_2$, for 5 min. The slides are then saturated with 3% BSA in TBS-T, for 1 h at 37° C., in a humid chamber.

The slides are then incubated for 2 h with the anti-Leukocyte Elastase Inhibitor (clone 3D9C2), anti-Ezrin (clone 5G2D12), anti-Aminoacylase 1 (clone 8A8A10) or anti-I-Plastin (clone 8D6A3) primary antibody diluted to 10 µg/ml in TBS-T containing 3% BSA (incubation at 37° C. in a humid chamber). After 3 washes of 10 min in TBS-T, the slides are incubated for 2 h at 37° C., in a humid chamber, with the horseradish peroxidase-coupled anti-mouse secondary antibody (Cat. No. 115-035-003 Jackson Immunoresearch) diluted to 1/400 in the saturating solution. The slides are washed 3 times for 10 minutes in TBS-T, and then 3 times for 10 min in PBS. The slides are developed with the Sigma Fast substrate (Cat. No. D-4168, Sigma-Aldrich) for 5 min. The staining is stopped by washing in PBS. Counterstaining with Harris hematoxylin (Cat. No. MHS16, Sigma-Aldrich) is carried out for 30 sec. After washing with water and with PBS, the slides are mounted for observation under a microscope.

The antibodies used for the immunohistochemical labeling were selected specifically for this application, independently of their reactivity in ELISA or in Western blotting.

2. Immunohistochemical Detection of Leukocyte Elastase Inhibitor

Tissue-microarray slides were used to screen a large number of samples. These samples are colonic tissues spotted onto slides. The characteristics of the patients (characteristics of the colonic tissue spots present on the colorectal cancer tissue-microarray), and also the results of the immunolabelings with the anti-Leukocyte Elastase Inhibitor antibody, are reproduced in Table 10.

TABLE 10

| Diagnosis | Histology and genetic characterization | Labeling in epithelial cells | Labeling in the stroma |
|---|---|---|---|
| Malignant tumor | Conserved adenocarcinoma | Positive | Negative |
| Malignant tumor | Conserved adenocarcinoma | Positive | Negative |
| Normal | Normal mucosa | Negative | Negative |
| Normal | Normal mucosa | Negative | Negative |
| Normal | Normal mucosa | Negative | Negative |
| Normal | Normal mucosa | Negative | Negative |
| Benign tumor | Adenoma | Negative | Negative |
| Malignant tumor | Conserved adenocarcinoma | Positive | Negative |
| Malignant tumor | LOH adenocarcinoma | Positive | Negative |
| Malignant tumor | LOH adenocarcinoma | Positive | Negative |
| Normal | Normal mucosa | Negative | Negative |

TABLE 10-continued

| Diagnosis | Histology and genetic characterization | Labeling in epithelial cells | Labeling in the stroma |
|---|---|---|---|
| Normal | Normal mucosa | Negative | Negative |
| Normal | Normal mucosa | Negative | Negative |
| Normal | Normal mucosa | Negative | Negative |
| Malignant tumor | LOH adenocarcinoma | Negative | Negative |
| Malignant tumor | LOH adenocarcinoma | Positive | Negative |
| Malignant tumor | MSI-high adenocarcinoma | Positive | Negative |
| Malignant tumor | MSI-high adenocarcinoma | Positive | Negative |
| Malignant tumor | Colloid adenocarcinoma | Negative | Negative |
| Malignant tumor | Colloid adenocarcinoma | Negative | Negative |
| Normal | Normal mucosa | Negative | Negative |
| Normal | Normal mucosa | Negative | Negative |

The results in the table demonstrate that, in the healthy colonic mucosa biopsies, there is no labeling (10 negatives). The labeling is also negative in the adenoma (1/1). The labeling is positive in the epithelial cells of the colonic adenocarcinomas (+ in 8/11 patients). There is no labeling in the stroma.

3. Immunohistochemical Detection of Ezrin

Tissue-microarray slides were used to screen a large number of samples. These samples are colonic tissues spotted onto slides. For each patient with a colonic adenocarcinoma, 3 samples were taken at the center of the tumor, 3 samples were taken at the invasion front and 3 samples were taken in the healthy tissue. Table 11 shows the results of the immunolabelings with the anti-Ezrin antibody; the level of labeling indicated is the maximum intensity over the 3 samples analyzed.

TABLE 11

| Patient identifier | Tumor center | Tumor invasion front | HEALTHY tissue |
|---|---|---|---|
| 55 | + | ++ | 0 |
| 127 | + | + | 0 |
| 329 | + | ++ | + |
| 475 | + | ++ | + |
| 544 | + | ++ | + |
| 726 | + | + | + |
| 1203 | ++ | ++ | + |
| 1310 | ++ | +++ | + |
| 2003 | + | 0 | + |
| 2296 | ++ | ++ | 0 |
| 2301 | + | ++ | + |
| 2377 | + | + | 0 |
| 3095 | + | + | 0 |
| 3430 | + | + | 0 |
| 3636 | + | + | 0 |
| 3748 | + | + | 0 |
| 3839 | + | ++ | 0 |
| 3891 | 0 | 0 | 0 |
| 4054 | + | + | 0 |
| 4322 | + | ++ | 0 |
| 445 | 0 | ++ | + |
| 4474 | ++ | ++ | 0 |
| 4792 | + | + | + |
| 4958 | ++ | ++ | + |
| 5101 | + | ++ | + |
| 5318 | ++ | +++ | 0 |
| 5374 | + | + | 0 |
| 5472 | + | 0 | + |
| 6340 | ++ | + | 0 |
| 6353 | ++ | + | 0 |

In a sampling of 30 patients, 25 exhibit overexpression of Ezrin in the tumor (tumor center or invasion front) compared with the adjacent healthy tissue.

4. Immunohistochemical Detection of Aminoacylase 1

Tissue-microarray slides were used to screen a large number of samples. These samples are colonic tissues spotted onto slides. For each patient with a colonic adenocarcinoma, 3 samples were taken at the center of the tumor, 3 samples were taken at the invasion front and 3 samples were taken in the healthy tissue. Table 12 shows the results of the immunolabelings with the anti-Aminoacylase antibody; the level of labeling indicated is the maximum intensity over the 3 samples analyzed.

TABLE 12

| Patient identifier | Tumor center | Tumor invasion front | Healthy tissue |
|---|---|---|---|
| 55 | ++ | ++ | 0 |
| 127 | 0 | 0 | 0 |
| 329 | ++ | ++ | 0 |
| 475 | ++ | ++ | + |
| 544 | + | 0 | 0 |
| 726 | 0 | 0 | 0 |
| 1203 | 0 | + | 0 |
| 1310 | 0 | + | + |
| 2003 | ++ | 0 | 0 |
| 2296 | + | + | 0 |
| 2301 | + | + | + |
| 2377 | + | + | + |
| 3095 | + | + | 0 |
| 3430 | + | + | + |
| 3636 | ++ | + | + |
| 3748 | ++ | ++ | 0 |
| 3839 | ++ | ++ | + |
| 3891 | ++ | ++ | 0 |
| 4054 | + | ++ | 0 |
| 4322 | +++ | +++ | + |
| 445 | + | ++ | + |
| 4474 | + | ++ | + |
| 4792 | ++ | ++ | + |
| 4958 | + | + | + |
| 5101 | + | + | ++ |
| 5318 | +++ | ++ | 0 |
| 5374 | + | + | 0 |
| 5472 | ++ | ++ | + |
| 6340 | ++ | ++ | + |
| 6353 | ++ | ++ | ++ |

In a sampling of 30 patients, 21 exhibited overexpression of Aminoacylase in the tumor (tumor center or invasion front) compared with the adjacent healthy tissue.

5. Immunohistochemical Detection of I-Plastin

Tissue-microarray slides were used to screen a large number of samples. These samples are colonic and rectal tissues spotted onto slides. The characteristics of the patients (characteristics of the colonic tissue spots present on the colorectal cancer tissue-microarray), and also the results of the immunolabelings with the anti-I-Plastin antibody, are reproduced in Table 13.

TABLE 13

| Diagnosis | Histology and genetic characterization | Labeling in the epithelial cells | Labeling in the stroma |
|---|---|---|---|
| Malignant colon tumor | Conserved adenocarcinoma | ++ | Negative |
| Malignant colon tumor | Conserved adenocarcinoma | ++ | Negative |
| Normal colon | Normal mucosa | + | Negative |
| Normal colon | Normal mucosa | + | Negative |
| Normal colon | Normal mucosa | + | Negative |
| Benign colon tumor | Adenoma | + | Negative |
| Malignant colon tumor | Conserved adenocarcinoma | + | Negative |
| Malignant colon tumor | LOH adenocarcinoma | ++ | Negative |
| Malignant colon tumor | LOH adenocarcinoma | ++ | Negative |
| Normal colon | Normal mucosa | + | Negative |
| Normal colon | Normal mucosa | + | Negative |
| Normal colon | Normal mucosa | + | Negative |
| Malignant colon tumor | LOH adenocarcinoma | ++ | Negative |
| Malignant colon tumor | LOH adenocarcinoma | ++ | Negative |
| Malignant colon tumor | MSI-high adenocarcinoma | + | Negative |
| Normal colon | Normal mucosa | + | Detached |
| Normal colon | Normal mucosa | + | Detached |
| Malignant colon tumor | Colloid adenocarcinoma | + | Negative |
| Normal colon | Normal mucosa | ++ | Negative |
| Normal colon | Normal mucosa | ++ | Negative |
| Normal rectum | Normal rectal mucosa | ++ | Negative |
| Normal rectum | Normal rectal mucosa | Nonspecific | Negative |
| Normal rectum | Normal rectal mucosa | Nonspecific | Negative |
| Normal rectum | Normal rectal mucosa | Nonspecific | Negative |
| Malignant rectal tumor | LOH adenocarcinoma | + | Negative |
| Malignant rectal tumor | LOH adenocarcinoma | ++ | Negative |
| Malignant rectal tumor | LOH adenocarcinoma | ++ | Negative |
| Malignant rectal tumor | LOH adenocarcinoma | ++ | Negative |
| Benign rectal tumor | Adenoma with low-grade dysplasia | ++ | Negative |
| Benign rectal tumor | Adenoma with low-grade dysplasia | ++ | Negative |
| Benign rectal tumor | Adenoma with low-grade dysplasia | + | Negative |
| Benign rectal tumor | Adenoma with low-grade dysplasia | + | Negative |
| Benign rectal tumor | Adenoma with low-grade dysplasia | + | Negative |
| Benign rectal tumor | Adenoma with low-grade dysplasia | + | Negative |
| Benign rectal tumor | Adenoma with low-grade dysplasia | ++ | Negative |
| Benign rectal tumor | Adenoma with low-grade dysplasia | ++ | Negative |
| Benign rectal tumor | Adenoma with low-grade dysplasia | ++ | Negative |

The results in the table demonstrate that:
in the healthy colonic mucosa biopsies, the labeling is weak in 8 samples (+) and 2 samples are ++. The labeling is also weak (+) in the colonic adenoma (1/1). The labeling is strongly positive ++ in the epithelial cells of the colonic adenocarcinomas (++ in 6/9 patients and 3 weak +, including the colonic colloid adenocarcinomas). There is no labeling in the stroma;
in the healthy rectal mucosa biopsies, labeling is present in the surface epithelium in a nonspecific manner (3/4) and at ++ level in one sample. The labeling is strongly positive ++ in the rectal adenomas (5/9) or discreet + (4/9). The labeling is also strong ++ in the epithelial cells of the rectal adenocarcinomas (++ in 3/4 patients, 1 weak +). There is no labeling in the stroma.

LITERATURE REFERENCES

1. J. D. Potter, J Natl Cancer Inst., 91, 916-32
2: J. Faivre, 2001, Epidémiologie et dépistage du cancer colorectal [Colorectal cancer epidemiology and screening], publisher Springer
3: E. Chan et al., 1985, J Biol Chem, 260, 2629-2632
4: R. Das et al., 2001, Clin Cancer Res, 7, 1706-1715
5: J. Stulik et al., 2001, Electrophoresis, 22, 3019-3025
6: T. Yamazaki et al., 1999, J Surg Oncol, 72, 83-87
7: P. Gold et S. Freedman, 1965, J Exp Med, 467-481
8: M. Duffy, 2001, Clin Chem, 624-630
9: Y. Kim et al., 2003, Ann Clin Lab Sci, 32-38
10: J. L. Magnani et al., 1983, Cancer Research, 43, 5489-5492
11: E. Remold-O'Donnell et al., 1992, Proc Natl Acad Sci USA, 89, 563-5639
12: J. Cooley et al., 2001, Biochemistry, 15762-15770
13: M. Algrain et al., 1993, J Cell Biol, 120, 129-139
14: W. G. Jiang et S. Hiscox, 1996, Anticancer Res, 16, 861-865
15: S. Hiscox et W. G. Jiang, 1999, J Cell Sci, 112, 3081-3090
16: T. Xiao et al, 2005, Mol. Cell. Proteomics, 4, 1480-1486
17: M. Anders et W. Dekant, 1994, Advances in Pharmacology, 431-448
18: K. Lorentz et al., 1975, Clinica Chimica Acta, 263-269
19: K. Lorentz et B. Flatter, 1975, Clinica Chimica Acta, 271-274
20: R. M. Cook et al., 1993, J Bio Chem, 17010-17017
21: Y. E. Miller et al., 1989, J Clin Invest, 2120-2124
22: S. Balabanov et al., 2001, Eur J Biochem, 5977-5980
23: D. A. Sweetser et al., 1987, J Biol Chem, 266, 16060-16071
24: M. Pelsers et al., 2003, Clin Biochem, 36, 529-535
25: R. Xiao, et al., 2005, Molecular Cancer, 4, 1-17
26: E. E. Niederkofler et al., 2003, J Lipid Res, 44, 630-639
27: G. L. Hortin, 2006, Clinical Chemistry, 52(7), 1223-1237
28: J. Y. Engwegen et al., 2006, World J Gastroenterol, 12(10), 1536-1544
29: Z. Zhang et al., 2004, Cancer Research, 64, 5882-5890
30: H. Hachem et al., 1986, J Chem Clin Biochem, 24, 161-166
31: C. S. Lin, et al., 1993, J Biol Chem, 268, 2781-92
32: V. Delanote et al., 2005, Acta Pharama Sinica 769-779
33: S. Nakahara et al., 2005, Apoptosis, 10, 267-275
34: I. Iurisci et al., 2000, Clin Can Res, 6, 1389-1393
35: A. P. Arrigo et al., 1988, Nature, 331, 192-194
36: T Lavabre-Bertrand et al., 2001, Cancer, 92, 2493-2500
37: M. K. Scwartz, 2006, Clin Chim Acta, 1992, 77-82
38: D. J. McCool et al., 1999, Biochem J, 593-600
39: J. L. Iovanna et al., 1994, Gastroenterology, 106, 728-734
40: Y. Motoo et al., 1999, Dig Dis Sci, 44, 1142-1147
41: M. Herlyn et al., 1979, Proc Natl Acad Sci USA, 76, 1438-1442
42: A. Armstrong et S. Eck, 2003, Cancer Biol Ther, 2, 320-325
43: D. Herlyn et al., 1982, Proc Natl Acad Sci USA, 79, 4761-4765
44: H Abe et al., 2002, J Immunol Methods, 270, 227-233
45: V. Barak et al., 2004, Clin Biochem, 37, 529-540
46: H. Kim et al., 2006, Ann Clin Lab Sci, 36, 294-298
47: F. Roca et al., 2006, J Surg Oncol, 151-160
48: C. H. Damsky et al., 1983, Cell, 455-466
49: M. Katayama et al., 1994, Br J Cancer, 580-585
50: C. Willmanns et al., 2004, Clin Exp Metastasis, 75-78
51: J. Holmgren et al., 1984, Br Med J (Clin. Re. Ed.), 288, Ed.), 288, 1479-1482
52: T. L. Klug et al., 1986, Int. J. Cancer, 38, 6661-669
53: P. Kuusela et al., 1991, Br. J. Cancer, 63, 636-640
54: M. Holland et al., 1993; Medicina (B. Aires), 53(2):117-23
55: F. Model et al., July 2006, World Congress on Gastrointestinal Cancer, <<Detection of Methylated DNA in Plasma from Colorectal Cancer Patients and Controls by Real-Time PCR Analysis of Septin 9>>
56: M. P. Ebert et al., 2006, Gastroentrology, 131(5), 1418-1430
57: C. Bianco et al., 2006, Clin. Cancer Res., 12, 5158-5164
58: R. Yasumatsu et al., 2006, Am J Physiol Lung Cell Mol Physiol 291, L619-L627
59: J. Chevalier et al., 1997, J Histochem Cytochem, 45, 481-491
60: S. Patterson, 2000, Mass spectrometry and proteomics. Physiological Genomics 2, 59-65
61: L. Anderson and C. L. Hunter, 2006, Mol Cell Proteomics, 5, 573-588.
62: L. J. Kricka et al., 1999, Clinical Chemistry, 45(4), 453-458
63: S. Tyagi and F. R. Kramer, 1996, Nature Biotech, 14, 303-308
64: T. F. Imperiale et al., 2004, N Engl J Med, 351(26), 2704-2714
65: D. A. Ahlquist et al., 2000, Gastroenterology, 119, 1219-1227
66: I. H. Wong, 2006, Methods Mol Biol, 336, 33-46
67: M. P. Ebert et al., 2005, Neoplasia, 7(8), 771-778
68: C. Lofton-Day et al., 2007, AACR Annual Meeting 2007, Los Angeles, U.S.A., Poster no LB-165, Clinical case-control study in plasma shows that the DNA methylation biomarker, Septin-9, detects 70% of stage I-III colorectal cancer patients
69: P. Métézeau et al., La cytométrie en flux pour l'étude de la cellule normale ou pathologique (Tome I), Eds Medsi-MacGrawhill
70: Mathieu J. et al. 2006. Fonctions cellulaires et métabolisme. In: (coordonnateurs: Ronot X. et al.). La cytométrie en flux. Tec & Doc, 255-298. ISBN 978-2-7430-0898-7
71: V. Cheynet et al., 1993, Protein Expr Purif, 4(5), 367-372
72: G. Köhler and C. Milstein, 1975, Nature, 256, 495-497
73: G. Köhler and C. Milstein, 1976, Eur J Immunol, 6, 511-519

The invention claimed is:

1. A method comprising:
assaying amounts of Liver Fatty Acid-Binding Protein (L-FABP), Carcinoembryonic Antigen (CEA), and Carbohydrate Antigen 19.9 (CA 19-9) in a biological fluid sample from a person suspected of having colorectal cancer.

2. The method as claimed in claim 1, wherein L-FABP, CEA, and CA 19-9 are assayed by a biochemical test or by mass spectrometry.

3. The method as claimed in claim 1, further comprising assaying for at least one member selected from the group consisting of Leukocyte Elastase Inhibitor, Ezrin, Aminoacylase 1, Intestinal Fatty Acid-Binding Protein, Apolipoprotein AI, Apolipoprotein AII, and Galectin-3.

4. The method as claimed in claim 1, further comprising assaying for at least one member selected from the group consisting of Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Keratin type II Cytoskeletal 8, Keratin type I Cytoskeletal 18, Keratin type I Cytoskeletal 19, Epithelial-Cadherin, Villin, CA 242, CA 50, CA 72-2, Testosterone, TIMP-1, Cripto-1, Intelectin-1, Protein Disulfide Isomerase, Cytokeratin 20, Translationally-Controlled Tumor Protein, (Pro)defensin-A5, methylated DNA in the blood, specific alterations in fecal DNA fragments, and fecal human hemoglobin.

5. The method as claimed in claim 1, further comprising assaying for at least one member selected from the group consisting of Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Epithelial-Cadherin, Testosterone, TIMP-1, Intelectin-1, Protein Disulfide Isomerase, Cytokeratin 20, Translationally-Controlled Tumor Protein, (Pro) defensin-A5, and fecal human hemoglobin.

6. The method as claimed in claim 1, further comprising assaying for Galectin-3.

7. The method as claimed in claim 1, further comprising assaying for Apolipoprotein AI.

8. The method as claimed in claim 1, further comprising assaying for Leukocyte Elastase Inhibitor.

9. The method as claimed in claim 1, further comprising assaying for Leukocyte Elastase Inhibitor and Aminoacylase 1.

10. The method as claimed in claim 1, further comprising assaying for Leukocyte Elastase Inhibitor, Aminoacylase 1, Beta2-Microglobulin, Proteasome 20S, PAP, and E-Cadherin.

11. The method as claimed in claim 1, further comprising assaying for Leukocyte Elastase Inhibitor, Aminoacylase 1, Beta2-Microglobulin, Proteasome 20S, Galectin-3, and Apolipoprotein AI.

12. The method as claimed in claim 1, wherein the biological fluid sample is a blood or serum sample.

13. The method as claimed in claim 1, wherein the biological fluid sample is a stool sample.

14. The method as claimed in claim 1, wherein the biological fluid sample is a urine sample.

15. The method as claimed in claim 1, wherein L-FABP, CEA, and CA 19-9 are assayed by a biochemical test.

16. The method as claimed in claim 1, wherein L-FABP, CEA, and CA 19-9 are assayed by an immunoassay.

17. The method as claimed in claim 1, wherein L-FABP, CEA, and CA 19-9 are assayed by ELISA.

18. The method as claimed in claim 1, wherein L-FABP, CEA, and CA 19-9 are assayed using antibodies specific for L-FABP, CEA, and CA 19-9.

19. The method as claimed in claim 1, wherein L-FABP, CEA, and CA 19-9 are assayed using an automated device.

20. A method comprising:
assaying amounts of Liver Fatty Acid-Binding Protein (L-FABP), Carcinoembryonic Antigen (CEA), and Carbohydrate Antigen 19.9 (CA 19-9) in a biological fluid sample from a person suspected of having or having colorectal cancer.

21. The method as claimed in claim 20, further comprising assaying for at least one member selected from the group consisting of Leukocyte Elastase Inhibitor, Ezrin, Aminoacylase 1, Intestinal Fatty Acid-Binding Protein, Apolipoprotein AI, Apolipoprotein AII, and Galectin-3.

22. The method as claimed in claim 20, further comprising assaying for at least one member selected from the group consisting of Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Keratin type II Cytoskeletal 8, Keratin type I Cytoskeletal 18, Keratin type I Cytoskeletal 19, Epithelial-Cadherin, Villin, CA 242, CA 50, CA 72-2, Testosterone, TIMP-1, Cripto-1, Intelectin-1, Protein Disulfide Isomerase, Cytokeratin 20, Translationally-Controlled Tumor Protein, (Pro)defensin-A5, methylated DNA in the blood, specific alterations in fecal DNA fragments, and fecal human hemoglobin.

23. The method as claimed in claim 20, further comprising assaying for at least one member selected from the group consisting of Beta2-Microglobulin, Proteasome 20S, L-Lactate Dehydrogenase Chain B, Calreticulin, Regenerating Islet-Derived Protein 3 Alpha, Tumor-Associated Calcium Signal Transducer 1, Epithelial-Cadherin, Testosterone, TIMP-1, Intelectin-1, Protein Disulfide Isomerase, Cytokeratin 20, Translationally-Controlled Tumor Protein, (Pro)defensin-A5, and fecal human hemoglobin.

24. The method as claimed in claim 20, further comprising assaying for Galectin-3.

25. The method as claimed in claim 20, further comprising assaying for Apolipoprotein AI.

26. The method as claimed in claim 20, further comprising assaying for Leukocyte Elastase Inhibitor.

27. The method as claimed in claim 20, further comprising assaying for Leukocyte Elastase Inhibitor and Aminoacylase 1.

28. The method as claimed in claim 20, further comprising assaying for Leukocyte Elastase Inhibitor, Aminoacylase 1, Beta2-Microglobulin, Proteasome 20S, PAP, and E-Cadherin.

29. The method as claimed in claim 20, further comprising assaying for Leukocyte Elastase Inhibitor, Aminoacylase 1, Beta2-Microglobulin, Proteasome 20S, Galectin-3, and Apolipoprotein AI.

30. The method as claimed in claim 20, wherein the biological fluid sample is a blood or serum sample.

31. The method as claimed in claim 20, wherein the biological fluid sample is a stool sample.

32. The method as claimed in claim 20, wherein the biological fluid sample is a urine sample.

* * * * *